US010865230B2

(12) United States Patent
Liu et al.

(10) Patent No.: US 10,865,230 B2
(45) Date of Patent: Dec. 15, 2020

(54) CONSTRUCTION AND CHARACTERIZATION OF MULTIMERIC IL-15-BASED MOLECULES WITH CD3 BINDING DOMAINS

(71) Applicant: Altor Bioscience Corporation, Miramar, FL (US)

(72) Inventors: Bai Liu, Cooper City, FL (US); Peter Rhode, Miami, FL (US); Hing C. Wong, Weston, FL (US)

(73) Assignee: ALTOR BIOSCIENCE, LLC, Culver City, CA (US)

( * ) Notice: Subject to any disclaimer, the term of this patent is extended or adjusted under 35 U.S.C. 154(b) by 0 days.

(21) Appl. No.: 15/606,552

(22) Filed: May 26, 2017

(65) Prior Publication Data
US 2017/0342119 A1 Nov. 30, 2017

Related U.S. Application Data

(60) Provisional application No. 62/397,236, filed on Sep. 20, 2016, provisional application No. 62/342,311, filed on May 27, 2016.

(51) Int. Cl.
| *C07K 14/54* | (2006.01) |
| *C07K 16/24* | (2006.01) |
| *C07K 14/715* | (2006.01) |
| *C07K 16/00* | (2006.01) |
| *C07K 16/28* | (2006.01) |
| *A61K 39/395* | (2006.01) |
| *A61K 39/00* | (2006.01) |

(52) U.S. Cl.
CPC ...... *C07K 14/5443* (2013.01); *C07K 14/7155* (2013.01); *C07K 16/00* (2013.01); *C07K 16/2809* (2013.01); *C07K 16/2887* (2013.01); *A61K 2039/505* (2013.01); *C07K 2317/31* (2013.01); *C07K 2317/524* (2013.01); *C07K 2317/526* (2013.01); *C07K 2317/56* (2013.01); *C07K 2317/73* (2013.01); *C07K 2317/732* (2013.01); *C07K 2318/20* (2013.01); *C07K 2319/00* (2013.01); *C07K 2319/02* (2013.01); *C07K 2319/30* (2013.01); *C07K 2319/33* (2013.01); *C07K 2319/75* (2013.01)

(58) Field of Classification Search
None
See application file for complete search history.

(56) References Cited

U.S. PATENT DOCUMENTS

| 5,116,964 A | 5/1992 | Capon et al. |
| 5,541,087 A | 7/1996 | Lo et al. |
| 5,620,939 A | 4/1997 | Halasa et al. |
| 8,163,879 B2 | 4/2012 | Wong et al. |
| 8,492,118 B2 | 7/2013 | Wong et al. |
| 8,507,222 B2 | 8/2013 | Wong et al. |
| 8,940,289 B2 | 1/2015 | Wong et al. |
| 9,255,141 B2 | 2/2016 | Wong et al. |
| 9,328,159 B2 | 5/2016 | Wong et al. |
| 9,428,573 B2 * | 8/2016 | Wong ................. C07K 14/5443 |
| 9,464,127 B2 | 10/2016 | Wong et al. |
| 9,593,152 B2 | 3/2017 | Wong et al. |
| 9,925,247 B2 | 3/2018 | Liu et al. |
| 10,150,805 B2 | 12/2018 | Wong et al. |
| 2014/0205560 A1 * | 7/2014 | Wong ................. C07K 14/5443 424/85.2 |
| 2014/0242025 A1 * | 8/2014 | Wong ................. C07K 14/5443 424/85.2 |
| 2016/0355567 A1 | 12/2016 | Wong et al. |
| 2016/0367635 A1 | 12/2016 | Wong et al. |
| 2017/0088597 A1 | 3/2017 | Wong et al. |
| 2019/0022187 A1 | 1/2019 | Liu et al. |
| 2019/0023766 A1 | 1/2019 | Wong et al. |

(Continued)

FOREIGN PATENT DOCUMENTS

| EP | 3 464 352 A1 | 4/2019 |
| WO | WO-94/04689 A1 | 3/1994 |
| WO | WO-94/29350 A2 | 12/1994 |

(Continued)

OTHER PUBLICATIONS

International Search Report and Written Opinion dated Oct. 6, 2017 in corresponding PCT application No. PCT/US17/34656.

(Continued)

*Primary Examiner* — Bridget E Bunner
*Assistant Examiner* — Fozia Hamud
(74) *Attorney, Agent, or Firm* — Mintz, Levin, Cohn, Ferris, Glovsky and Popeo, P.C.

(57) ABSTRACT

The invention features soluble fusion protein complexes comprising at least two soluble fusion proteins. For example, the first fusion protein is an anti-CD3 antibody covalently linked to an interleukin-15 (IL-15) polypeptide or functional fragment thereof. The second fusion protein comprises a binding domain that recognizes disease antigens, wherein this domain is covalently linked to a soluble interleukin-15 receptor alpha (IL-15Rα) polypeptide or a functional fragment thereof. One or both of the first and second fusion proteins further includes an immunoglobulin Fc domain or a functional fragment thereof, and the IL-15 domain of first fusion protein binds to the soluble IL-15Rα domain of the second fusion protein to form a soluble fusion protein complex. The invention further provides methods for making and using the complexes of the invention.

15 Claims, 17 Drawing Sheets

Specification includes a Sequence Listing.

(56) References Cited

U.S. PATENT DOCUMENTS

2019/0048055 A1    2/2019  Shrestha et al.

FOREIGN PATENT DOCUMENTS

| WO | WO-96/32478 A1  | 10/1996 |
|----|-----------------|---------|
| WO | WO-97/34631 A1  | 9/1997  |
| WO | WO-2005/046449 A2 | 5/2005 |
| WO | WO-2008/143794 A1 | 11/2008 |
| WO | WO-2012/040323 A2 | 3/2012 |
| WO | WO-2016/018920 A1 | 2/2016 |
| WO | WO-2017/205726 A1 | 11/2017 |

OTHER PUBLICATIONS

International Preliminary Report on Patentability for Application No. PCT/US2017/034656, dated Dec. 6, 2018, 7 pages.
Abes et al. (Aug. 12, 2010) "Long-lasting Antitumor Protection by Anti-CD20 Antibody through Cellular Immune Response", Blood, 116(6):926-934.
Beers et al. (Apr. 2010) "CD20 as a Target for Therapeutic Type I and II Monoclonal Antibodies", Seminars in Hematology, 47(2):107-114.
Benton et al. (Apr. 8, 1977) "Screening λgt Recombinant Clones by Hybridization to Single Plaques in Situ", Science, 196(4286):180-182.
Capon et al. (Feb. 9, 1989) "Designing CD4 Immunoadhesins for AIDS Therapy", Nature, 337(6207):525-531.
Chamow et al. (Feb. 1996) "Immunoadhesins: Principles and Applications", Trends Biotechnology, 14:52-60.
Database Genbank (Sep. 14, 1995; retrieved from online on Apr. 1, 2020) "Mus Musculus Interleukin 15 (IL15) mRNA, Complete cds", Genbank Accession No. U14332.1, 2 pages.
Database Genbank (May 20, 2005; retrieved from online on Apr. 1, 2020) "Mus Musculus Interleukin 15 Receptor, Alpha Chain, mRNA (cDNA clone Image:4457379), Complete cds", Genbank Accession No. BC095982.1, 2 pages.
Davis (1985) "Molecular Genetics of the T Cell-receptor Beta Chain", Annual Review of Immunology, 3:537-560.
Dilillo et al. (May 21, 2015) "Differential Fc-Receptor Engagement Drives an Antitumor Vaccinal Effect", Cell, 161:1035-1045.
Fehniger et al. (Jan. 1, 2001) "Interleukin 15: Biology and Relevance to Human Disease", Blood, 97(1):14-32.
Fleer (Oct. 1992) "Engineering Yeast for High Level Expression", Current Opinion in Biotechnology, 3(5):486-496.
Frankel et al. (Oct. 2000) "Cell Surface Receptor-Targeted Therapy of Acute Myeloid Leukemia: A Review", Cancer Biotherapy & Radiopharmaceuticals, 15(5):459-476.
Gerber et al. (May/Jun. 2009) "Antibody Drug-Conjugates Targeting the Tumor Vasculature: Current and Future Developments", mAbs, 1(3):247-253.
Ghetie et al. (Mar. 1, 2001) "Homodimers but Not Monomers of Rituxan (Chimeric anti-CD20) Induce Apoptosis in Human B-lymphoma Cells and Synergize with a Chemotherapeutic Agent and an Immunotoxin", Blood, 97(5):1392-1398.
Gillies et al. (May 15, 2005) "An Anti-CD20-IL-2 Immunocytokine is Highly Efficacious in A SCID Mouse Model of Established Human B Lymphoma", Blood, 105(10):3972-3978.
Goede et al. (Jan. 8, 2014) "Obinutuzumab Plus Chlorambucil in Patients with CLL and Coexisting Conditions", New England Journal of Medicine, 9 pages.
Graham et al. (Jul. 1977) "Characteristics of a Human Cell Line Transformed by DNA from Human Adenovirus Type 5", Journal of General Virology, 36(1):59-72.
Grunstein et al. (Oct. 1975) "Colony Hybridization: A Method for the Isolation of Cloned DNAs That Contain a Specific Gene", Proceedings of the National Academy of Sciences of the United States of America, 72(10):3961-3965.
Guo et al. (2013) "Therapeutic Cancer Vaccines: Past, Present and Future", Advances in Cancer Research, 119:421-475.
Han et al. (Oct. 22, 2011) "IL-15:IL-15 Receptor Alpha Superagonist Complex: High-Level Co-Expression in Recombinant Mammalian Cells, Purification and Characterization", Cytokine, 56(3):804-810.
Hessell et al. (Sep. 6, 2007) "Fc Receptor but not Complement Binding is Important in Antibody Protection Against HIV", Nature, 449(7158):101-104.
Hilchey et al. (Apr. 16, 2009) "Rituximab immunotherapy results in the induction of a lymphoma idiotype-specific T-cell response in patients with follicular lymphoma: support for a "vaccinal effect" of rituximab", Blood, 113(16):3809-3812.
Hillmen et al. (May 9, 2015) "Chlorambucil Plus Ofatumumab Versus Chlorambucil Alone in Previously Untreated Patients With Chronic Lymphocytic Leukaemia (Complement 1): A Randomised, Multicentre, Open-Label Phase 3 Trial", The Lancet, 385(9980):1873-1883.
Hughes et al. (Apr. 2005) "Transfer of a TCR Gene Derived from a Patient with a marked Antitumor Response Conveys Highly Active T-Cell Effector Functions", Human Gene Therapy, 16(4):457-472.
Kimmel (1987) "Identification and Characterization of Specific Clones: Strategy for Confirming the Validity of Presumptive Clones", Methods in Enzymology, 152:507-511.
Li et al. (Apr. 1, 2008) "Development of Novel Tetravalent Anti-CD20 Antibodies with Potent Antitumor Activity", Cancer Research, 68(7):2400-2408.
Mathios et al. (Jan. 1, 2016) "Therapeutic Administration of IL-15 Superagonist Complex ALT-803 Leads to Long-term Survival and Durable Antitumor Immune Response in a Murine Glioblastoma Model", International Journal of Cancer, 138(1):187-194.
van Meerten et al. (Apr. 2010) "CD20-Targeted Therapy: The Next Generation of Antibodies", Seminars in Hematology, 47(2):199-210.
Moskaug et al. (Sep. 15, 1989) "Translocation of Diphtheria Toxin A-Fragment to the Cytosol. Role of the Site of Interfragment Cleavage", Journal of Biological Chemistry, 264(26):15709-15713.
Nishida et al. (2007) "Characterization of novel murine anti-CD20 monoclonal antibodies and their comparison to 2B8 and c2B8 (rituximab)", International Journal of Oncology, 31:29-40.
Novellino et al. (Mar. 2005; e-published on Aug. 7, 2004) "A Listing of Human Tumor Antigens Recognized by T Cells: Mar. 2004 Update", Cancer Immunology, Immunotherapy, 54(3):187-207.
Oleksiewicz et al. (Jun. 13, 2012) "Anti-bacterial Monoclonal Antibodies: Back to the Future?", Archives of Biochemistry and Biophysics, 526(2):124-131.
Olsnes et al. (1982) "Chimeric Toxins", Pharmacology and Therapeutics, 15(3):355-381.
Pardoll (Apr. 2012) "The Blockade of Immune Checkpoints in Cancer Immunotherapy", Nature Reviews Cancer, 12(4):252-264.
Park et al. (Aug. 17, 2010) "The Therapeutic Effect of Anti-HER2/neu Antibody Depends on Both Innate and Adaptive Immunity", Cancer Cell, 18(2):160-170.
Parmiani et al. (2007) "Unique Human Tumor Antigens: Immunobiology and Use in Clinical Trials", The Journal of Immunology, 178(4):1975-1979.
Pastan et al. (1992) "Recombinant Toxins as Novel Therapeutic Agents", Annual Review Biochemistry, 61:331-354.
Rhode et al. (Jan. 2016; e-published on Oct. 28, 2015) "Comparison of the Superagonist Complex, ALT-803, to IL15 as Cancer Immunotherapeutics in Animal Models", Cancer Research Immunology, 4(1):49-60.
Rosario et al. (2016; e-published on Sep. 30, 2015) "The IL-15-Based ALT-803 Complex Enhances FcγRIIIa-Triggered NK Cell Responses and in Vivo Clearance of B Cell Lymphomas", Clinical cancer research, 22:596-608.
Rossi et al. (Oct. 29, 2009) "CD20-Targeted Tetrameric Interferon-α, A Novel and Potent Immunocytokine for the Therapy of B-Cell Lymphomas", Blood, 114(18):3864-3871.
Seay et al. (Jan. 1, 2015; e-published on Apr. 1, 2015) "In Vivo Activation of Human NK Cells by Treatment with an Interleukin-15 Superagonist Potently Inhibits Acute In Vivo HIV-1 Infection in Humanized Mice", Journal of virology, 89(12):6264-6274.

(56) References Cited

OTHER PUBLICATIONS

Shi et al. (Mar. 24, 2015) "ImmunoPET of tissue factor expression in triple-negative breast cancer with a radiolabeled antibody Fab fragment", European Journal of nuclear medicine and molecular imaging, 42:1295-1303.

Shi et al. (Apr. 16, 2015) "PET Imaging of Abdominal Aortic Aneurysm with 64Cu-Labeled Anti-CD105 Antibody Fab Fragment", Journal of nuclear medicine, 56(6):927-932.

Sips et al. (Nov. 2016) "Fc receptor-mediated phagocytosis in tissues as a potent mechanism for preventive and therapeutic HIV vaccine strategies", Mucosal Immunology, 9:1584-1595.

Sliwkowski et al. (Sep. 13, 2013) "Antibody Therapeutics in Cancer", Science, 341(6151):1192-1198.

Smalls-Mantey et al. (Aug. 2012) "Antibody-Dependent Cellular Cytotoxicity against Primary HIV-Infected CD4(+) T Cells Is Directly Associated with the Magnitude of Surface IgG Binding", Journal of Virology, 86(16):8672-8680.

Sun et al. (May 13, 2015) "Anti-CD20/CD3 T cell-dependent bispecific antibody for the treatment of B cell malignancies", Science translational medicine, 7(287): (287ra70):11 pages.

Thaventhiran et al. (2012) "T Cell Co-Inhibitory Receptors: Functions and Signalling Mechanisms", Journal of Clinical & Cellular Immunology, S12:12 pages.

Tomalia (1993) "Starburst/Cascade Dendrimers: Fundamental Building Blocks for a New Nanoscopic Chemistry Set", Aldrichimica Acta, 26(4):89-101.

Urlaub et al. (Jul. 1980) "Isolation of Chinese Hamster Cell Mutants Deficient in Dihydrofolate Reductase Activity", PNAS, 77(7):4216-4220.

Wahl et al. (1987) "Molecular Hybridization of Immobilized Nucleic Acids: Theoretical Concepts and Practical Considerations", Methods in Enzymology, 152:399-407.

Waldmann (Aug. 2006) "The Biology of Interleukin-2 and Interleukin-15: Implications for Cancer Therapy and Vaccine Design", Nature Reviews Immunology, 6(8):595-601.

Wang et al. (Jul. 2015) "NK Cell-Mediated Antibody-Dependent Cellular Cytotoxicity in Cancer Immunotherapy", Frontiers in immunology, 6(368):15 pages.

Weidle et al. (2013) "The Emerging Role of New Protein Scaffold-based Agents for Treatment of Cancer", Cancer Genomics and Proteomics, 10(4):155-168.

Whitlow et al. (Apr. 1991) "Single-Chain Fv Proteins and their Fusion Proteins", Methods: A Companion to Methods in Enzymology, 2(2):97-105.

Wong et al. (2011; e-published on Dec. 21, 2010) "Interleukin-15:Interleukin-15 Receptor α Scaffold for Creation of Multivalent Targeted Immune Molecules", Protein Engineering, Design & Selection, 24(4):373-383.

Wong et al. (Nov. 1, 2013) "The IL-15-based superagonist ALT-803 promotes the antigen-independent conversion of memory CD8+ T cells into innate-like effector cells with antitumor activity", Oncoimmunology, 2(11): (e26442): 3 pages.

Xu et al. (May 15, 2013) "Efficacy and Mechanism-of-Action of a Novel Superagonist Interleukin-15: Interleukin-15 Receptor α/Fc Fusion Complex in Syngeneic Murine Models of Multiple Myeloma", Cancer Research, 73(10):3075-3086.

Xuan et al. (Apr. 8, 2010) "Targeted Delivery of Interferon-Alpha via Fusion to Anti-CD20 Results in Potent Antitumor Activity against B-Cell Lymphoma", Blood, 115(14):2864-2871.

Zhu et al. (Sep. 15, 2009) "Novel Human Interleukin-15 Agonists", Journal of Immunology, 183(6):3598-3607.

Zhu et al. (Apr. 13, 2015) "Synergistic Innate and Adaptive Immune Response to Combination Immunotherapy with Anti-Tumor Antigen Antibodies and Extended Serum Half-Life IL-2", Cancer Cell, 27(4):489-501.

\* cited by examiner

FIG. 5A
FIG. 5B
FIG. 5C
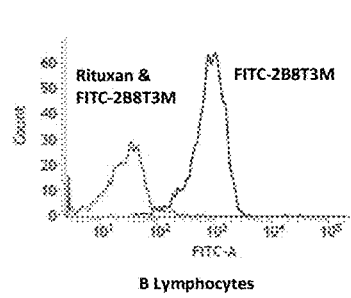
B Lymphocytes
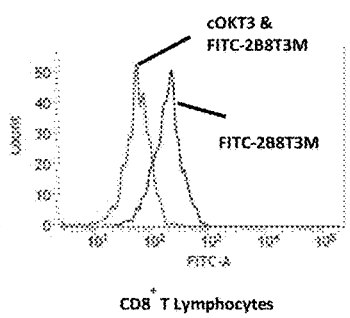
CD8⁺ T Lymphocytes
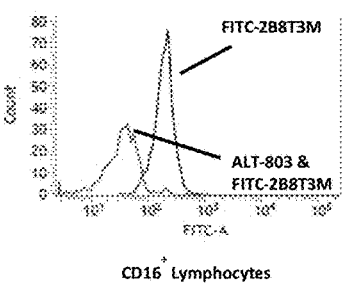
CD16⁺ Lymphocytes

A

B

CONSTRUCTION AND CHARACTERIZATION OF MULTIMERIC IL-15-BASED MOLECULES WITH CD3 BINDING DOMAINS

RELATED APPLICATIONS

This application claims the benefit of priority under 35 U.S.C. § 119(e) of U.S. Provisional Application No. 62/397, 236, filed on Sep. 20, 2016 and U.S. Provisional Application No. 62/342,311, filed on May 27, 2016, both of which applications are incorporated herein by reference in their entireties.

FIELD OF THE INVENTION

This invention relates generally to the field of multimeric fusion molecules.

BACKGROUND OF THE INVENTION

Prior to the invention described herein, there was a pressing need to develop new strategies to target various effector molecules to a disease site to provide therapeutic benefit without the side effects associated with non-specific immune activity.

SUMMARY OF THE INVENTION

The invention is based, at least in part, on the surprising discovery that multispecific proteins activate effector T cells and natural killer (NK) cells and target their activity against disease cells, thereby resulting in disease-specific cytotoxicity. Provided herein are multispecific proteins with one binding domain that recognizes disease antigens and a second binding domain that recognizes CD3 on T cells. Exemplary disease antigens are associated with neoplasia, infectious disease, or autoimmune disease. Specifically, described herein is a protein complex comprising an anti-CD3 scAb/huIL-15N72D fusion protein and an anti-CD20 scAb/huIL-15RαSu/huIgG1 Fc fusion protein. This complex recognizes B cell lymphomas via the anti-CD20 scAb domain, induces NK and T cell responses via IL-15 activity, activates T cell responses via the anti-CD3 scAb domain, and stimulates antibody-dependent cell-mediated cytotoxicity (ADCC) and complement-dependent cytotoxicity (CDC) via the Fc binding domain.

Provided is an isolated soluble fusion protein complex comprising at least two soluble fusion proteins. For example, the first fusion protein comprises a first binding domain covalently linked to an interleukin-15 (IL-15) polypeptide. The second fusion protein comprises a second binding domain that recognizes disease antigens, wherein this domain is covalently linked to a soluble IL-15 receptor alpha sushi-binding domain (IL-15RαSu) fused to an immunoglobulin Fc domain. One of the first or second binding domains comprises an anti-CD3 antibody and the other binding domain comprises an antigen-specific binding domain. Exemplary antigen-specific binding domains of a fusion protein include an anti-CD20 antibody. For example, a second fusion protein comprises an anti-CD20 antibody covalently linked to an IL-15RαSu/Fc fusion. The IL-15 domain of the first fusion protein binds to the soluble IL-15RαSu domain of the second fusion protein to form a soluble fusion protein complex. Alternatively, the first fusion protein comprises an anti-CD3 antibody covalently linked to a soluble IL-15 receptor alpha sushi-binding domain (IL-15RαSu) fused to an immunoglobulin Fc domain whereas the second fusion protein comprises a binding domain that recognizes disease antigens covalently linked and a variant interleukin-15 (IL-15) polypeptide. In some cases, the IL-15 polypeptide comprises an IL-15 variant comprising an N72D mutation (IL-15N72D).

In some cases, the anti-CD3 antibody comprises a single chain antibody wherein an immunoglobulin light chain variable domain covalently linked to an immunoglobulin heavy chain variable domain by a polypeptide linker sequence. Similarly, in some cases, the binding domain, e.g., an anti-CD-20 antibody, that recognizes disease antigens is a single-chain antibody comprising an immunoglobulin light chain variable domain covalently linked to an immunoglobulin heavy chain variable domain by a polypeptide linker sequence.

An exemplary first fusion protein comprises the amino acid sequence set forth in SEQ ID NO: 2. An exemplary second fusion protein comprises the amino acid sequence set forth in SEQ ID NO: 4. An exemplary nucleic acid sequence encoding the first fusion protein comprises the sequence set forth in SEQ ID NO: 1. An exemplary nucleic acid sequence encoding the second fusion protein comprises the sequence set forth in SEQ ID NO: 3. In one aspect, the nucleic acid sequence(s) further comprises a promoter, translation initiation signal, and leader sequence operably linked to the sequence encoding the fusion protein.

Also provided are DNA vector(s) comprising the nucleic acid sequences described herein. For example, the nucleic acid sequence is in a vector for replication, expression, or both.

Also provided is a soluble fusion protein complex comprising a first soluble fusion protein complex covalently linked to a second soluble fusion protein complex. For example, the soluble fusion protein complexes of the invention are multimerized, e.g., dimerized, trimerized, or otherwise multimerized (e.g., 4 complexes, 5 complexes, etc.). For example, the multimers are homomultimers or heteromultimers. The soluble fusion protein complexes are joined by covalent bonds, e.g., disulfide bonds, chemical cross-linking agents. In some cases, one soluble fusion protein is covalently linked to another soluble fusion protein by a disulfide bond linking the Fc domain of the first soluble fusion protein to the Fc domain of the second soluble fusion protein.

The Fc domain or functional fragment thereof includes an Fc domain selected from the group consisting of IgG Fc domain, human IgG1 Fc domain, human IgG2 Fc domain, human IgG3 Fc domain, human IgG4 Fc domain, IgA Fc domain, IgD Fc domain, IgE Fc domain, and IgM Fc domain; or any combination thereof. Optionally, the Fc domain includes an amino acid change that results in an Fc domain with altered complement or Fc receptor binding properties or altered dimerization or glycosylation profiles Amino acid changes to produce an Fc domain with altered complement or Fc receptor binding properties or altered dimerization or glycosylation profiles are known in the art. For example, a substitution of leucine residues at positions 234 and 235 of the IgG1 CH2 (numbering based on antibody consensus sequence) (i.e., . . . P E L L G G . . . ) with alanine residues (i.e., . . . P E A A G G . . . ) results in a loss of Fc gamma receptor binding, whereas the substitution of the lysine residue at position 322 of the IgG1 CH2 (numbering based on antibody consensus sequence) (i.e., . . . K C K S L . . . ) with an alanine residue (i.e., . . . K C A S L . . . ) results in a loss of complement activation. In some examples, such mutations are combined.

In some aspects, the first biologically active polypeptide is covalently linked to an IL-15 polypeptide (or functional fragment thereof) by a polypeptide linker sequence. Similarly, the second biologically active polypeptide is covalently linked to an IL-15Rα polypeptide (or functional fragment thereof) by polypeptide linker sequence. Optionally, the IL-15Rα polypeptide (or functional fragment thereof) is covalently linked to the Fc domain (or functional fragment thereof) by polypeptide linker sequence. Each polypeptide linker sequence can be selected independently. Optionally, the polypeptide linker sequences are the same. Alternatively, they are different.

Optionally, the soluble fusion protein complexes of the invention are provided wherein at least one of the soluble fusion proteins comprise a detectable label. Detectable labels include, but are not limited to, biotin, streptavidin, an enzyme or catalytically active fragment thereof, a radionuclide, a nanoparticle, a paramagnetic metal ion, or a fluorescent, phosphorescent, or chemiluminescent molecule, or any combination thereof.

The invention provides method for making the soluble fusion protein complexes of the invention. The method includes the steps of: a) introducing into a first host cell a DNA vector with appropriate control sequences encoding the first fusion protein, b) culturing the first host cell in media under conditions sufficient to express the first fusion protein in the cell or the media; c) purifying the first fusion protein from the host cells or media, d) introducing into a second host cell a DNA vector with appropriate control sequences encoding the second fusion protein, e) culturing the second host cell in media under conditions sufficient to express the second fusion protein in the cell or the media; and f) purifying the second fusion protein from the host cells or media, and g) mixing the first and second fusion proteins under conditions sufficient to allow binding between IL-15 domain of a first fusion protein and the soluble IL-15Rα domain of a second fusion protein to form the soluble fusion protein complex.

In some cases, the method further includes mixing the first and second fusion protein under conditions sufficient to allow formation of a disulfide bond between the polypeptides expressed from the expression vectors.

Alternatively, methods for making soluble fusion protein complexes of the invention are carried out by a) introducing into a host cell a DNA vector with appropriate control sequences encoding the first fusion protein and a DNA vector with appropriate control sequences encoding the second fusion protein, b) culturing the host cell in media under conditions sufficient to express the fusion proteins in the cell or the media and allow association between IL-15 domain of a first fusion protein and the soluble IL-15Rα domain of a second fusion protein to form the soluble fusion protein complex; and c) purifying the soluble fusion protein complex from the host cells or media.

In one aspect, the method further includes mixing the first and second fusion protein under conditions sufficient to allow formation of a disulfide bond between the polypeptides expressed from the expression vectors.

Also provided are methods for making soluble fusion protein complexes comprising a) introducing into a host cell a DNA vector with appropriate control sequences encoding the first and second fusion proteins, b) culturing the host cell in media under conditions sufficient to express the fusion proteins in the cell or the media and allow association between IL-15 domain of a first fusion protein and the soluble IL-15Rα domain of a second fusion protein to form the soluble fusion protein complex, and to allow formation of a disulfide bond between the polypeptides; and c) purifying the soluble fusion protein complex from the host cells or media.

Optionally, the method further includes mixing the first and second fusion protein under conditions sufficient to allow formation of a disulfide bond between the polypeptides expressed from the expression vectors.

Methods for treating a neoplasia, infectious disease or autoimmune disease in a subject in need thereof are carried out by administering to a subject an effective amount of a pharmaceutical composition comprising a soluble anti-CD3 scAb/IL-15N72D: disease antigen-specific scAb/IL-15RαSu/Fc fusion protein complex, thereby treating the neoplasia, infectious disease or autoimmune disease. For example, methods for treating B cell lymphoma or B cell-mediated autoimmune disease in a subject in need thereof are carried out by administering to a subject an effective amount of a pharmaceutical composition comprising a soluble anti-CD3 scAb/huIL-15N72D:anti-CD20 scAb/huIL-15RαSu/huIgG1 Fc fusion protein complex (2B8T3M), thereby treating the lymphoma or autoimmune disease. An exemplary anti-CD3 scAb/huIL-15N72D comprises the amino acid sequence set forth in SEQ ID NO: 2. An exemplary anti-CD20 scAb/huAIL-15RαSu/huIgG1 Fc comprises the amino acid sequence set forth in SEQ ID NO: 4. Preferably, the fusion protein complex induces an immune response in the subject.

Suitable neoplasias for treatment with the methods described herein include a glioblastoma, prostate cancer, hematological cancer, acute myeloid leukemia, B-cell neoplasm, multiple myeloma, B-cell lymphoma, B-cell non-Hodgkin's lymphoma, Hodgkin's lymphoma, chronic lymphocytic leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, pancreatic cancer, head and neck cancer, colorectal cancer, and ovarian cancer, non-small cell lung carcinoma, and squamous cell head and neck carcinoma. An exemplary infection for treatment using the methods described herein is infection with human immunodeficiency virus (HIV). The methods described herein are also useful to treat bacterial infections (e.g., gram positive or gram negative bacteria) (Oleksiewicz et al. 2012. Arch Biochem Biophys. 526:124-31). An exemplary autoimmune disease for treatment using the methods described herein is an autoimmune disease mediated by B cells. Such autoimmune diseases include rheumatoid arthritis, multiple sclerosis, idiopathic thrombocytopaenia, IgM-mediated polyneuropathy, Factor VIII deficiency, systemic lupus erythematosus, Sjögren's syndrome, inflammatory myositis, pemphigus vulgaris, neuromyelitis optica, ANCA-associated vasculitis, chronic inflammatory demyelinating polyneuropathy, autoimmune anemias, pure red cell aplasia, thrombotic thrombocytopenic purpura (TTP), idiopathic thrombocytopenic purpura (ITP), Evans syndrome, vasculitis (for example granulomatosis with polyangiitis, formerly Wegener's), bullous skin disorders (for example pemphigus, pemphigoid), type 1 diabetes mellitus, anti-NMDA receptor encephalitis and Devic's disease, Graves' ophthalmopathy, autoimmune pancreatitis, Opsoclonus myoclonus syndrome (OMS), and IgG4-related disease.

The pharmaceutical composition comprising a fusion protein is administered in an effective amount. For example, an effective amount of the pharmaceutical composition is between about 1 µg/kg and 100 µg/kg, e.g., 1, 5, 10, 15, 20, 25, 30, 35, 40, 45, 50, 55, 60, 65, 70, 75, 80, 85, 90, 95, or 100 µg/kg. Alternatively, ALT-803 is administered as a fixed dose or based on body surface area (i.e., per m²).

The pharmaceutical composition comprising the fusion protein complex is administered at least one time per month, e.g., twice per month, once per week, twice per week, once per day, twice per day, every 8 hours, every 4 hours, every 2 hours, or every hour. Suitable modes of administration for the pharmaceutical composition include systemic administration, intravenous administration, subcutaneous administration, intramuscular administration, intratumoral administration, inhalation, and intraperitoneal administration.

Preferably, the fusion protein increases serum levels of interferon gamma (IFN-γ), and/or stimulates CD4⁺ and CD8⁺ T cells and NK cells to kill diseased cells or tumor cells in a subject. For example, the fusion protein complex stimulates CD4⁺ and CD8⁺ T cell responses against cels associated with said neoplasia, infectious disease, or autoimmune disease.

In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15RβγC receptors compared to the native IL-15 polypeptide. Alternatively, the IL-15 variant functions as an IL-15 antagonist as demonstrated by e.g., decreased binding activity for the IL-15RβγC receptors compared to the native IL-15 polypeptide.

Methods for killing a target cell are carried out by a) contacting a plurality of cells with a soluble fusion protein complex of the invention, wherein the plurality of cells further include immune cells bearing CD3 recognized by an anti-CD3 antibody, e.g., an anti-CD3 single chain antibody, and the IL-15R chains recognized by the IL-15 domain, or immune cells bearing Fc receptor chains recognized by the Fc domain, and the target disease cells bearing an antigen recognized by binding domain such as an antigen-specific scAb, b) forming a specific binding complex (bridge) between the antigen on the target disease cells and CD3, the IL-15R or Fc receptor chains on the immune cells sufficient to bind and activate the immune cells; and c) killing the target disease cells by the bound activated immune cells. For example, the target disease cells are tumor cells, autoimmune disease-associated cells, e.g., autoimmune B cells, or infected cells, e.g., virally infected cells. For example, the antigen-specific binding domain comprises an anti-CD-20 antibody.

Also provided are methods for preventing or treating disease in a patient in which the diseased cells express a disease associated antigen, the method including the steps of: a) administering to the patient a soluble fusion protein complex of the invention having a disease antigen-specific binding domain such as a scAb; b) forming a specific binding complex (bridge) between antigen-expressing diseased cells and CD3, IL-15R or Fc receptor expressing immune cells sufficient to localize the immune cells; and c) damaging or killing the disease cells sufficient to prevent or treat the disease in the patient.

The invention also provides methods for preventing or treating disease in a patient in which the diseased cells express a disease associated antigen, the method including the steps of: a) mixing immune cells bearing CD3, IL-15R chains or Fc receptor chains with a soluble fusion protein complex of the invention comprising disease antigen-specific binding domain, b) administering to the patient the immune cell-fusion protein complex mixture; c) forming a specific binding complex (bridge) between antigen-expressing diseased cells and CD3, IL-15R or Fc receptor expressing immune cells sufficient to localize the immune cells; and d) damaging or killing the disease cells sufficient to prevent or treat the disease in the patient.

The invention provides methods of stimulating immune responses in a mammal by administering to the mammal an effective amount of the soluble fusion protein complex of the invention. The invention also provides methods of suppressing immune responses in a mammal by administering to the mammal an effective amount of the soluble fusion protein complex of any one of the invention.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound. An exemplary therapeutic agent is 2B8T3M.

By "2B8T3M" is meant a complex comprising an anti-CD3 scAb/huIL-15N72D and an anti-CD20 scAb/huIL-15RαSu/huIgG1 Fc.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "binding domain" or "antigen-specific binding domain" is intended to encompass an antibody, single chain antibody, Fab, Fv, T-cell receptor binding domain, ligand binding domain, receptor binding domain, or other antigen-specific polypeptides known in the art.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')$_2$, Fab', Fab, Fv) capable of binding the epitope, antigen or antigenic fragment of interest.

By "binding to" a molecule is meant having a physicochemical affinity for that molecule.

"Detect" refers to identifying the presence, absence or amount of the analyte to be detected.

By "disease" is meant any condition or disorder that damages or interferes with the normal function of a cell, tissue, or organ. Examples of diseases include neoplasias, autoimmune diseases and viral infections.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5,000, about 3,000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated", "purified", or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilms tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma. As used herein, "obtaining" as in "obtaining an agent" includes synthesizing, purchasing, or otherwise acquiring the agent.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequencher, Gene Codes Corporation, 775 Technology Drive, Ann Arbor, Mich.; Vector NTI, Life Technologies, 3175 Staley Rd. Grand Island, N.Y.). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 5A is a line graph showing the binding activity of 2B8T3M to CD20-bearing human lymphocytes. FIG. 5B is a line graph showing the binding activity of 2B8T3M to CD3-bearing human lymphocytes. FIG. 5C is a line graph showing the binding activity of 2B8T3M to IL-15-receptor-bearing human lymphocytes.

FIG. 9A is a schematic diagram of the 2B8T2M complex in cluding the organization of the single chain components of 2B8. FIG. 9B is an SDS-PAGE analysis of purified 2B8T2M fusion protein under reducing conditions. Lanes: (1) MW marker, (2) 2B8T2M. FIG. 9C shows size exclusion chromatography analysis of 2B8T2M protein.

FIG. 10C is a graph wherein human histiocytic lymphoma U-937 cells were stained with FITC-conjugated rituximab, 2B8T2M, or 2B8T2M-LA mutant for 30 minutes and then analyzed for Fc-receptor binding activity by flow cytometry.

FIG. 11A is a graph wherein Daudi cells ($3 \times 10^5$/test) were incubated with various concentration of 2B8T2M, 2B8T2M-LA mutant, 2B8T2M-D8N mutant, and rituximab as a positive control at 37° C. for 2 hours in the presence of complement (normal human serum). Propidium iodide was added and analyzed by flow cytometry. The percentage of dead cells indicates propidium iodide-positive cells percentage. (n=3). FIG. 11B is a graph wherein Daudi cells were incubated with 2B8T2M, 2B8T2M-LA, 2B8T2M-D8N, or rituximab at 37° C. for 3 days. Daudi cells were stained with Annexin V and the percentage of cell death was determined by flow cytometry. Data represent the mean±SE.

FIG. 12C-FIG. 12D are graphs wherein human PBMCs ($5 \times 10^6$) were incubated in 2 mL of RPMI-10 with 2B8T2M for 2 days. The 2B8T2M activated PBMCs were stained with anti-NKp46 (FIG. 12C, NK cells) or anti-CD8 (FIG. 12D, CD8$^+$ T cells) followed by intracellular granzyme B and perforin staining. Expression levels of granzyme B and perform by the activated CD8$^+$ T cells and NK cells were determined by flow cytometry.

FIG. 13A and FIG. 13D show serial two-dimensional projection PET images at different time points post-injection of $^{64}$Cu-NOTA-2B8T2M and $^{64}$Cu-NOTA-rituximab (0.5, 6, 30, and 70 hours). FIG. 13B and FIG. 13E are graphs wherein region-of-interest analysis to calculate the percentage injected dose per gram of tissue (% ID/g) for major organs was conducted at the various time points based on the PET imaging data. FIG. 13C and FIG. 13F are graphs wherein the mice were euthanized and major organs/tissues were collected and weighed. The tissue biodistribution of 2B8T2M and rituximab was determined using a gamma-counter. Data are representative of 4 mice per group (mean±SD).

FIG. 14A-FIG. 14B, spleen cells harvested on day 5 were stained with anti-CD4, anti-CD8 for T cells (FIG. 14A), and with anti-NK1.1 for NK cells (FIG. 14B) to be analyzed by flow cytometry. FIG. 14C is a graph wherein cell division is shown based on fluorescent intensity of CellTrace Violet (No proliferation is indicated by brightest cells). FIG. 14D is a graph wherein the percentage of proliferative cells was analyzed by flow cytometry. $p>0.05$: IL-15 vs 2B8T2M-D8N and 2B8T2M vs 2B8T2M-LA; $p<0.01$ among other groups. Data represent the mean±SD.

FIG. 15A is a graph wherein following i.v. injection with $1 \times 10^7$ Daudi cells/mouse, Daudi B-lymphoma bearing mice were randomized into 3 treatment groups (n=6) and treated with rituximab (▲) at 10 mg/kg, 2B8T2M (●) at 5 mg/kg, and PBS (■) vehicle control 15 days and 18 days post-inoculation. PBS vs rituximab: $p=0.001$; rituximab vs 2B8T2M: $p=0.006$. FIG. 15B-FIG. 15D are graphs wherein Daudi B-lymphoma bearing mice were randomized into treatment groups and treated with rituximab (n=7) at 10 mg/kg, 2B8T2M at 0.2, 1, 5, 12.8 mg/kg (n=6/dose level), and PBS (n=7) vehicle control as in FIG. 15A. Mice were euthanized and bone marrow and spleen cells were harvested 4 days post-second treatment. FIG. 15B is a graph wherein the percentage of Daudi cells in the bone marrow was determined by HLA-DR staining using flow cytometry. FIG. 15C is a graph wherein the percentage of NK cells in the spleen was determined by NKp46 staining using flow cytometry. FIG. 15D is a graph wherein the percentage of NK cells in the bone marrow was determined by NKp46 staining using flow cytometry. FIG. 15E is a graph wherein Daudi B-lymphoma bearing SCID-beige mice were randomized into 3 treatment groups and treated with rituximab (n=8) at 10 mg/kg, 2B8T2M at 5 mg/kg (n=7) and PBS (n=8) vehicle control 13 days and 16 days post-inoculation. Mice were euthanized and bone marrow cells were harvested 4 days post-second treatment. The percentage of Daudi cells in the bone marrow was determined by HLA-DR staining using flow cytometry. Data represent the mean±SD. FIG. 15B-FIG. 15E, * indicates $p<0.01$ compared to PBS; † indicates $p<0.01$ compared to rituximab.

FIG. 16A is a graph wherein following i.v. injection with 1×107 Daudi cells/mouse, Daudi B-lymphoma bearing SCID mice were randomized into 4 treatment groups (n=8) and treated with 5 mg/kg of 2B8T2M, 2B8T2M-LA, 2B8T2M-D8N, and PBS as vehicle control as in FIG. 15. Mice were euthanized and bone marrow cells were harvested 4 days post-second treatment. The percentage of Daudi cells in the bone marrow was determined as in FIG. 15. FIG. 16B is a graph wherein Daudi B-lymphoma bearing SCID mice were randomized into 2 treatment groups (n=10) and treated with 5 mg/kg of 2B8T2M, and c264scTCR-IL15N72D/C264scTCR-IL15RαSuFc at 18 days and 21 days post-inoculation. All mice were euthanized and bone marrow cells were harvested 4 days post-second treatment. The percentage of Daudi cells in the bone marrow was determined as in FIG. 15. * indicates p<0.01 compared to PBS; § indicates p<0.05 compared to 2B8T2M. Data represent the mean±SD.

DETAILED DESCRIPTION

Figure 1:
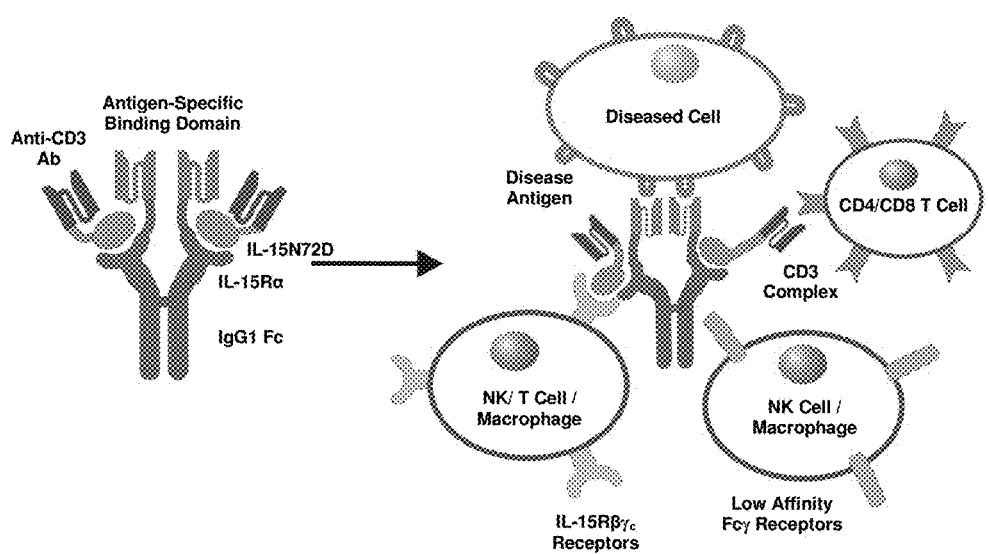
FIG. 1 is a schematic diagram illustrating the T3 molecule (T3M), a multichain fusion polypeptide, and its immune-mediated effects against disease cells.

The invention is based, at least in part, on the surprising discovery that multispecific protein complexes activate effector T cells and target their activity against disease cells, thereby resulting in disease-specific cytotoxicity. Provided herein are multispecific protein complexes with one binding domain that recognizes disease antigens (e.g., CD20) and a second binding domain that recognizes CD3 on T cells. Such protein complexes have utility in methods for treating a neoplasia, infectious disease or autoimmune disease in a subject (FIG. 1). Specifically, as described in detail below, a soluble anti-CD3 scAb/huIL-15N72D:anti-CD20 scAb/huIL-15RαSu/huIgG1 Fc complex ("anti-CD3 scAb-anti-CD20 scAb T3M" or "2B8T3M") stimulated CD8+ and CD4+ T cells to kill tumor target cells (FIG. 2). 2B8T3M also stimulated the release of interferon-γ (IFN-γ) from human peripheral blood mononuclear cells (PBMCs), and CD8+ and CD4+ T cells. Thus, provided herein are compositions featuring 2B8T3M and methods of using such compositions to enhance an immune response against a neoplasia (e.g., B cell lymphoma and chronic lymphocytic leukemia) and to deplete B cells to treat autoimmune diseases (e.g., immune and thrombotic thrombocytopenic purpura and rheumatoid arthritis).

As described herein, the use of proteins with the capability of targeting diseased cells for host immune recognition and response is an effective strategy for treating cancer, infectious diseases and autoimmune diseases. As described in U.S. Pat. No. 8,507,222 (incorporated herein by reference), a protein scaffold comprising IL-15 and IL-15 receptor α domains has been used to generate multispecific proteins capable of recognizing antigens on disease cells and receptors on immune cells. See, U.S. Pat. No. 8,507,222 at Example 15. Described herein is the generation of soluble multispecific protein complexes comprising IL-15 and IL-15 receptor α linked to binding domains recognizing disease-associated antigens and CD3. For example, the antigen-specific binding domain is a single chain antibody (scAb) that recognizes human CD20 on B cell lymphomas and the CD3 recognition domain is a scAb specific to human CD3.

In some cases, the anti-CD20 scAb is derived from the variable chains of rituximab, a chimeric monoclonal anti-CD20 antibody. For example, the anti-CD20 scAb sequence comprises the coding regions of the heavy and light chain V domains of the rituximab antibody linked via a flexible linker sequence. Alternatively, binding domains from other anti-CD20 Abs known in the art could be used.

In some cases the anti-CD3 scAb is derived from the variable chains of OKT3, a murine monoclonal anti-CD3 antibody. For example, the anti-human CD3 scAb sequence comprises the coding regions of the heavy and light chain V domains of the OKT3 antibody linked via a flexible linker sequence. Alternatively, binding domains from other anti-CD3 Abs known in the art could be used.

The binding domains recognizing disease antigens and CD3 are linked to either the N- or C-termini of the IL-15 or IL-15 receptor α proteins with or without an additional linker sequence so long as binding activity is maintained. Preferably, the anti-CD3 scAb domain is linked to the N-terminus of the human IL-15N72D superagonist protein (huIL-15N72D). Alternatively, the anti-CD3 scAb domain is linked to the C-terminus of the human IL-15N72D protein. Preferably, the antigen-specific binding domain is linked to the N-terminus of the human IL-15 receptor α sushi domain (huIL-15RαSu). In some cases, the multispecific protein complexes of the invention further comprise an IgG Fc domain for protein dimerization and recognition of CD16 receptors on immune cells. Such a domain mediates stimulation of antibody-dependent cellular cytotoxicity (ADCC) and complement-dependent cytotoxicity (CDC) against target cells. In some examples, it is useful to employ Fc domains with enhanced or decreased CD16 binding activity. In one aspect, the Fc domain contains amino acid substitutions L234A and L235A (LALA) (number based on Fc consensus sequence) that reduce ADCC activity, but retain the ability to form disulfide-bound dimers.

Interleukin-15

Interleukin-15 (IL-15) is an important cytokine for the development, proliferation, and activation of effector NK cells and CD8+ memory T cells. IL-15 binds to the IL-15 receptor α (IL-15Rα) and is presented in trans to the IL-2/IL-15 receptor β—common γ chain (IL-15Rβγ$_c$) complex on effector cells. IL-15 and IL-2 share binding to the IL-15Rβγ$_c$, and signal through STAT3 and STAT5 pathways. However, unlike IL-2, IL-15 does not support maintenance of CD4+CD25+FoxP3+ regulatory T (Treg) cells or induce cell death of activated CD8+ T cells, effects that may have limited the therapeutic activity of IL-2 against multiple myeloma. Additionally, IL-15 is the only cytokine known to provide anti-apoptotic signaling to effector CD8+ T cells. IL-15, either administered alone or as a complex with the IL-15Rα, exhibits potent anti-tumor activities against well-established solid tumors in experimental animal models and, thus, has been identified as one of the most promising immunotherapeutic drugs that could potentially cure cancer.

To facilitate clinical development of an IL-15-based cancer therapeutic, an IL-15 mutant (IL-15N72D) with increased biological activity compared to IL-15 was identified (Zhu et al., J Immunol, 183: 3598-3607, 2009). The pharmacokinetics and biological activity of this IL-15 superagonist (IL-15N72D) was further improved by the creation of IL-15N72D:IL-15Rα/Fc fusion complex (ALT-803), such that the super agonist complex has at least 25-times the activity of the native cytokine in vivo (Han et al., Cytokine, 56: 804-810, 2011).

Antigen-Specific Binding Domains

Antigen-specific binding domains consist of polypeptides that specifically bind to targets on diseased cells. Alternatively, these domains may bind to targets on other cells that support the diseased state, such as targets on stromal cells that support tumor growth or targets on immune cells that support disease-mediated immunosuppression. Antigen-specific binding domains include antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins (Weidle, U H, et al. 2013. Cancer Genomics & Proteomics 10: 155-168)) known in the art.

In certain embodiments, the antigen for the antigen-specific binding domain comprises a cell surface receptor or ligand. In a further embodiment, the antigen comprises a CD antigen, cytokine or chemokine receptor or ligand, growth factor receptor or ligand, tissue factor, cell adhesion molecule, MHC/MHC-like molecules, Fc receptor, Toll-like receptor, NK receptor, TCR, BCR, positive/negative co-stimulatory receptor or ligand, death receptor or ligand, tumor associated antigen, or virus encoded antigen.

Preferably, the antigen-specific binding domain is capable of binding to an antigen on a tumor cell. Tumor-specific binding domain may be derived from antibodies approved for treatment of patients with cancer include rituximab, ofatumumab, and obinutuzumab (anti-CD20 Abs); trastuzumab and pertuzumab (anti-HER2 Abs); cetuximab and panitumumab (anti-EGFR Abs); and alemtuzumab (anti-CD52 Ab). Similarly, binding domains from approved antibody-effector molecule conjugates specific to CD20 ($^{90}$Y-labeled ibritumomab tiuxetan, $^{131}$I-labeled tositumomab), HER2 (ado-trastuzumab emtansine), CD30 (brentuximab vedotin) and CD33 (gemtuzumab ozogamicin) (Sliwkowski M X, Mellman I. 2013 Science 341:1192) could be used.

Additionally, preferred binding domains of the invention may include various other tumor-specific antibody domains known in the art. The antibodies and their respective targets for treatment of cancer include but are not limited to nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch.14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-5AC), epitumomab cituxetan (anti-episialin), epratuzumab (anti-CD22), ertumaxomab (anti-HER2/neu, CD3), etaracizumab (anti-integrin αvβ3), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1(glycoprotein 75)), fresolimumab (anti-TGF β), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSF1R), IMC-TR1 (TGFβRII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor α-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-R α), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin $\alpha 5\beta 1$), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), and GDC-0199 (anti-Bcl-2).

Other antibody domains or tumor target binding proteins useful in the invention (e.g. TCR domains) include, but are not limited to, those that bind the following antigens (note, the cancer indications indicated represent non-limiting examples): aminopeptidase N (CD13), annexin A1, B7-H3 (CD276, various cancers), CA125 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma, B-cell neoplasmas, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD22? (breast, ovarian cancers), CD262 (NSCLC and other cancers), CD309 (ovarian cancers), CD326 (solid tumors), CEACAM3 (colorectal, gastric cancers), CEACAMS (CEA, CD66e) (breast, colorectal and lung cancers), DLL4 (A-like-4), EGFR (various cancers), CTLA4 (melanoma), CXCR4 (CD 184, heme-oncology, solid tumors), Endoglin (CD 105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR10 (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins ($\alpha v\beta 3$, $\alpha 5\beta 1$, $\alpha 6\beta 4$, $\alpha 11\beta 3$, $\alpha 5\beta 5$, $\alpha v\beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumour associated glycoprotein 72, AML, gastric, colorectal, ovarian cancers), T cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178: 1975-9). Examples of these antigens include Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvIII, HER-2/neu, idiotype, MAGE A3, p53 nonmutant, NY-ESO-1, GD2, CEA, MelanA/MART1, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B 1, polysialic acid, MYCN, RhoC, TRP-2, GD3, fucosyl GM1, mesothelin, PSCA, MAGE A1, sLe(a), CYPIB I, PLAC1, GM3, BORIS, Tn, GloboH, ETV6-AML, NY-BR-1, RGS5, SART3, STn, carbonic anhydrase IX, PAXS, OY-TES1, sperm protein 17, LCK, HMWMAA, AKAP-4, SSX2, XAGE 1, B7H3, legumain, Tie 2, Page4, VEGFR2, MAD-CT-1, FAP, PDGFR-$\beta$, MAD-CT-2, and Fos-related antigen 1.

Additionally, preferred binding domains of the invention include those specific to antigens and epitope targets associated with infected cells that are known in the art. Such targets include but are not limited those derived from the following infectious agents are of interest: HIV virus (particularly antigens derived from the HIV envelope spike and/or gp120 and gp41 epitopes), Human papilloma virus (HPV), *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, —influenzae B, Treponema pallidum*, Lyme disease spirochetes, *Pseudomonas aeruginosa, Mycobacterium leprae, Brucella abortus*, rabies virus, influenza virus, *cytomegalovirus*, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*.

In other embodiments, the binding domain is specific to an immune checkpoint molecule or its ligand and acts as an inhibitor of immune checkpoint suppressive activity or as an agonist of immune checkpoint stimulatory activity. Such immune checkpoint molecules and ligands include PD1, PDL1, PDL2, CTLA4, CD28, CD80, CD86, B7-H3, B7-H4, B7-H5, ICOS-L, ICOS, BTLA, CD137L, CD137, HVEM, KIR, 4-1BB, OX40L, CD70, CD27, OX40, GITR, IDO, TIM3, GALS, VISTA, CD155, TIGIT, LIGHT, LAIR-1, Siglecs and A2aR (Pardoll D M. 2012. Nature Rev Cancer 12:252-264, Thaventhiran T, et al. 2012. J Clin Cell Immunol S12:004). Additionally, preferred antibody domains of the invention may include ipilimumab and tremelimumab (anti-CTLA4). nivolumab, pembrolizumab, pidilizumab, TSR-042, ANB011, AMP-514 and AMP-224 (a ligand-Fc fusion) (anti-PD1), MPDL3280A, MEDI4736, MEDI0680, and BMS-9365569 (anti-PDL1), MEDI6469 (anti-OX40 agonist), BMS-986016, IMP701, IMP731, and IMP321 (anti-LAGS).

T-Cell Receptors (TCRs)

T-cells are a subgroup of cells which together with other immune cell types (polymorphonuclear cells, eosinophils, basophils, mast cells, B-cells, NK cells), constitute the cellular component of the immune system. Under physiological conditions, T-cells function in immune surveillance and in the elimination of foreign antigen. However, under pathological conditions, there is compelling evidence that T-cells play a major role in the causation and propagation of disease. In these disorders, breakdown of T-cell immunological tolerance, either central or peripheral is a fundamental process in the causation of autoimmune disease.

The TCR complex is composed of at least seven transmembrane proteins. The disulfide-linked ($\alpha\beta$ or $\gamma\delta$) heterodimer forms the monotypic antigen recognition unit, while the invariant chains of CD3, consisting of $\epsilon$, $\gamma$, $\delta$, $\zeta$, and $\eta$ chains, are responsible for coupling the ligand binding to signaling pathways that result in T-cell activation and the elaboration of the cellular immune responses. Despite the gene diversity of the TCR chains, two structural features are common to all known subunits. First, they are transmembrane proteins with a single transmembrane spanning domain—presumably alpha-helical. Second, all TCR chains have the unusual feature of possessing a charged amino acid within the predicted transmembrane domain. The invariant chains have a single negative charge, conserved between the mouse and human, and the variant chains possess one (TCR-$\beta$) or two (TCR-$\alpha$) positive charges. The transmembrane sequence of TCR-$\alpha$ is highly conserved in a number of species and thus phylogenetically may serve an important functional role. The octapeptide sequence containing the hydrophilic amino acids arginine and lysine is identical between the species.

A T-cell response is modulated by antigen binding to a TCR. One type of TCR is a membrane bound heterodimer consisting of an $\alpha$ and $\beta$ chain resembling an immunoglobulin variable (V) and constant (C) region. The TCR $\alpha$ chain includes a covalently linked V-$\alpha$ and C-$\alpha$ chain, whereas the $\beta$ chain includes a V-$\beta$ chain covalently linked to a C-$\beta$ chain. The V-$\alpha$ and V-$\beta$ chains form a pocket or cleft that can bind a superantigen or antigen in the context of a major histocompatibility complex (MHC) (known in humans as an HLA complex). See, Davis *Ann. Rev. of Immunology* 3: 537 (1985); *Fundamental Immunology* 3rd Ed., W. Paul Ed. Rsen Press LTD. New York (1993).

The extracellular domains of the TCR chains ($\alpha\beta$ or $\gamma\delta$) can also engineered as fusions to heterologous transmembrane domains for expression on the cell surface. Such TCRs may include fusions to CD3, CD28, CD8, 4-1BB and/or chimeric activation receptor (CAR) transmembrane or activation domains. TCRs can also be the soluble proteins comprising one or more of the antigen binding domains of $\alpha\beta$ or $\gamma\delta$ chains. Such TCRs may include the TCR variable domains or function fragments thereof with or without the TCR constant domains. Soluble TCRs may be heterodimeric or single-chain molecules.

Fc Domain

Protein complexes of the invention may contain an Fc domain. For example, 2B8T3M comprises an anti-CD3 scAb/huIL-15N72D:anti-CD20 scAb/huIL-15R$\alpha$Su/hu-IgG1 Fc fusion complex. Fusion proteins that combine the Fc regions of IgG with the domains of another protein, such as various cytokines and soluble receptors have been reported (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_H1$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15R$\alpha$ covalently linked to the Fc portion of the human heavy chain IgG protein are described herein (e.g., 2B8T3M).

The term "Fc" refers to the fragment crystallizable region which is the constant region of an antibody that interacts with cell surface receptors called Fc receptors and some proteins of the complement system. Such an "Fc" is in dimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins. In some embodiments, Fc domain of the complex is capable of interacting with Fc receptors to mediate antibody-dependent cell-mediated cytotoxicity (ADCC) and/or antibody dependent cellular phagocytosis (ADCP). In other applications, the complex comprises an Fc domain (e.g., IgG4 Fc) that is incapable of effectively mediating ADCC or ADCP.

In some embodiments, the term "Fc variant" refers to a molecule or sequence that is modified from a native Fc, but still comprises a binding site for the salvage receptor, FcRn. International applications WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that alters one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cellular cytotoxicity (ADCC) or (8) antibody-dependent cellular phagocytosis (ADCP). Such alterations can increase or decrease any one or more of these Fc properties. Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Fusions Protein Complexes

The invention provides for fusion protein complexes (FIG. 1). In some cases, the first fusion protein comprises a first biologically active polypeptide covalently linked to interleukin-15 (IL-15) or functional fragment thereof; and the second fusion protein comprises a second biologically active polypeptide covalently linked to soluble interleukin-15 receptor alpha (IL-15Rα) polypeptide or functional fragment thereof, where the IL-15 domain of a first fusion protein binds to the soluble IL-15Rα domain of the second fusion protein to form a soluble fusion protein complex. Fusion protein complexes of the invention also comprise immunoglobulin Fc domain or a functional fragment thereof linked to one or both of the first and second fusion proteins. Preferably, the Fc domains linked to the fusion proteins interact to form a fusion protein complex. Such a complex may be stabilized by disulfide bond formation between the immunoglobulin Fc domains. In one aspect, the soluble fusion protein complexes of the invention include an IL-15 polypeptide, IL-15 variant or a functional fragment thereof and a soluble IL-15Rα polypeptide or a functional fragment thereof, wherein one or both of the IL-15 and IL-15Rα polypeptides further include an immunoglobulin Fc domain or a functional fragment thereof.

In certain examples, one or both of the first and second biologically active polypeptides comprises an antibody or functional fragment thereof. For example, one of the biologically active polypeptides comprises a first soluble anti-CD3 single chain antibody or functional fragment thereof. In another example, the other or second biologically active polypeptide comprises a disease antigen-specific antibody or functional fragment thereof. In one embodiment, the invention provides 2B8T3M, comprising a soluble anti-CD3 scAb/huIL-15N72D:anti-CD20 scAb/huIL-15RαSu/huIgG1 Fc fusion protein complex. In this complex, the huIL-15N72D and huIL-15RαSu domains interact and the huIgG1 Fc domains on two anti-CD20 scAb/huIL-15RαSu/huIgG1 Fc fusion protein to form a multichain fusion protein complex (see for example, FIG. 2).

As used herein, the term "biologically active polypeptide" or "effector molecule" is meant an amino acid sequence such as a protein, polypeptide or peptide; a sugar or polysaccharide; a lipid or a glycolipid, glycoprotein, or lipoprotein that can produce the desired effects as discussed herein. Effector molecules also include chemical agents. Also contemplated are effector molecule nucleic acids encoding a biologically active or effector protein, polypeptide, or peptide. Thus, suitable molecules include regulatory factors, enzymes, antibodies, or drugs as well as DNA, RNA, and oligonucleotides. The biologically active polypeptides or effector molecule can be naturally-occurring or it can be synthesized from known components, e.g., by recombinant or chemical synthesis and can include heterologous components. A biologically active polypeptide or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, but are not limited to, for example, forming a fusion protein complex of the invention with increased binding activity, killing a target cell, e.g. either to induce cell proliferation or cell death, initiate an immune response, in preventing or treating a disease, or to act as a detection molecule for diagnostic purposes. For such detection, an assay could be used, for example an assay that includes sequential steps of culturing cells to proliferate same, and contacting the cells with a fusion complex of the invention and then evaluating whether the fusion complex inhibits further development of the cells.

Covalently linking the effector molecule to the fusion protein complexes of the invention in accordance with the invention provides a number of significant advantages. Fusion protein complexes of the invention can be produced that contain a single effector molecule, including a peptide of known structure. Additionally, a wide variety of effector molecules can be produced in similar DNA vectors. That is, a library of different effector molecules can be linked to the fusion protein complexes for recognition of infected or diseased cells. Further, for therapeutic applications, rather than administration of a the fusion protein complex of the invention to a subject, a DNA expression vector coding for the fusion protein complex can be administered for in vivo expression of the fusion protein complex. Such an approach avoids costly purification steps typically associated with preparation of recombinant proteins and avoids the complexities of antigen uptake and processing associated with conventional approaches.

As noted, components of the fusion proteins disclosed herein, e.g., effector molecule such as cytokines, chemokines, growth factors, protein toxins, immunoglobulin domains or other bioactive molecules and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate modification, identification and/or purification of the fusion protein. More specific fusion proteins are in the Examples described below.
Linkers The fusion complexes of the invention preferably also include a flexible linker sequence interposed between the IL-15 or IL-15Rα domains and the biologically active polypeptide. The linker sequence should allow effective positioning of the biologically active polypeptide with respect to the IL-15 or IL-15Rα domains to allow functional activity of both domains.

In certain cases, the soluble fusion protein complex has a linker wherein the first biologically active polypeptide is covalently linked to IL-15 (or functional fragment thereof) by polypeptide linker sequence. In other aspects, the soluble fusion protein complex as described herein has a linker wherein the second biologically active polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably, about 80 or 90 percent or greater of the linker sequence comprises glycine, alanine or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).
Pharmaceutical Therapeutics The invention provides pharmaceutical compositions comprising fusion protein complexes for use as a therapeutic. In one aspect, fusion protein complex of the invention is administered systemically, for example, formulated in a pharmaceutically-acceptable buffer such as physiological saline. Preferable routes of administration include, for example, instillation into the bladder, subcutaneous, intravenous, intraperitoneal, intramuscular, intratumoral or intradermal injections that provide continuous, sustained or effective levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, autoimmune or infectious diseases, although in certain instances lower amounts will be needed because of the increased specificity of the compound. A compound is administered at a dosage that enhances an immune response of a subject, or that reduces the proliferation, survival, or invasiveness of a neoplastic, infected or autoimmune cell as determined by a method known to one skilled in the art.
Formulation of Pharmaceutical Compositions The administration of the fusion protein complex of the invention for the treatment of a neoplasia, infectious or autoimmune disease is by any suitable means that results in a concentration of the therapeutic that, combined with other components, is effective in ameliorating, reducing, or stabilizing said neoplasia, infectious or autoimmune disease. The fusion protein complex of the invention may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 µg compound/kg body weight to about 5000 mg compound/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, 5, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,600, 1,700, 1,800, 1,900, 2,000, 2,500, 3,000, 3,500, 4,000, 4,500, or 5,000 mg/kg body weight. Alternatively, doses are in the range of about 5 mg compound/Kg body weight to about 20 mg compound/kg body weight. In another example, the doses are about 8, 10, 12, 14, 16 or 18 mg/kg body weight. Preferably, 2B8T3M is administered at 0.5 mg/kg-about 10 mg/kg (e.g., 0.5, 1, 3, 5, 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes. Preferably, 2B8T3M is formulated in an excipient suitable for parenteral administration.

Parenteral Compositions

The pharmaceutical composition comprising a fusion protein complex of the invention are administered parenterally by injection, infusion or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising a fusion protein complex of the invention for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or it is be presented as a dry powder to be reconstituted with water or another suitable vehicle before use. Apart from the active agent that reduces or ameliorates a neoplasia, infectious or autoimmune disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

The present invention provides methods of treating neoplasia, infectious or autoimmune diseases or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplasia, infectious or autoimmune disease or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplasia, infectious disease, autoimmune disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders in which an increase in an immune response is desired.

The invention also provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, the fusion protein complex of the invention is administered in combination with any other standard therapy; such methods are known to the skilled artisan and described in Remington's Pharmaceutical Sciences by E. W. Martin. If desired, fusion protein complexes of the invention is administered in combination with any conventional anti-neoplastic therapy, including but not limited to, immunotherapy, therapeutic antibodies, targeted therapy, surgery, radiation therapy, or chemotherapy.

Kits or Pharmaceutical Systems

Pharmaceutical compositions comprising the fusion protein complex of the invention may be assembled into kits or pharmaceutical systems for use in ameliorating a neoplasia, infectious or autoimmune disease. Kits or pharmaceutical systems according to this aspect of the invention comprise a carrier means, such as a box, carton, tube, having in close confinement therein one or more container means, such as vials, tubes, ampoules, bottles and the like. The kits or pharmaceutical systems of the invention may also comprise associated instructions for using the fusion protein complex of the invention.

Recombinant Protein Expression

In general, preparation of the fusion protein complexes of the invention (e.g., components of 2B8T3M) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transfection and the choice of expression vehicle will depend on the host system selected. Transformation methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein) raised against the polypeptide may be attached to a column and used to isolate the recombinant polypeptide. Lysis and fractionation of polypeptide-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980).

As used herein, biologically active polypeptides or effector molecules of the invention may include factors such as cytokines, chemokines, growth factors, protein toxins, immunoglobulin domains or other bioactive proteins such as enzymes. Also, biologically active polypeptides may include conjugates to other compounds such as non-protein toxins, cytotoxic agents, chemotherapeutic agents, detectable labels, radioactive materials and such.

Cytokines of the invention are defined by any factor produced by cells that affect other cells and are responsible for any of a number of multiple effects of cellular immunity. Examples of cytokines include but are not limited to the IL-2 family, interferon (IFN), IL-10, IL-1, IL-17, TGF and TNF cytokine families, and to IL-1 through IL-35, IFN-α, IFN-β, IFNγ, TGF-β, TNF-α, and TNFβ.

In an aspect of the invention, the first fusion protein comprises a first biologically active polypeptide covalently linked to interleukin-15 (IL-15) domain or a functional fragment thereof. IL-15 is a cytokine that affects T-cell activation and proliferation. IL-15 activity in affecting immune cell activation and proliferation is similar in some respects to IL-2, although fundamental differences have been well characterized (Waldmann, T A, 2006, *Nature Rev. Immunol.* 6:595-601).

In another aspect of the invention, the first fusion protein comprises an interleukin-15 (IL-15) domain that is an IL-15 variant (also referred to herein as IL-15 mutant). The IL-15 variant preferably comprises a different amino acid sequence that the native (or wild type) IL-15 protein. The IL-15 variant preferably binds the IL-15Rα polypeptide and functions as an IL-15 agonist or antagonist. Preferably, IL-15 variants with agonist activity have super agonist activity. The IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 variant binds with increased or decreased activity to the IL-15RβγC receptors. In some cases, the sequence of the IL-15 variant has at least one amino acid change, e.g. substitution or deletion, compared to the native IL-2 sequence, such changes resulting in IL-15 agonist or antagonist activity. Preferably, the amino acid substitutions/deletions are in the domains of IL-15 that interact with IL-15Rβ and/or γC. More preferably, the amino acid substitutions/deletions do not affect binding to the IL-15Rα polypeptide or the ability to produce the IL-15 variant. Suitable amino acid substitutions/deletions to generate IL-15 variants can be identified based on putative or known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. Preferably, IL-15 variants of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 variants with antagonist activity and N72D substitutions result in IL-15 variants with agonist activity.

Chemokines, similar to cytokines, are defined as any chemical factor or molecule which when exposed to other cells are responsible for any of a number of multiple effects of cellular immunity. Suitable chemokines may include but are not limited to the CXC, CC, C, and $CX_3C$ chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: GM-CSF, G-CSF, human growth factor and stem cell growth factor. Additional growth factors may also be suitable for uses described herein.

Toxins or cytotoxic agents include any substance that has a lethal effect or an inhibitory effect on growth when exposed to cells. More specifically, the effector molecule can be a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C).

Further, the effector molecule can be a chemotherapeutic drug such as, e.g., vindesine, vincristine, vinblastin, methotrexate, adriamycin, bleomycin, or cisplatin.

Additionally, the effector molecule can be a detectably-labeled molecule suitable for diagnostic or imaging studies. Such labels include biotin or streptavidin/avidin, a detectable nanoparticles or crystal, an enzyme or catalytically active fragment thereof, a fluorescent label such as green fluorescent protein, FITC, phycoerythrin, cychome, texas red or quantum dots; a radionuclide e.g., iodine-131, yttrium-90, rhenium-188 or bismuth-212; a phosphorescent or chemiluminescent molecules or a label detectable by PET, ultrasound or MRI such as Gd—or paramagnetic metal ion-based contrast agents. See e.g., Moskaug, et al. *J. Biol. Chem.* 264, 15709 (1989); Pastan, I. et al. *Cell* 47, 641, 1986; Pastan et al., Recombinant Toxins as Novel Therapeutic Agents, *Ann. Rev. Biochem.* 61, 331, (1992); "Chimeric Toxins" *Olsnes and Phil, Pharmac. Ther.*, 25, 355 (1982); published PCT application no. WO 94/29350; published PCT application no. WO 94/04689; published PCT application no. WO2005046449 and U.S. Pat. No. 5,620,939 for disclosure relating to making and using proteins comprising effectors or tags.

A protein fusion or conjugate complex that includes a covalently linked IL-15 and IL-15Rα domains has several important uses. For example, the protein fusion or conjugate complex comprising an anti-CD3 scAb and an anti-CD20 scAb can be employed to deliver the IL-15:IL-15Rα complex to certain cells, e.g., B cell lymphoma cells that express CD20 receptor and CD8$^+$ T cells that express CD3 receptor. Accordingly, the protein fusion or conjugate complex provides means of selectively damaging or killing cells comprising the ligand. Examples of cells or tissue capable of being damaged or killed by the protein fusion or conjugate complexes include tumors and virally or bacterially infected cells expressing one or more ligands. Cells or tissue susceptible to being damaged or killed can be readily assayed by the methods disclosed herein.

The IL-15 and IL-15Rα polypeptides of the invention suitably correspond in amino acid sequence to naturally occurring IL-15 and IL-15Rα molecules, e.g. IL-15 and IL-15Rα molecules of a human, mouse or other rodent, or other mammal. Sequences of these polypeptides and encoding nucleic acids are known in the literature, including human interleukin 15 (IL15) mRNA—GenBank: U14407.1 (incorporated herein by reference), Mus musculus interleukin 15 (IL15) mRNA—GenBank: U14332.1 (incorporated herein by reference), human interleukin-15 receptor alpha chain precursor (IL15RA) mRNA—GenBank: U31628.1 (incorporated herein by reference), Mus musculus interleukin 15 receptor, alpha chain—GenBank: BC095982.1 (incorporated herein by reference).

In some settings, it can be useful to make the protein fusion or conjugate complexes of the present invention polyvalent, e.g., to increase the valency of the sc-antibody. In particular, interactions between the IL-15 and IL-15Rα domains of the fusion protein complex provide a means of generating polyvalent complexes. In addition, the polyvalent fusion protein can be made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein can be covalently linked to a tag or other fused protein which includes such a reactive amino acid(s). Suitable side chains can be included to chemically link two or more fusion proteins to a suitable dendrimer or other nanoparticle to give a multivalent molecule. Dendrimers are synthetic chemical polymers that can have any one of a number of different functional groups of their surface (D. Tomalia, Aldrichimica Acta, 26:91:101 (1993)). Exemplary dendrimers for use in accordance with the present invention include e.g. E9 starburst polyamine dendrimer and E9 combust polyamine dendrimer, which can link cystine residues. Exemplary nanoparticles include liposomes, core-shell particles or PLGA-based particles.

In another aspect, one or both of the polypeptides of the fusion protein complex comprises an immunoglobulin domain. Alternatively, the protein binding domain-IL-15 fusion protein can be further linked to an immunoglobulin domain. The preferred immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some aspects, the immunoglobulin domains of the fusion protein complex contain mutations that reduce or augment Fc receptor or complement binding activity or glycosylation or dimerization, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Nucleic Acids and Vectors

The invention further provides nucleic acid sequences and particularly DNA sequences that encode the present fusion proteins (e.g., components of 2B8T3M). Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector that contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See, Sambrook et al., supra and Ausubel et al. supra.

Included in the invention are methods for making a soluble fusion protein complex, the method comprising introducing into a host cell a DNA vector as described herein encoding the first and second fusion proteins, culturing the host cell in media under conditions sufficient to express the fusion proteins in the cell or the media and allow association between IL-15 domain of a first fusion protein and the soluble IL-15Rα domain of a second fusion protein to form the soluble fusion protein complex, purifying the soluble fusion protein complex from the host cells or media.

In general, a preferred DNA vector according to the invention comprises a nucleotide sequence linked by phosphodiester bonds comprising, in a 5' to 3' direction a first cloning site for introduction of a first nucleotide sequence encoding a biologically active polypeptide, operatively linked to a sequence encoding an effector molecule.

The fusion protein components encoded by the DNA vector can be provided in a cassette format. By the term "cassette" is meant that each component can be readily substituted for another component by standard recombinant methods. In particular, a DNA vector configured in a cassette format is particularly desirable when the encoded fusion complex is to be used against pathogens that may have or have capacity to develop serotypes.

To make the vector coding for a fusion protein complex, the sequence coding for the biologically active polypeptide is linked to a sequence coding for the effector peptide by use of suitable ligases. DNA coding for the presenting peptide can be obtained by isolating DNA from natural sources such as from a suitable cell line or by known synthetic methods, e.g. the phosphate triester method. See, e.g., Oligonucleotide Synthesis, IRL Press (M. J. Gait, ed., 1984). Synthetic oligonucleotides also may be prepared using commercially available automated oligonucleotide synthesizers. Once isolated, the gene coding for the biologically active polypeptide can be amplified by the polymerase chain reaction (PCR) or other means known in the art. Suitable PCR primers to amplify the biologically active polypeptide gene may add restriction sites to the PCR product. The PCR product preferably includes splice sites for the effector peptide and leader sequences necessary for proper expression and secretion of the biologically active polypeptide-effector fusion complex. The PCR product also preferably includes a sequence coding for the linker sequence, or a restriction enzyme site for ligation of such a sequence.

The fusion proteins described herein are preferably produced by standard recombinant DNA techniques. For example, once a DNA molecule encoding the biologically active polypeptide is isolated, sequence can be ligated to another DNA molecule encoding the effector polypeptide. The nucleotide sequence coding for a biologically active polypeptide may be directly joined to a DNA sequence coding for the effector peptide or, more typically, a DNA sequence coding for the linker sequence as discussed herein may be interposed between the sequence coding for the biologically active polypeptide and the sequence coding for the effector peptide and joined using suitable ligases. The resultant hybrid DNA molecule can be expressed in a suitable host cell to produce the fusion protein complex. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

Other nucleotide sequences also can be included in the gene construct. For example, a promoter sequence, which controls expression of the sequence coding for the biologically active polypeptide fused to the effector peptide, or a leader sequence, which directs the fusion protein to the cell surface or the culture medium, can be included in the construct or present in the expression vector into which the construct is inserted. An immunoglobulin or CMV promoter is particularly preferred.

In obtaining variant biologically active polypeptide, IL-15, IL-15Rα or Fc domain coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein. In other instance, modifications to amino acid positions can be made to reduce or enhance the biological activity of the protein. Such changes can be introduced randomly or via site-specific mutations based on known or presumed structural or functional properties of targeted residue(s). Following expression of the variant protein, the changes in the biological activity due to the modification can be readily assessed using binding or functional assays.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50 C, 6×SSC (sodium chloride/sodium citrate buffer) and 0.1% SDS (sodium dodecyl sulfate) indicate about 60-70% homology, hybridization and wash conditions of 50-65 C, 1×SSC and 0.1% SDS indicate about 82-97% homology, and hybridization and wash conditions of 52 C, 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the world wide web at ncbi.nlm nih.gov and a version of ClustalW is available at 2.ebi.ac.uk.

The components of the fusion protein can be organized in nearly any order provided each is capable of performing its intended function. For example, in one embodiment, the biologically active polypeptide is situated at the C or N terminal end of the effector molecule.

Preferred effector molecules of the invention will have sizes conducive to the function for which those domains are intended. The effector molecules of the invention can be made and fused to the biologically active polypeptide by a variety of methods including well-known chemical cross-linking methods. See, e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule or a conjugate molecule in accord with the invention can be organized in several ways. In an exemplary configuration, the C-terminus of the biologically active polypeptide is operatively linked to the N-terminus of the effector molecule. That linkage can be achieved by recombinant methods if desired. However, in another configuration, the N-terminus of the biologically active polypeptide is linked to the C-terminus of the effector molecule.

Alternatively, or in addition, one or more additional effector molecules can be inserted into the biologically active polypeptide or conjugate complexes as needed.

Vectors and Expression

A number of strategies can be employed to express the components of fusion protein complex of the invention (e.g., 2B8T3M). For example, a construct encoding one or more components of fusion protein complex of the invention can be incorporated into a suitable vector using restriction enzymes to make cuts in the vector for insertion of the construct followed by ligation. The vector containing the gene construct is then introduced into a suitable host for expression of the fusion protein. See, generally, Sambrook et al., supra. Selection of suitable vectors can be made empirically based on factors relating to the cloning protocol. For example, the vector should be compatible with, and have the proper replicon for the host that is being employed. The vector must be able to accommodate the DNA sequence coding for the fusion protein complex that is to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See, Sambrook, supra. Stable transformed or transfected cell lines can then be selected. Cells expressing a fusion protein complex of the invention can be determined by known procedures. For example, expression of a fusion protein complex linked to an immunoglobulin can be determined by an ELISA specific for the linked immunoglobulin and/or by immuno-blotting. Other methods for detecting expression of fusion proteins comprising biologically active polypeptides linked to IL-15 or IL-15Rα domains are disclosed in the Examples.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein comples encompass non-mammalian eukaryotic cells as well, including insect (e.g., Sp. *frugiperda*), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in E. coli. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the biologically active polypeptide coding sequence may be used. Alternatively, a signal sequence which has been selected or designed for efficient secretion and processing in the expression host may also be used. For example, suitable signal sequence/host cell pairs include the B. subtilis sacB signal sequence for secretion in B. subtilis, and the Saccharomyces cerevisiae α-mating factor or P. pastoris acid phosphatase phoI signal sequences for P. pastoris secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1,000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for E. coli host cells, nptII confers kanamycin resistance to a wide variety of prokaryotic and eukaryotic cells) or that permit the host to grow on minimal medium (e.g., HIS4 enables P. pastoris or His⁻ S. cerevisiae to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of E. coli. Numerous cloning vectors suitable for construction of the expression construct are known in the art (λZAP and pBLUESCRIPT SK-1, Stratagene, La Jolla, Calif., pET, Novagen Inc., Madison, Wis., cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into S. cerevisiae cells by protoplast transformation or electroporation. Electroporation of S. cerevisiae is readily accomplished, and yields transformation efficiencies comparable to spheroplast transformation.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium to stimulate transcription of the nucleotides sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

An expressed protein fusion complex can be isolated and purified by known methods. Typically the culture medium is centrifuged or filtered and then the supernatant is purified by affinity or immunoaffinity chromatography, e.g. Protein-A or Protein-G affinity chromatography or an immunoaffinity protocol comprising use of monoclonal antibodies that bind the expressed fusion complex. The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography and methods utilizing a difference in isoelectric point, such as isoelectric focusing electrophoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

The present fusion protein complexes are suitable for in vitro or in vivo use with a variety of cells that are cancerous or are infected or that may become infected by one or more diseases.

Human interleukin-15 (huIL-15) is trans-presented to immune effector cells by the human IL-15 receptor α chain (huIL-15Rα) expressed on antigen presenting cells. IL-15Rα binds huIL-15 with high affinity (38 pM) primarily through the extracellular sushi domain (huIL-15RαSu). As described herein, the huIL-15 and huIL-15RαSu domains can be used as a scaffold to construct multi-domain fusion complexes.

IgG domains, particularly the Fc fragment, have been used successfully as dimeric scaffolds for a number of therapeutic molecules including approved biologic drugs. For example, etanercept is a dimer of soluble human p75 tumor necrosis factor-α (TNF-α) receptor (sTNFR) linked to the Fc domain of human IgG1. This dimerization allows etanercept to be up to 1,000 times more potent at inhibiting TNF-α activity than the monomeric sTNFR and provides the fusion with a five-fold longer serum half-life than the monomeric form. As a result, etanercept is effective at neutralization of the pro-inflammatory activity of TNF-α in vivo and improving patient outcomes for a number of different autoimmune indications.

In addition to its dimerization activity, the Fc fragment also provides cytotoxic effector functions through the complement activation and interaction with Fcγ receptors displayed on natural killer (NK) cells, neutrophils, phagocytes and dendritic cells. In the context of anti-cancer therapeutic antibodies and other antibody domain-Fc fusion proteins, these activities likely play an important role in efficacy observed in animal tumor models and in cancer patients. However these cytotoxic effector responses may not be sufficient in a number of therapeutic applications. Thus, there has been considerable interest in improving and expanding on the effector activity of the Fc domain and developing other means of recruiting cytolytic immune responses, including T cell activity, to the disease site via targeted therapeutic molecules. IgG domains have been used as a scaffold to form bispecific antibodies to improve the quality and quantity of products generated by the traditional hybridoma fusion technology. Although these methods bypass the shortcomings of other scaffolds, it has been difficult to produce bispecific antibodies in mammalian cells at levels sufficient to support clinical development and use.

In an effort to develop human-derived immunostimulatory multimeric scaffold, human IL-15 (huIL-15) and IL-15 receptor domains were used. huIL-15 is a member of the small four α-helix bundle family of cytokines that associates with the huIL-15 receptor α-chain (huIL-15Rα) with a high binding affinity (equilibrium dissociation constant (KD) ~$10^{-11}$M). The resulting complex is then trans-presented to the human IL-2/15 receptor β/common γ chain (huIL-15RβγC) complexes displayed on the surface of T cells and NK cells. This cytokine/receptor interaction results in expansion and activation of effector T cells and NK cells, which play an important role in eradicating virally infected and malignant cells. Normally, huIL-15 and huIL-15Rα are co-produced in dendritic cells to form complexes intracellularly that are subsequently secreted and displayed as heterodimeric molecules on cell surfaces. Thus, the characteristics of huIL-15 and huIL-15Rα interactions suggest that these inter chain binding domains could serve as a human-derived immunostimulatory scaffold to make soluble dimeric molecules capable of target-specific binding.

As described in detail below, an huIL-15:huIL-15RαSu-based scaffold was used to create 2B8T3M. The dimeric fusion protein complexes retained immunostimulatory and target-specific biological activity of their huIL-15 domains and binding domains, indicating that the addition of huIL-15 and huIL-15Rα did not significantly alter the spatial arrangement of the fusion domains and provided an adequate degree of conformational flexibility without impacting cytokine activity. Thus, this scaffold could be used to form multivalent fusion complexes, such as the 2B8T3M, to increase the overall binding affinity of molecules. The soluble fusion proteins were produced at relatively high levels in recombinant CHO cell culture (mgs per liter in cell culture supernatant without extensive cell line screening or optimization) and could be readily purified from the cell culture supernatants.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Lymphoma

Lymphoma is a type of blood cancer that occurs when B or T lymphocytes divide faster than normal cells or live longer than intended. For example, B cell lymphomas include both Hodgkin's lymphomas and most non-Hodgkin's lymphomas. B cell lymphomas express CD20.

Lymphoma may develop in the lymph nodes, spleen, bone marrow, blood or other organs. These malignant cells often originate in the lymph nodes, presenting as an enlargement of the node, i.e., a solid tumor of lymphoid cells. Lymphoma is definitively diagnosed by a lymph node biopsy, i.e., a partial or total excision of a lymph node, which is examined under a microscope. This examination may reveal histopathological features that may indicate lymphoma. Treatment might involve chemotherapy, radiotherapy, and/or bone marrow transplantation.

Example 1: Generation and Purification of T3 Fusion Proteins

Figure 2:
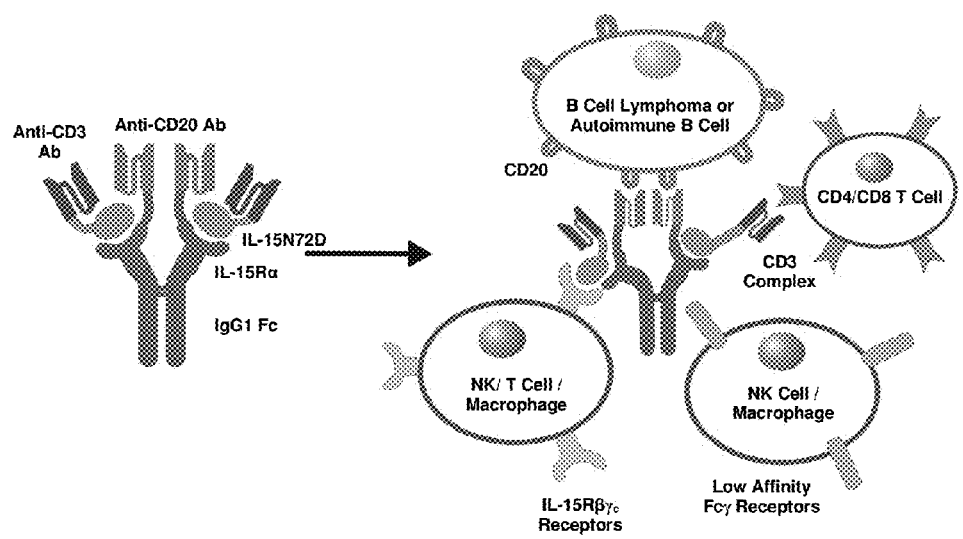
FIG. 2 is a schematic diagram illustrating the 2B8T3M complex comprising anti-CD3 scAb/huIL-15N72D and anti-CD20 scAb/huIL-15RαSu/huIgG1 Fc fusion proteins, and its immune-mediated effects against disease cells expressing CD20 antigen.

As described in detail below, a protein complex comprising an anti-CD3 scAb/huIL-15N72D and an anti-CD20 scAb/huIL-15RαSu/huIgG1 Fc was generated. This complex recognizes B cell lymphomas via the anti-CD20 scAb domain, induces NK and T cells responses via IL-15 activity, activates T cell responses via the anti-CD3 scAb domain, and stimulates ADCC and CDC via the Fc binding domain (FIG. 2).

Specifically, constructs were made linking a single-chain anti-human CD3 antibody to the huIL-15N72D chains. The anti-human CD3 single chain antibody (anti-CD3 scAb) sequence comprises the coding regions of the heavy and light chain V domains of the OKT3 antibody linked via a flexible linker sequence. In some cases, the anti-CD3 scAb is linked to the C-terminus of huIL-15N72D. In other cases, the anti-CD3 scAb is linked to the N-terminus of huIL-15N72D. The nucleic acid and protein sequences of a construct comprising the anti-CD3 scAb linked to the N-terminus of the huIL-15N72D are shown below.

The nucleic acid sequence of anti-CD3 scAb-IL-15N72D construct (including signal peptide sequence and stop codon) is as follows (SEQ ID NO: 1):

(Signal peptide)
ATGGAGACAGACACACTCCTGTTATGGGTACTGCTGCTCTGGGTTCCAGG

TTCCACCGGT- (anti-CD3 scAb (OKT3 VL-linker VH scFv))
CAAATTGTTCTCACCCAGTCTCCAGCAATCATGTCTGCATCTCCAGGGGA

GAAGGTCACCATGACCTGCAGTGCCAGCTCAAGTGTAAGTTACATGAACT

GGTACCAGCAGAAGTCAGGCACCTCCCCCAAAAGATGGATTTATGACACA

TCCAAACTGGCTTCTGGAGTCCCTGCTCACTTCAGGGGCAGTGGGTCTGG

GACCTCTTACTCTCTCACAATCAGCGGCATGGAGGCTGAAGATGCTGCCA

CTTATTACTGCCAGCAGTGGAGTAGTAACCCATTCACGTTCGGCTCGGGG (Linker)
ACAAAGTTGGAAATAAACCGG<u>ACTAGTGGAGGTGGCGGATCAGGAGGCGG</u>

<u>AGGTTCTGGCGGAGGTGGGAGTCTCGAG</u>CAGGTCCAGCTGCAGCAGTCTG

GGGCTGAACTGGCAAGACCTGGGGCCTCAGTGAAGATGTCCTGCAAGGCT

TCTGGCTACACCTTTACTAGGTACACGATGCACTGGGTAAAACAGAGGCC

TGGACAGGGTCTGGAATGGATTGGATACATTAATCCTAGCCGTGGTTATA

CTAATTACAATCAGAAGTTCAAGGACAAGGCCACATTGACTACAGACAAA

TCCTCCAGCACAGCCTACATGCAACTGAGCAGCCTGACATCTGAGGACTC

TGCAGTCTATTACTGTGCAAGATATTATGATGATCATTACTGCCTTGACT

ACTGGGGCCAAGGCACCACTCTCACAGTCTCCTCA- (Human IL-15N72D)
AACTGGGTTAACGTAATAAGTGATTTGAAAAAAATTGAAGATCTTATTCA

ATCTATGCATATTGATGCTACTTTATATACGGAAAGTGATGTTCACCCCA

GTTGCAAAGTAACAGCAATGAAGTGCTTTCTCTTGGAGTTACAAGTTATT

TCACTTGAGTCCGGAGATGCAAGTATTCATGATACAGTAGAAAATCTGAT

CATCCTAGCAAACGACAGTTTGTCTTCTAATGGGAATGTAACAGAATCTG

GATGCAAAGAATGTGAGGAACTGGAGGAAAAAAATATTAAAGAATTTTTG

CAGAGTTTTGTACATATTGTCCAAATGTTCATCAACACTTCTTAA

The amino acid sequence of the anti-CD3 scAb-IL-15N72D fusion protein (including signal peptide sequence) is as follows (SEQ ID NO: 2):

(Signal peptide)
METDTLLLWVLLLWVPGSTG- (anti-CD3 scAb (OKT3 VL-linker VH scFv))
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG (Linker)
TKLEINR<u>TSGGGSGGGGSGGGGSLE</u>QVQLQQSGAELARPGASVKMSCKA

SGYTFTRYTMHWVKQRPGQGLEWIGYINPSRGYTNYNQKFKDKATLTTDK

SSSTAYMQLSSLTSEDSAVYYCARYYDDHYCLDYWGQGTTLTVSS- (human IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

The sequences were cloned into expression vectors as described previously (U.S. Pat. No. 8,507,222, at Examples 1 and 2, incorporated herein by reference), and the expression vectors transfected into CHO cells. Cells were also transfected with vectors expressing anti-CD20 scAb/huIL-15RαSu/huIgG1 Fc construct (U.S. Pat. No. 8,507,222, at Example 18, incorporated herein by reference).

The nucleic acid sequence of anti-CD20 scAb/huIL-15RαSu/huIgG1 Fc construct (including leader sequence) is as follows (SEQ ID NO: 3):

(leader sequence)
ATGGATTTTCAGGTGCAGATTATCAGCTTCCTGCTAATCAGTGCTTCAGT

CATAATGTCCAGAGGA (anti-CD20 light chain V domain)
CAAATTGTTCTCTCCCAGTCTCCAGCAATCCTGTCTGCATCTCCAGGGGA

GAAGGTCACAATGACTTGCAGGGCCAGCTCAAGTGTAAGTTACATCCACT

GGTTCCAGCAGAAGCCAGGATCCTCCCCCAAACCCTGGATTTATGCCACA

TCCAACCTGGCTTCTGGAGTCCCTGTTCGCTTCAGTGGCAGTGGGTCTGG

GACTTCTTACTCTCTCACAATCAGCAGAGTGGAGGCTGAAGATGCTGCCA

```
CTTATTACTGCCAGCAGTGGACTAGTAACCCACCCACGTTCGGAGGGGGG

ACCAAGCTGGAAATCAAA (linker)
AGTGGAGGTGGCGGATCCGGAGGTGGAGGTTCTGGTGGAGGTGGGAGT (anti-CD20 heavy chain V domain)
CAGGTACAACTGCAGCAGCCTGGGGCTGAGCTGGTGAAGCCTGGGGCCTC

AGTGAAGATGTCCTGCAAGGCTTCTGGCTACACATTTACCAGTTACAATA

TGCACTGGGTAAAACAGACACCTGGTCGGGGCCTGGAATGGATTGGAGCT

ATTTATCCCGGAAATGGTGATACTTCCTACAATCAGAAGTTCAAAGGCAA

GGCCACATTGACTGCAGACAAATCCTCCAGCACAGCCTACATGCAGCTCA

GCAGCCTGACATCTGAGGACTCTGCGGTCTATTACTGTGCAAGATCGACT

TACTACGGCGGTGACTGGTACTTCRATGTCTGGGGCGCAGGGACCACGGT

CACMGTCTCTGCA (Human IL-15R α sushi domain)
ATCACGTGCCCTCCCCCCATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA (Human IgG1 CH2-CH3 (Fc) domain)
GAGCCGAAATCTTGTGACAAAACTCACACATGCCCACCGTGCCCAGCACC

TGAACTCCTGGGGGACCGTCAGTCTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGC

AGGTGGCAGCAGGGGAACGTCTTCTCATGCTCCGTGATGCATGAGGCTCT

GCACAACCACTACACGCAGAAGAGCCTCTCCCTGTCTCCTGGTAAATAA
```

The amino acid sequence of the mature anti-CD20 scAb/huIL-15RαSu/huIgG1 Fc fusion protein (including leader sequence) is as follows (SEQ ID NO: 4):

```
(anti-CD20 light chain V domain)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIK (linker)
SGGGGSGGGGSGGGGS (anti-CD20 heavy chain V domain)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSA (Human IL-15R α sushi domain)
ITCPPPMSVEHADIWVKSYSLYSRERYICNSGFKRKAGTSSLTECVLNKA

TNVAHWTTPSLKCIR (Human IgG1 CH2-CH3 (Fc) domain)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFPLYSKLTVDKS

RWQQGNVFSCSVMHEALHNHYTQKSLSLSPGK
```

An exemplary IL-15N72D amino acid sequence is provided below (with leader peptide) (SEQ ID NO: 5):

```
(Leader peptide)
METDTLLLWVLLLWVPGSTG- (IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS
```

In some cases, the leader peptide is cleaved from the mature IL-15N72D polypeptide.

An exemplary IL-15RαSu/Fc amino acid sequence (with leader peptide) is provided below (SEQ ID NO: 6):

```
(Leader peptide)
MDRLTSSFLLLIVPAYVLS- (IL-15RαSu)
ITCPPPMSVEHADIWVKSYSLYSRERYICNSGFKRKAGTSSLTECVLNKA

TNVAHWTTPSLKCIR- (IgG1 CH2-CH3 (Fc domain))
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFPLYSKLTVDKS

RWQQGNVFSCSVMHEALHNHYTQKSLSLSPGK
```

In some cases, the mature IL-15RαSu/Fc protein lacks the leader sequence.

Figure 3:
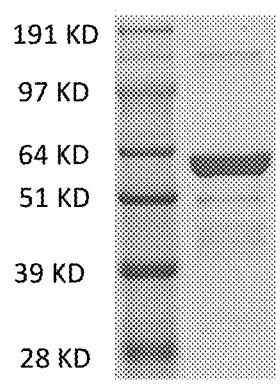
FIG. 3 is a photograph showing a sodium dodecyl sulfate polyacrylamide gel electrophoresis (SDS-PAGE) analysis of the T3M complex following disulfide bond reduction. Right lane: 2B8T3M (3 µg); left lane: marker.

Co-expression of the two constructs in CHO cells allowed formation and secretion of a soluble anti-CD3 scAb/huIL-15N72D:anti-CD20 scAb/huIL-15RαSu/huIgG1 Fc complex (referred to as anti-CD3 scAb-anti-CD20 scAb T3M; 2B8T3M) which was purified from the CHO cell culture supernatant using Protein A affinity chromatography. SDS-PAGE analysis of the purified protein is shown in FIG. 3. Bands corresponding to the soluble anti-CD20 scAb/huIL-15RαSu/huIgG1 Fc anti-CD3 scAb/huIL-15N72D proteins at ~60 kDa and ~40 kDa, respectively, were observed.

Example 2: In Vitro Characterization of the Binding Activities of the T3 Molecule ELISA-based methods confirmed the formation of an anti-CD3 scAb/huIL-15N72D:anti-CD20 scAb/huIL- 15RαSu/huIgG1 Fc complex. In one example, the fusion protein complexes were detected using a huIgG1/huIL15-specific ELISA with a capture antibody, anti-human IgG antibody (Jackson ImmunoResearch), and a detection antibody, biotinylated anti-human IL-15 antibody (BAM 247, R&D Systems).

Figure 4A:
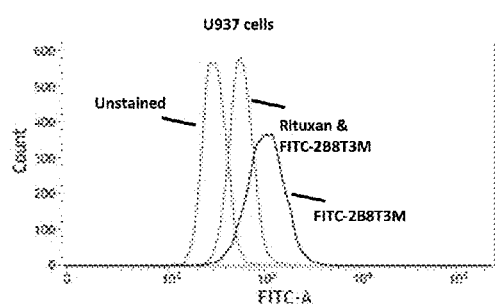
FIG. 4A is a line graph illustrating binding activity of 2B8T3M to Fc receptor-bearing cell line.
Figure 4B:
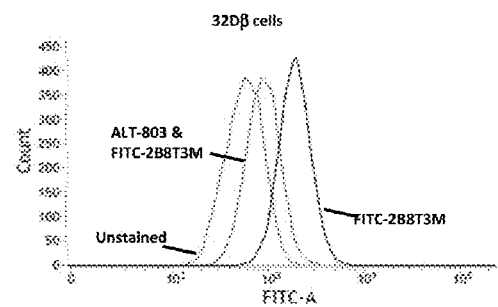
FIG. 4B is a line graph showing the binding activity of 2B8T3M to an IL-15 receptor-bearing cell line.

Additionally, binding of the complex to Fc receptors, IL-15 βγ receptors, CD3, and CD20 was assessed by flow cytometry using receptor bearing cells. In these studies, Fc receptor-positive U937 and IL-15βγ-positive 32Dβ cells ($5 \times 10^5$ cells/test) were stained with fluorescein isothiocyanate (FITC)-labeled anti-CD3 scAb-anti-CD20 scAb T3M (4 μg/test in 100 μL). As shown in FIG. 3, flow cytometry analysis demonstrated binding of the anti-CD3 scAb-anti-CD20 scAb T3M complex (2B8T3M) to the U937 and 32Dβ cells. Specificity of this binding was tested by addition of unlabeled blocking reagents (80 μg/test) containing the Fc domains (anti-CD20 Ab: Rituxan) or the IL-15 domain (IL-15N72D/IL-15R-Fc: ALT-803) to the cell staining assays (FIG. 3). By "ALT-803" is meant a complex comprising IL-15N72D noncovalently associated with a dimeric IL-15RαSu/Fc fusion protein, wherein said complex exhibits immune stimulating activity (See, e.g., U.S. Ser. No. 13/769,179, incorporated herein by reference). These reagents diminished FITC-2B8T3M specific staining of Fc receptor-positive U937 and IL-15Rβγ-positive 32Dβ cells (FIG. 4).

It was next determined whether the complex would bind receptor-bearing human peripheral blood mononuclear cells (PBMCs). Human PBMC ($5 \times 10^5$ cells/test) were stained with FITC-labeled 2B8T3M (2 μg/test in 140 μL) with and without blocking reagents (50 μg/test): Rituxan to block CD20 binding, cOKT3 (chimeric OKT3 Ab) to block CD3 binding, and ALT-803 to block IL-15 receptor binding. Staining with appropriate antibodies identified CD20-bearing HLA-DR$^+$ B cells, CD3-bearing CD8$^+$ T cells, and IL-15R-bearing CD16$^+$ NK cells in the PBMC population. In each case, specific binding with FITC-labeled 2B8T3M complex to these cells was observed based on positive staining and inhibition by the blocking reagents (FIG. 5).

Example 3: Characterization of the Biological Activity of the T3M Complex

Figure 6:
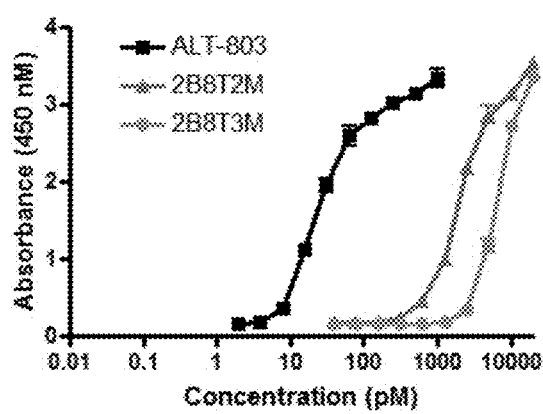
FIG. 6 is a line graph illustrating the proliferation of IL-15-dependent 32Dβ cells mediated by 2B8T3M, 2B8T2M, and ALT-803.

IL-15 bioactivity assays based on proliferation of IL-15Rβγ-positive 32Dβ cells were conducted with the anti-CD3 scAb-anti-CD20 scAb T3M complex (2B8T3M). The IL-15-dependent cells at $1 \times 10^4$ cells/well were incubated at 37° C. in 200 μL RPMI:10% FBS media containing increasing amounts of 2B8T3M. After 3 days, WST-1 (a water soluble tetrazolium salt) proliferation reagent (10 μL/well) was added. After 4 hours, absorbance was measured at 450 nm to determine cell proliferation based on cleavage of WST-1 to a soluble formazan dye by metabolically active cells. The bioactivity of ALT-803 and an anti-CD20 scAb T2M complex (2B8T2M) was assessed as positive controls. By "2B8T2M" is meant a soluble anti-CD20 scAb/huIL-15N72D:anti-CD20 scAb/huIL-15RαSu/huIgG1 Fc complex (See, e.g., U.S. Pat. No. 8,507,222, incorporated herein by reference). As shown in FIG. 6, 2B8T3M was able to promote cell proliferation of 32Dβ cells, thereby demonstrating IL-15 activity. The activity of 2B8T3M was slightly less than that of 2B8T2M, but significantly less than that of ALT-803, presumably due to the linkage of anti-CD3 scAb to the IL-15N72D domain.

Example 4: Anti-Tumor Activity of the T3M Complex

It was next determined whether the anti-CD3 scAb-anti-CD20 scAb T3M complexes were capable of killing CD20$^+$ tumor cells (Daudi cells) via CD3-mediated T cell activation. Human peripheral blood mononuclear cells were isolated from the buffy coat of donor blood. Natural killer (NK) cells and T cells were enriched by passing the cells over a nylon wool column. CD4 and CD8 T cells were purified by magnetic bead separation using a MACS column. The human immune effector cells ($1 \times 10^6$/well) were mixed with Violet CellTrace labeled Daudi target cells ($2 \times 10^5$/well) (E:T—5:1) and various concentrations of anti-CD3 scAb-anti-CD20 scAb T3M complexes. As a control, soluble anti-CD20 scAb/huIL-15N72D:anti-CD20 scAb/huIL-15RαSu/huIgG1 Fc complex (anti-CD20 scAb T2M), which lacks CD3 recognition, was used. After 20 hours of incubation in RPMI-10% FBS media at 37° C., the cells were harvested and stained with propidium iodide (PI) at final concentration of 10 μg/ml. The cells were analyzed by flow cytometry using a FACSVerse cytometer. The Daudi target cells were identified as violet labeled cells and dead Daudi target cells were violet PI stained cells. The percentage of dead Daudi cells was determined as a measure of CD20 target specific cytotoxicity.

Figure 7:
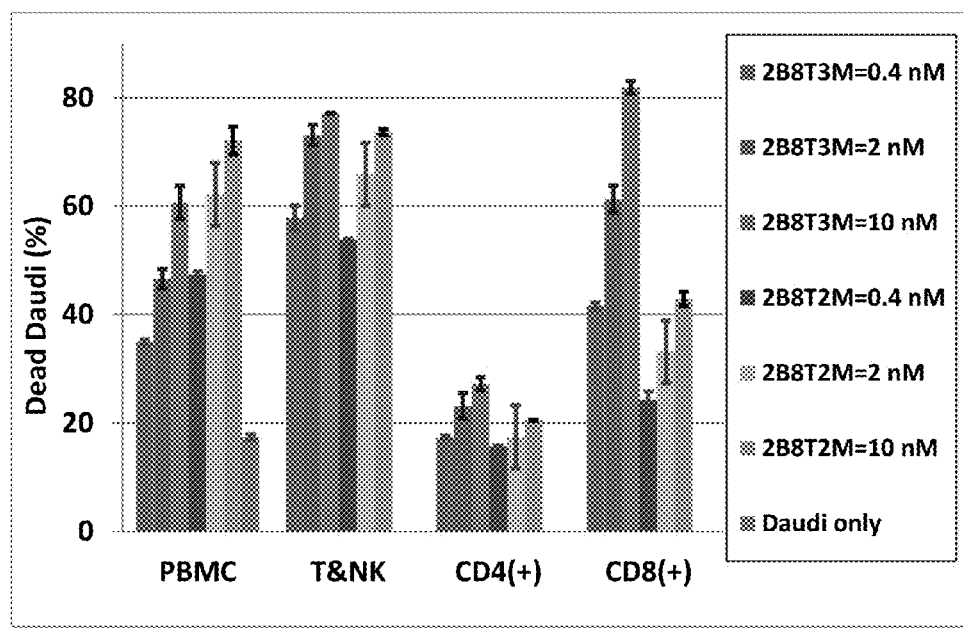
FIG. 7 is a bar chart illustrating the cytotoxicity of human immune cells against Daudi-B-cell lymphoma induced by 2B8T2M or 2B8T3M.

As shown in FIG. 7, both anti-CD3 scAb-anti-CD20 scAb T3M (2B8T3M) and anti-CD20 scAb T2M (2B8T2M) complexes were capable of mediating potent CD20 cell-specific cytotoxicity by human PBMCs and T cells+NK cells. However, unexpectedly, 2B8T3M was able to stimulate CD8$^+$ T cells and to a lesser degree CD4$^+$ T cells to kill Daudi cells more effectively than comparable levels of 2B8T2M. These results verify that 2B8T3M is capable of effectively enhancing cytotoxicity of CD3-positive T cells against tumor cells.

Figure 8:
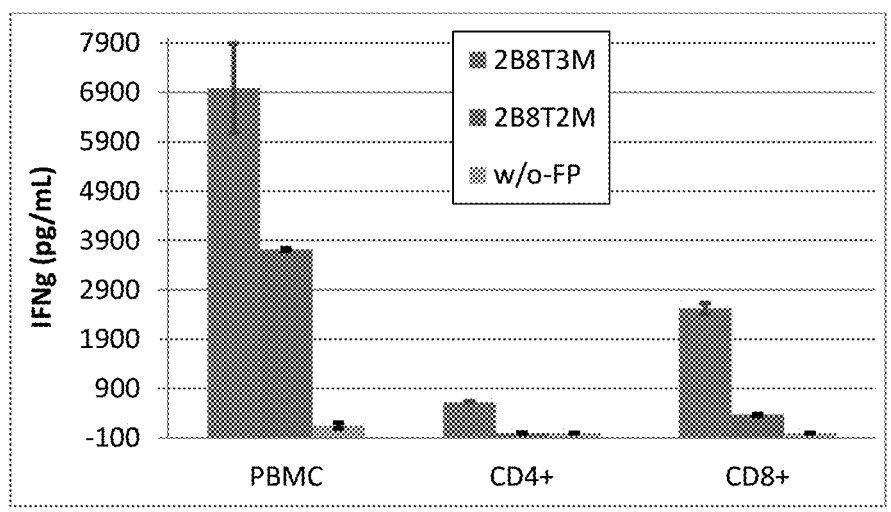
FIG. 8 is a bar chart showing interferon-γ (IFN-γ) release from human immune cells induced by 2B8T2M or 2B8T3M.

The level of immune activation based on interferon-γ (IFN-γ) release in these human immune cell-Daudi cell cultures was determined by ELISA. As shown in FIG. 8, unexpectedly, 2B8T3M at 10 nM was capable of stimulating the release of IFN-γ from human PBMCs and CD4$^+$ and CD8$^+$ T cells more effectively than 2B8T2M, demonstrating activation of immune cells via the CD3 binding domain.

Based on the in vitro results presented herein, the anti-CD20 scAb T3M molecule stimulates immune responses and exhibits antitumor activity against human lymphoma cells in standard xenograft tumor models (see for example, Rossi et al. Blood 2009; 114:3864; Gillis et al. Blood. 2005; 105:3972; and Xuan et al. Blood 2010; 115:2864-2871).

Similar T3M constructs comprising scAb or antibody recognition domains could be readily generated with antibody sequences specific to other CD antigens, cytokines or chemokine receptors or ligands, growth factor receptors or ligands, cell adhesion molecules, MHC/MHC-like molecules, Fc receptors, Toll-like receptors, NK receptors, TCRs, BCRs, positive/negative co-stimulatory receptors or ligands, death receptors or ligands, tumor associated antigens, virus-encoded and bacterial-encoded antigens, and bacterial-specific. Of particular interest are T3M with disease specific binding domains (e.g. scAbs) to antigens of CD4, CD19, CD21, CD22, CD23, CD25, CD30, CD33, CD38, CD40, CD44, CD51, CD52, CD70, CD74, CD80, CD123, CD152, CD147, CD221, EGFR, HER-2/neu, HER-1, HER-3, HER-4, CEA, OX40 ligand, cMet, tissue factor, Nectin-4, PSA, PSMA, EGFL7, FGFR, IL-6 receptor, IGF-1 receptor, GD2, CA-125, EpCam, death receptor 5, MUC1, VEGFR1, VEGFR2, PDGFR, Trail R2, folate receptor, angiopoietin-2, alphavbeta3 integrin receptor, HLA-DR antigens and other disease targets described herein. Antibody domains against viral antigens from HIV, HCV, HBC, CMV, HTLV, HPV, EBV, RSV and other virus are also of interest, particularly those recognizing the HIV envelope spike and/or gp120 and gp41 epitopes. Such antibody domains can be generated from sequences known in the art or isolated de novo from a variety of sources (i.e., vertebrate hosts or cells, combinatorial libraries, random synthetic libraries, computational modeling, etc.) known in the art.

Example 5: A Novel Fusion of ALT-803 (IL-15 Superagonist) with an Antibody Demonstrates Antigen-Specific Antitumor Responses Interleukin (IL)-15 and its receptor α (IL-15Rα) are co-expressed on antigen-presenting cells allowing transpresentation of IL-15 to immune cells bearing IL-2Rβγ$_C$ and stimulation of effector immune responses. It was previously reported that the high-affinity interactions between an IL-15 superagonist (IL-15N72D) and the extracellular IL-15Rα sushi domain (IL-15RαSu) could be exploited to create a functional scaffold for the design of multivalent disease-targeted complexes. The IL-15N72D:IL-15RαSuFc complex, also known as ALT-803, is a multimeric complex constructed by fusing IL-15N72D:IL-15RαSu to the Fc-domain of IgG1. ALT-803 is an IL-15 superagonist complex which has been developed as a potent antitumor immunotherapeutic and is in clinical trials. Describe herein is the creation of a novel fusion molecule, 2B8T2M, using the ALT-803 scaffold fused to four single-chains of the tumor-targeting monoclonal antibody, rituximab. This molecule displays tri-specific binding activity through its recognition of the CD20 molecule on tumor cells, stimulation via IL-2Rβγ$_C$ displayed on immune effector cells, and binding to Fcγ-receptors on natural killer (NK) cells and macrophages. 2B8T2M activates NK cells to enhance antibody-dependent cellular cytotoxicity (ADCC), mediates complement-dependent cytotoxicity (CDC), and induces apoptosis of B-lymphoma cells. When compared to rituximab, 2B8T2M exhibits significantly stronger antitumor activity in a xenograft SCID mouse model and depletes B cells in cynomolgus monkeys more efficiently. Thus, ALT-803 can be modified as a functional scaffold for creating multi-specific, targeted IL-15-based immunotherapeutics and may serve as a novel platform to improve antitumor activity and clinical efficacy of therapeutic antibodies.

Interleukin (IL)-15, a four-helix, common gamma-chain (γ$_C$) cytokine, is a critical factor for the development, proliferation, and activation of natural killer (NK) cells and CD8$^+$ T cells (1,2). IL-15 is co-expressed with its α-chain receptor (IL-15Rα) by antigen-presenting cells and the two proteins form a complex on the cell surface that is transpresented to NK and T cells bearing the IL-2Rβγ$_C$ complex (2). IL-15 binds to IL-15Rα at high affinity and IL-15Rα functions as a chaperone and conformational stabilizer to enhance the interaction between IL-15 and the IL-2Rβγ$_C$ (2). An IL-15 variant was identified carrying an asparagine to aspartic acid mutation at amino acid 72 (N72D), which exhibits superior binding to IL-2Rβγ$_C$ on immune cells and increased immunostimulatory activity (3). Previous studies have demonstrated that this IL-15 variant, when associated with a soluble IL-15Rα sushi domain fusion to IgG1 Fc (IL-15RαSuFc), could form a heterodimeric complex, IL-15N72D:IL-15RαSuFc (designated as ALT-803), which also exhibits increased binding activity to the IL-2RNC complex, enhanced capacity to stimulate NK and T cells, and has a longer biological half-life compared to native IL-15 (4). In various animal models, ALT-803 acts as a potent immunostimulant that is capable of simultaneously activating the innate and adaptive arms of the immune system to elicit both rapid and long-lasting protective responses against neoplastic challenges (5). Moreover, ALT-803 in combination with checkpoint blockade or therapeutic antibodies is effective in reducing tumor burden and prolonging survival in mouse tumor models (6,7). To make ALT-803-based molecules more specific and efficient in combating disease, ALT-803 was converted into a targeted immunotherapeutic by genetically fusing it with single-chain antibodies (scFv) at the N-termini of IL-15N72D and IL-15RαSuFc proteins. In this study, the anti-CD20 scFv was used as target-recognition domain to demonstrate that ALT-803 is a versatile, functional scaffold for creating disease-targeted immunostimulatory molecules. This novel single fusion protein approach was also found to improve the antibody-dependent cellular cytotoxicity (ADCC) and apoptotic functions of the anti-CD20 therapeutic antibody rituximab.

Creation of Multifunctional Protein Complexes Using the IL-15:IL-15Rα Scaffold

Figure 9:
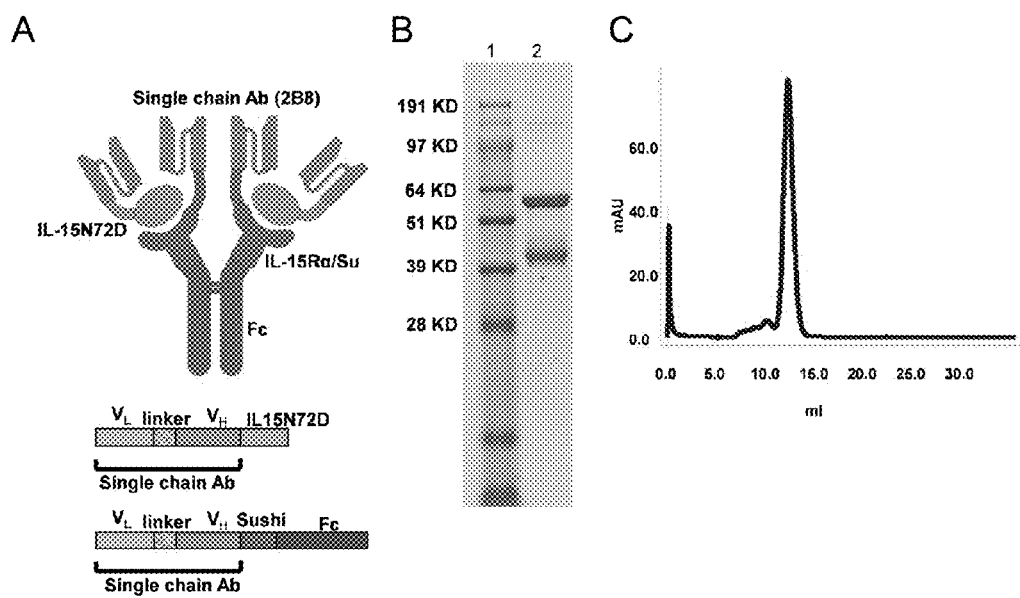
FIG. 9A-FIG. 9C show 2B8T2M fusion protein structure and characterization.

It was previously shown that biologically active fusion protein complexes can be generated using an IL-15:IL-15RαSu scaffold by fusing the N-termini of IL-15 and IL-15RαSu proteins to a p53(264-272)-specific chimeric single-chain TCR (c264scTCR) (8). Thus, it was hypothesized that ALT-803 (i.e., the IL-15N72D:IL-15RαSuFc complex) could also function as a protein scaffold to create multi-specific IL-15-based targeted immunotherapeutic agents. To test this, the variable regions of the heavy and light chains of rituximab were converted into a scFv (sc2B8) (9) and genetically fused sc2B8 to the N-termini of IL-15N72D and IL-15RαSuFc proteins of ALT-803. Based on the high binding-affinity between the IL-15N72D and IL-15RαSu domains, it was expected that the fusion proteins would form a heterodimeric complex between sc2B8-IL-15N72D and sc2B8-IL-15RαSuFc. In addition, the sc2B8-IL-15RαSuFc was expected to form a covalent dimer using the disulfide bonds provided by the Fc-domain. Therefore, this novel fusion protein complex (designated as 2B8T2M) was predicted to consist of two sc2B8-IL-15N72D and two sc2B8-IL-15RαSuFc proteins (FIG. 9A). Following stable co-transfection of the fusion protein expression vectors into CHO cells, soluble 2B8T2M was readily produced and purified from cell culture supernatants at a range of 10 to 40 mg/liter. When evaluated by reducing SDS-PAGE, the purified preparations consisted of 2 proteins that migrated at ~40 kDa and ~60 kDa (FIG. 9B), corresponding to the expected molecular weights of 38 kDa for sc2B8-IL-15N72D and 59 kDa for sc2B8-IL-15RαSuFc, respectively. In addition, formation of the multimeric fusion protein complex was verified by size exclusion chromatography which revealed the molecular mass of 2B8T2M to be 162 kDa based on protein size standards (FIG. 9C). In addition to 2B8T2M, similar fusion protein complexes were generated containing either a mutant Fc-domain with reduced Fc-receptor binding activity (2B8T2M-LA) (10) or a mutant IL-15 domain that is incapable of binding IL-2Rβ (2B8T2M-D8N). An additional fusion protein complex (designated c264T2M) comprised of a different targeting-domain (c264scTCR (8)) was genetically fused to the N-termini of IL-15N72D and IL-15RαSuFc proteins. These complexes served as controls to determine the roles of the Fc, IL-15N72D, and sc2B8 domains in the biological activities of 2B8T2M.

Figure 10:
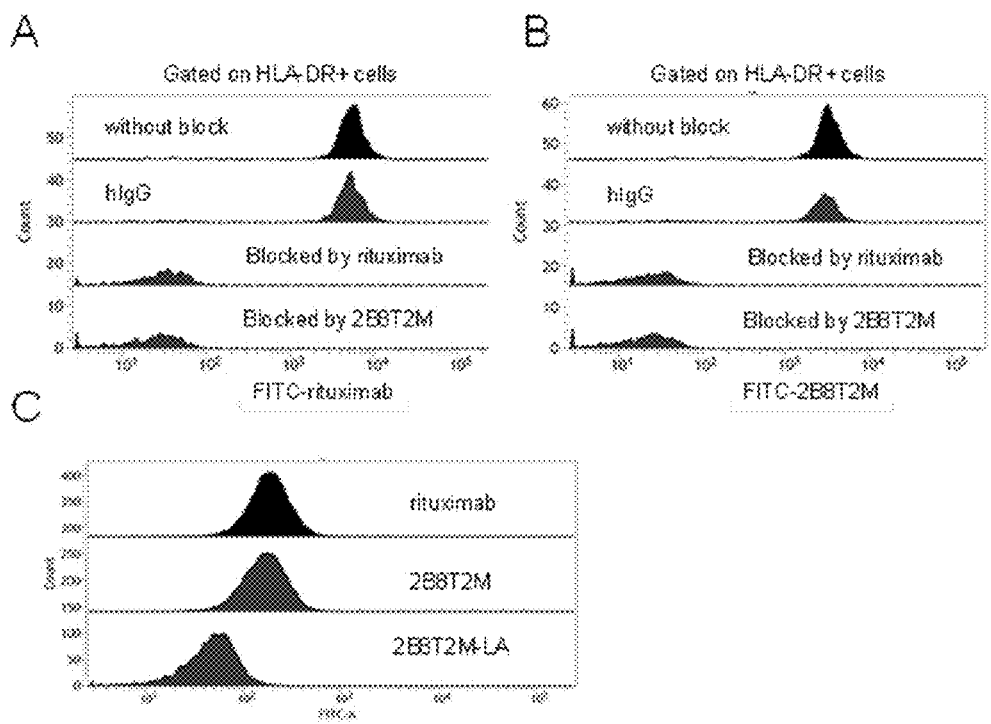
FIG. 10A-FIG. 10C show B cell binding of 2B8T2M. Analysis of target-specific binding activity of 2B8T2M by flow cytometry. Human PBMCs ($5 \times 10^5$/test) were added to rituximab, 2B8T2M, or human IgG as an isotype control at 1 mg/mL at final volume of 0.1 mL for 10 minutes. The reactions were stained with FITC-conjugated rituximab (FIG. 10A) or FITC-conjugated-2B8T2M (FIG. 10B) at 2 μg/sample and PE-conjugated HLA-DR at 5 μl/sample for 30 minutes.

2B8T2M Retains CD20-Binding, Fc-Receptor Binding and IL-15 Biological Activities In order to verify the CD20-binding properties, FITC-labeled 2B8T2M and rituximab were generated and used to stain human HLA-DR+ B cells. The results indicate that human B cells were able to bind FITC-labeled rituximab (FIG. 10A) as well as FITC-labeled 2B8T2M (FIG. 10B). In contrast, CD20-specific binding activity for these molecules was blocked by unlabeled rituximab and unlabeled 2B8T2M, but not by a non-specific human IgG. These findings demonstrate that 2B8T2M retains the CD20-specific binding activity of rituximab. Similarly, a human histiocytic lymphoma U937 cell line that bears Fc receptors, but not the CD20 or IL-2RβγC on its cell surface was used to evaluate Fc receptor binding of 2B8T2M by flow cytometry. As shown in FIG. 10C, 2B8T2M and rituximab were both able to bind U937 cells, while the Fc-mutant 2B8T2M-LA complex showed reduced binding compared to 2B8T2M.

In previous reports, scTCR-IL-15N72D and scTCR-IL-15N72D:scTCR-IL-15RαSu fusion complexes were shown to retain IL-15 biological activity, although at reduced levels compared to IL-15 (3,8). This lower activity is presumably due to steric hindrance between the fused scTCR domain and IL-15N72D:IL-2RβγC interactions. To assess the IL-15 biological activity of 2B8T2M, an IL-15-dependent cell line, 32Dβ, was used as previously described (3). The results demonstrate that 2B8T2M supported 32Dβ cell proliferation, but exhibited significantly lower activity compared to native IL-15 or ALT-803 (2B8T2M: EC50=889 pM, versus IL-15: EC50=34 pM and versus ALT-803: EC50=14 pM). Taken together, these findings demonstrate that 2B8T2M retains IL-15 biological activity as well as the CD20- and Fc-receptor binding capabilities of rituximab.

Figure 11:
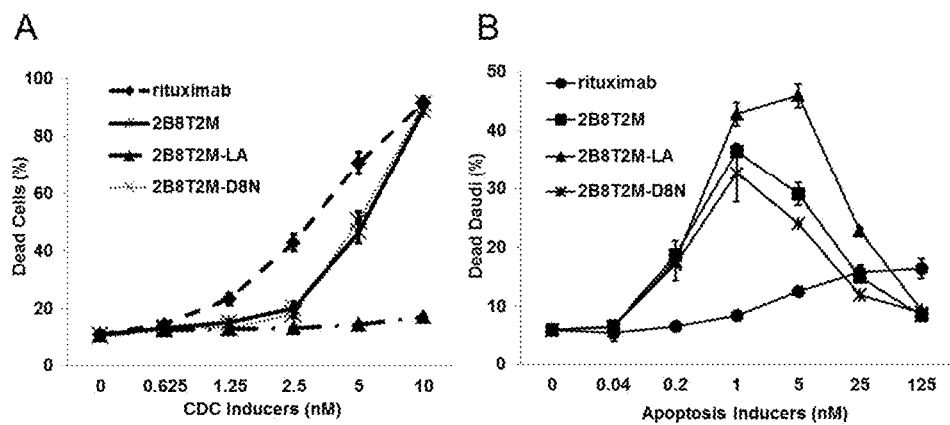
FIG. 11A-FIG. 11B show 2B8T2M induces CDC and apoptosis.

2B8T2M is Capable of Mediating Complement-Dependent Cytotoxicity (CDC) as Well as Direct Apoptosis of CD20+ B-Lymphoma Cells Anti-CD20 antibodies have been grouped into two classes, type I (rituximab-like) and type II (tositumomab-like), based on their ability to form distinct complexes with CD20 and mediate different functional activities on B cells (10). Type I antibody-binding to B cells results in redistribution and clustering of CD20 into lipid rafts, leading to stronger C1q-binding and potent induction of CDC but only low levels of direct antibody-mediated cell-death (i.e., apoptotic activity) (10). In contrast, type II antibodies do not stabilize CD20 in lipid rafts and thus exhibit reduced CDC compared to type I antibodies, but these antibodies potently induce lysosomal cell-death. Rituximab is a type I anti-CD20 mAb, which exhibits higher CDC activity but lower ability to induce apoptosis of B-lymphoma cells than type II anti-CD20 mAbs such as tositumomab (11). 2B8T2M has the same binding-domain as rituximab and is predicted to have similar properties. To investigate this, the ability of 2B8T2M to mediate CDC against CD20+ Daudi cells was assessed. As shown in FIG. 11A, when incubated with 2B8T2M (or the IL-15 mutant 2B8T2M-D8N complex), Daudi cells were lysed in the presence of human complement factors. The Fc-mutant 2B8T2M-LA complex exhibited less CDC activity than 2B8T2M which is expected based on previous results showing lower CDC activity for antibodies containing this Fc-mutant domain (10). Thus, 2B8T2M exhibited CDC activity, although at a lower level than rituximab. To assess the pro-apoptotic activity of 2B8T2M, Daudi cells cultured in media containing 2B8T2M were analyzed for apoptosis using Annexin V staining. Surprisingly, it was found that at a 0.4-10 nM concentration range, 2B8T2M was effective in inducing apoptosis of Daudi cells (FIG. 11B). In contrast, a >600-fold higher concentration of rituximab (i.e., 250 nM) was required to induce comparable apoptotic activity against Daudi cells. This activity was also observed with Fc-mutant 2B8T2M-LA and IL-15-mutant 2B8T2M-D8N complexes (FIG. 11B) but not with c264T2M, indicating that the activity was dependent on CD20-binding. Together, these findings indicate that 2B8T2M exhibits both type I- and type II-like anti-CD20 antibody characteristics.

Figure 12:
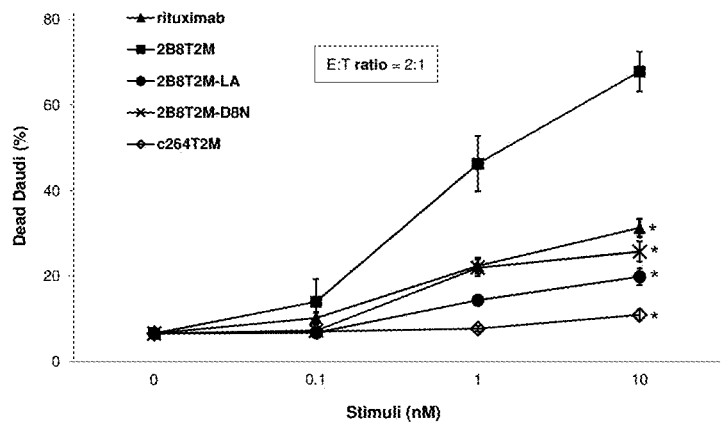
FIG. 12A-FIG. 12D show ADCC Activities of rituximab and 2B8T2M. Daudi cells were labeled with CellTrace Violet and fresh human PBMCs (FIG. 12A, n=5) or purified NK cells (FIG. 12B, n=two donors) were used as effector cells. The effector cells were plated with violet-labeled target cells at indicated Effector:Target ratios with rituximab or 2B8T2M at the indicated concentrations. Target cell viability was assessed on day 2 for PBMCs (FIG. 12A) or day 2 for NK cells (FIG. 12B) by analysis of propidium iodide positive, violet-labeled Daudi cells using flow cytometry. Percentage of dead Daudi cells indicates propidium iodide positive cells. * indicates $p<0.01$ (10 nM) and $p<0.05$ (1 nM) compared to 2B8T2M. Values represent the mean±SE.
Figure 12:
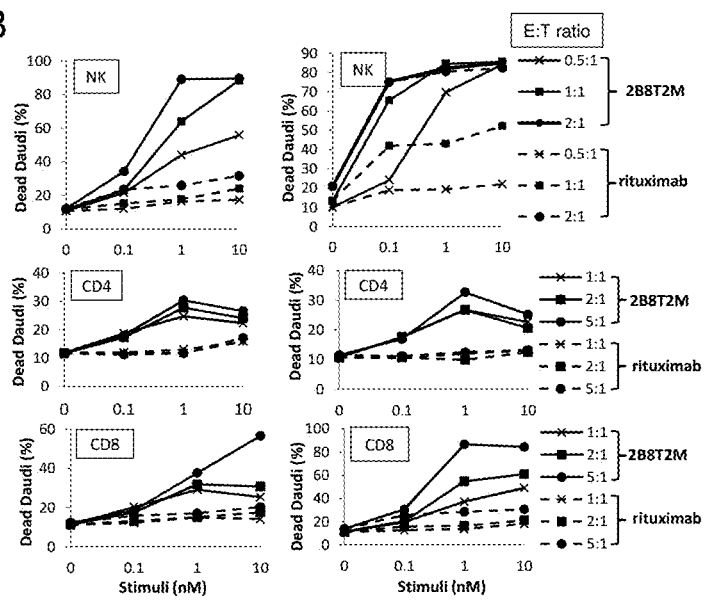
Figure 12:
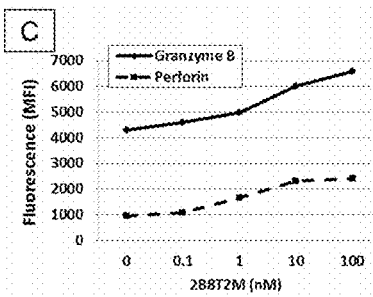
Figure 12:
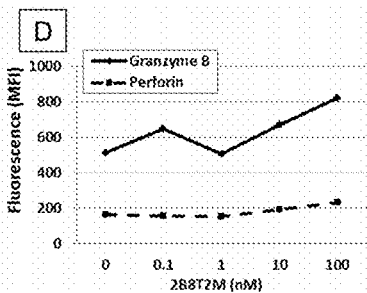

2B8T2M Displays Superior Antibody-Dependent Cellular Cytotoxicity (ADCC) Compared to Rituximab Both type I and II mAbs appear to demonstrate efficient Fc-dependent ADCC against B-lymphoma cell lines (11). However, 2B8T2M may further augment this activity through IL-15-mediated immune cell activation, as supported by previous studies with ALT-803 (7). Thus, the capabilities of 2B8T2M and rituximab to direct ADCC against CD20+ B-lymphoma cells were compared. To evaluate this, human PBMCs were used initially as effector cells and Daudi cells were used as target cells. As shown in FIG. 12A, 2B8T2M was significantly more effective than rituximab at inducing ADCC by PBMCs against Daudi cells. Using other T2M complexes without a functional Fc (2B8T2M-LA), a biologically active IL-15 (2B8T2M-D8N), or a CD20-binding capability (c264T2M), it was further demonstrated that the enhanced ADCC activity of 2B8T2M was dependent in part on each of the anti-CD20 and Fc-binding domains, as well as the IL-15N72D mutant activity (FIG. 12A). To investigate which immune cell subsets play a role in ADCC, CD4+ T cells, CD8+ T cells, and NK cells were sorted and used as effector cells in the same assay. As expected, the results suggest that NK cells are major contributors to ADCC activity of PBMCs, whereas CD8+ and CD4+ T cells play minor to negligible roles (FIG. 12B). In addition, when compared with rituximab, 2B8T2M induced stronger ADCC by all cell subsets against Daudi cells.

To further evaluate the effects of 2B8T2M on the cytotoxic potential of human immune cells, donor PBMCs were cultured in media containing 2B8T2M and granzyme B and perforin levels were evaluated by flow cytometry. 2B8T2M up-regulated granzyme B and perforin expression in NK cells (FIG. 12C), and granzyme B expression in CD8+ T cells (FIG. 12D) in a concentration-dependent manner Perforin expression in CD8+ T cells was only slightly higher with addition of 200 nM of 2B8T2M (FIG. 12D). Granzyme B and perforin upregulation by CD4+ T cells was negligible or absent.

Figure 13:
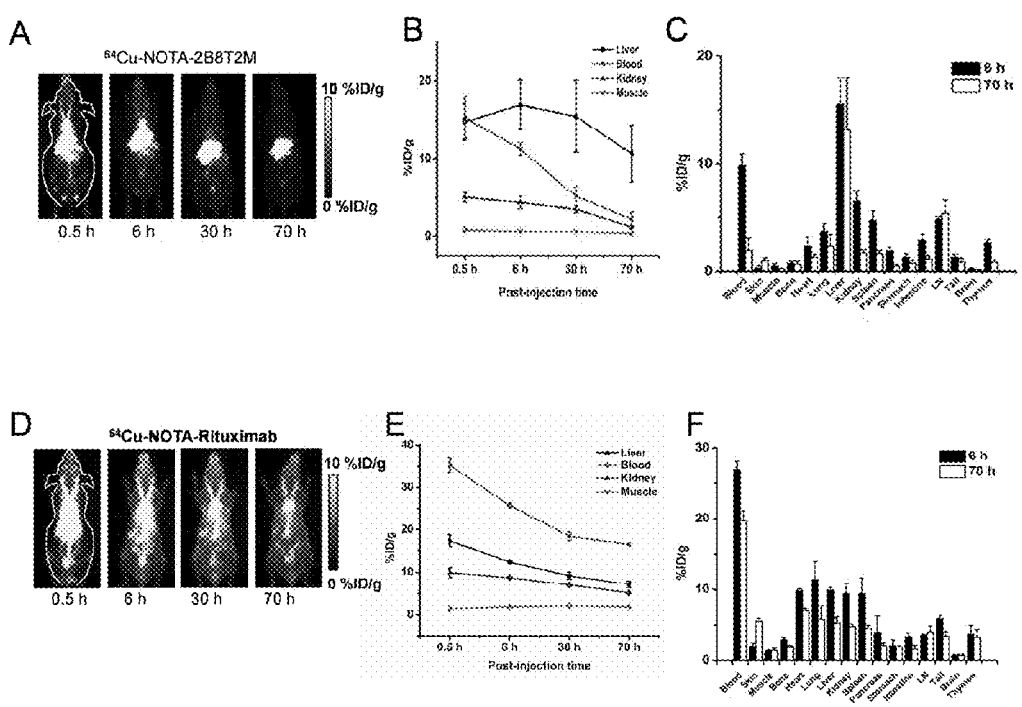
FIG. 13A-FIG. 13F show quantitative analysis of the PET imaging data of 2B8T2M, with rituximab as a control.

Visual and Quantitative Measures of Pharmacokinetics and Biodistribution of 2B8T2M Serial non-invasive PET scans were used as visual and quantitative measures of the whole body distribution and pharmacokinetics of 64Cu-labeled 2B8T2M and 64Cu-labeled rituximab. Previous biodistribution studies of mice administered 64Cu-labeled ALT-803 compared with 64Cu-IL-15 showed distinct pharmacokinetic profiles demonstrating rapid clearance of 64Cu-IL-15 through the renal pathway whereas ALT-803 clearance occurred in the liver but was retained for at least 70 hours in the lymphoid organs (12). In this study, 64Cu-NOTA-2B8T2M was cleared from the mouse body through both the hepatobiliary and renal pathways and kidney uptake was low (FIG. 13A-FIG. 13C). The uptake of 64Cu-NOTA-2B8T2M in the lymph nodes was comparable to what was previously observed with 64Cu-NOTA-ALT-803 (12), which demonstrated the high IL-15 receptor-targeting efficiency for both of these fusion proteins. At 6 hours post-injection (p.i), the lymph node uptake of 64Cu-NOTA-2B8T2M remained persistent at 4.2±0.5 percent injected dose per gram of tissue (% ID/g) and 5.3±1.3% ID/g even at 70 hours p.i., due to the relatively longer circulation half-life (184 hours) compared to ALT-803 (18 hours) in mice (4). In comparison, 64Cu-NOTA-rituxmab exhibited longer blood circulation than 64Cu-2B8T2M with a different biodistribution profile. The lymph node uptake of 64Cu-NOTA-rituximab was lower (3.5±0.2% ID/g at 6 hours p.i. and 4.1±0.8% ID/g at 70 hours p.i.; FIG. 13B), whereas the uptake in blood and muscle was higher, generating higher background signal (FIG. 13D-FIG. 13F). This result suggests that the ALT-803 protein scaffold provides a vehicle to preferentially deliver 2B8T2M to the lymphoid tissues.

Proliferation of NK Cells and CD8+ T Cells in Vivo is Induced by 2B8T2M

Figure 14:
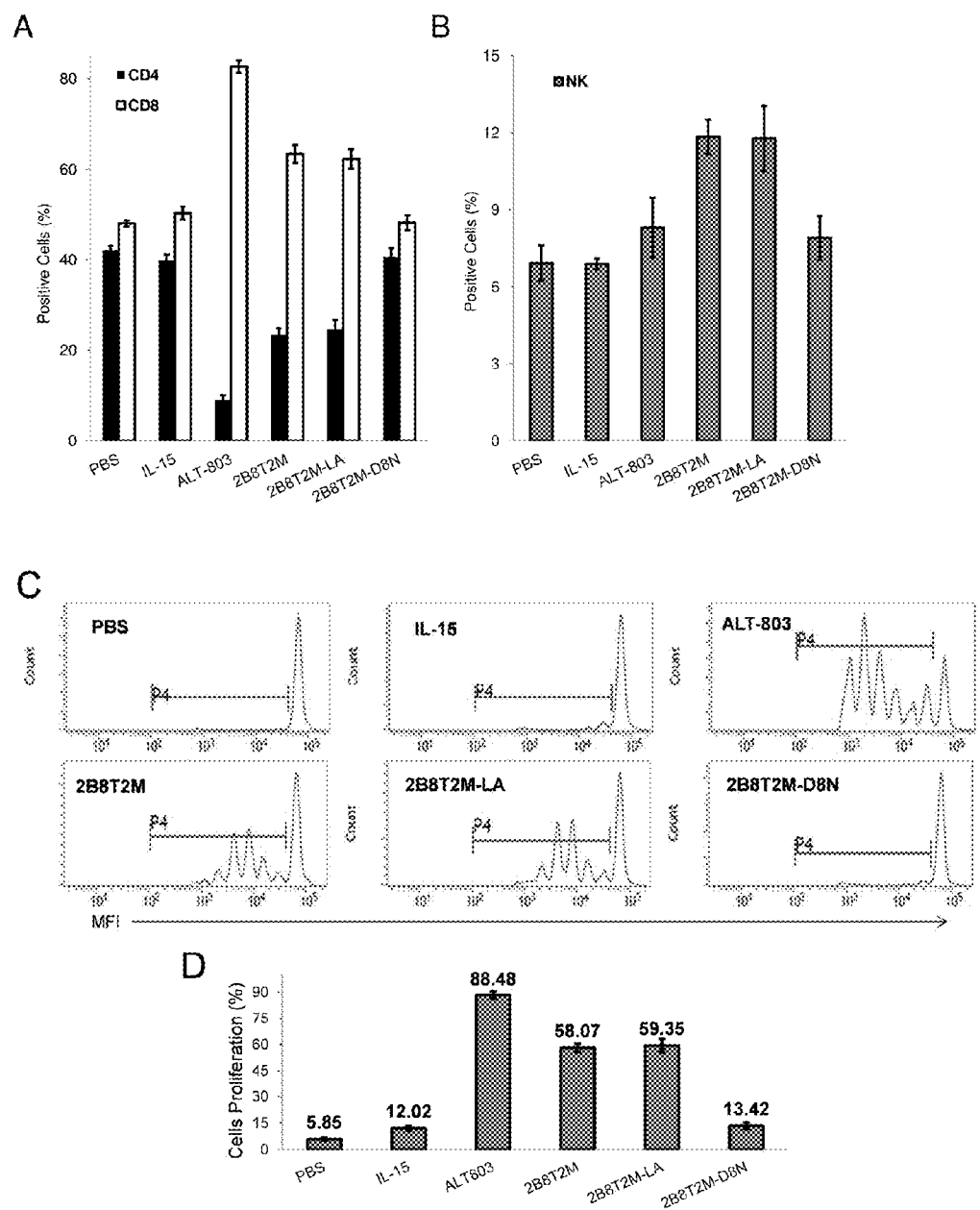
FIG. 14A-FIG. 14D show expansion CD8$^+$ T Cells and NK Cells induced by 2B8T2M. CellTrace Violet-labeled enriched syngeneic T cells ($1 \times 10^7$/mouse) were adoptively transferred into C57BL/6 female recipients (n=5 or 6/group). On day 2 post-transfer, 2B8T2M (5 mg/kg), 2B8T2M-LA (5 mg/kg), 2B8T2M-D8N (5 mg/kg), IL-15 (0.056 mg/kg), and PBS were i.v. injected.

Previous studies demonstrated that the ALT-803 complex exhibits significantly stronger immune cell stimulation in vivo compared to IL-15 (4). To evaluate the immunostimulatory activity of 2B8T2M in comparison with ALT-803, IL-15, and other T2M complexes in vivo, CD3+ T cells and NK cells were isolated and labeled with CellTrace Violet. The enriched, violet-labeled CD3+ T cells and NK cells were adoptively transferred i.v. into C57BL/6 female mice and the mice were treated on day 2 post-transfer with either PBS control, 2B8T2M, 2B8T2M-LA, 2B8T2M-D8N, ALT-803, or a molar-equivalent dose of free IL-15. On day 5 post-transfer, the violet positive cells in mouse spleens were assessed by flow cytometry. As shown in FIG. 14A, 2B8T2M-treated mice exhibited significantly higher proportion of CD8+ T cells in the spleen than IL-15- or PBS-treated mice (p<0.001) but significantly less CD8+ T cells than the ALT-803 treatment group (p<0.001). Mice which received 2B8T2M also showed a larger percentage of NK cells in the spleen compared to IL-15- or PBS-treated mice (p<0.001; FIG. 14B). Compared to IL-15- or PBS-treated mice, CD4+ T cell percentages in the spleen were relatively reduced in 2B8T2M-treated mice (FIG. 14A). Treatment of mice with the Fc-mutant 2B8T2M-LA showed the same increased percentages of adoptively transferred NK cells and CD8+ T cells in the spleen as seen in the 2B8T2M treatment group, whereas treatment with the IL-15-mutant, 2B8T2M-D8N, did not show similar effects. This result indicates that the IL-15N72D domain was responsible for the changes in these immune cell subsets.

It was further examined the proliferation of donor CD8+ T cells and NK cells in spleens of recipient mice. As shown in FIG. 14C and FIG. 14D, treatment with 2B8T2M resulted in increased proliferation of adoptively transferred cells compared to treatment with IL-15 or PBS; however, proliferation post 2B8T2M treatment was lower than following ALT-803 treatment. Consistent with the effects on splenic immune cell subsets, the Fc-mutant 2B8T2M-LA had similar immunoproliferative activity as 2B8T2M, whereas treatment with the IL-15-mutant, 2B8T2M-D8N, resulted in little to no proliferation of the adoptively transferred lymphocytes in vivo.

Figure 15:
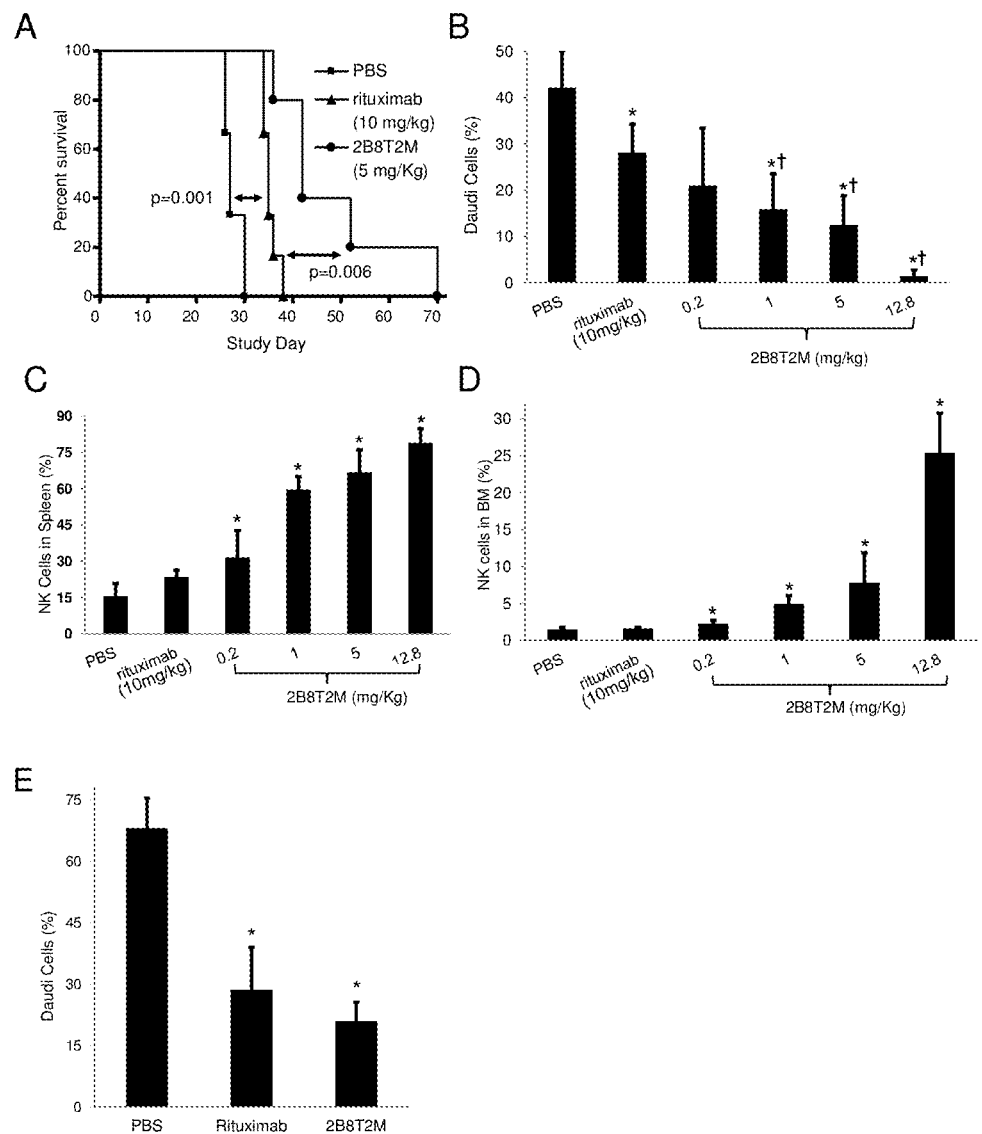
FIG. 15A-FIG. 15E show prolonged survival of tumor-bearing mice treated with 2B8T2M and efficacy of 2B8T2M antitumor activity.

Superior Efficacy of 2B8T2M Against Daudi B-Lymphoma in SCID Mice Compared with Rituximab To compare the overall in vivo antitumor activities of 2B8T2M and rituximab, the Daudi B-lymphoma/SCID mouse model was employed. Daudi cells (1×107) were injected i.v. into female SCID mice and 15 days post-inoculation the presence of tumor cells in the bone marrow was verified by flow cytometry using PE-conjugated anti-human HLA-DR antibody (i.e., two mice showed 0.5% and 2.8% Daudi cells in bone marrow). The remaining Daudi-bearing mice were randomized into 3 groups and treated on day 15 and day 18 with rituximab at 10 mg/kg (equivalent to a clinical-dose of 375 mg/m2 for non-Hodgkin's lymphoma (NHL) patients), 2B8T2M at 5 mg/kg, or PBS as vehicle control. Hind-leg paralysis was used as survival end-point for this study. As shown in FIG. 15A, the median survival times for PBS-, rituximab-, and 2B8T2M-treated mice were 27, 35, and 42 days, respectively. While rituximab significantly improved the survival of Daudi-bearing mice compared to PBS control group (p=0.001), 2B8T2M treatment further prolonged survival relative to rituximab (p=0.006).

In a follow-up dose-response study, Daudi-bearing mice were randomized into 6 groups and treated on days 15 and 18 post-inoculation with 10 mg/kg rituximab; 12.8 (molar equivalent to 10 mg/kg rituximab), 5, 1, or 0.2 mg/kg 2B8T2M; or PBS as vehicle control. Daudi-tumor burden in the bone marrow was determined on day 22 by flow cytometry. As shown in FIG. 15B, the percentage of Daudi cells in bone marrow of rituximab-treated mice was significantly lower than the PBS control group (p=0.003). Moreover, treatment of mice with 1, 5, or 12.8 mg/kg 2B8T2M resulted in significantly lower Daudi-tumor burden in the bone marrow than was observed in the rituximab-(p<0.01) or PBS-treated groups (p<0.001), whereas the equivalent reduction in bone marrow Daudi cells was seen in the 0.2 mg/kg 2B8T2M- and rituximab-treated groups (p=0.24). In addition to Daudi cells, the percentage of NK cells in bone marrow and spleens was assessed by flow cytometry. As shown in FIG. 15C and FIG. 15D, there was no difference in NK cell percentages in bone marrow of rituximab- and PBS-treated mice. However, 2B8T2M-treated mice at all doses exhibited significantly higher proportions of NK cells in bone marrow and spleens compared to PBS control mice (p<0.05). The increased levels of NK cells may be a major contribution to the potent antitumor activity of 2B8T2M. To assess whether NK cells are essential for 2B8T2M's antitumor activity, similar animal studies were conducted in SCID-beige mice, which are genetically diminished of NK cell activity compared with SCID mice (FIG. 15E). Daudi-bearing SCID-beige mice were randomized into 3 treatment groups and treated with 10 mg/kg rituximab, 5 mg/kg 2B8T2M, or PBS as vehicle control. Surprisingly, Daudi cells percentage was still significantly lower (p<0.01) in bone marrow of 2B8T2M- and rituximab-treated mice compared to control, indicating that NK cells are not essential for the antitumor activity of 2B8T2M or rituximab. This further suggests that while 2B8T2M induces antitumor activity through ADCC, the in vivo antitumor activity of this fusion protein is retained by its apoptotic effects and CDC against tumor cells in mouse with diminished NK cell activity. Macrophages and neutrophils are also known to exhibit ADCC and antibody dependent cellular phagocytosis (ADCP) functions (13). It is possible that macrophages and neutrophils contribute to antitumor activity of this fusion protein in the SCID-mice. Additionally since the efficacy of 2B8T2M in this model is reduced in comparison to that in the Daudi SCID mouse model, it is likely that NK cells do play a role in augmenting the antitumor activity of 2B8T2M.

Figure 16:
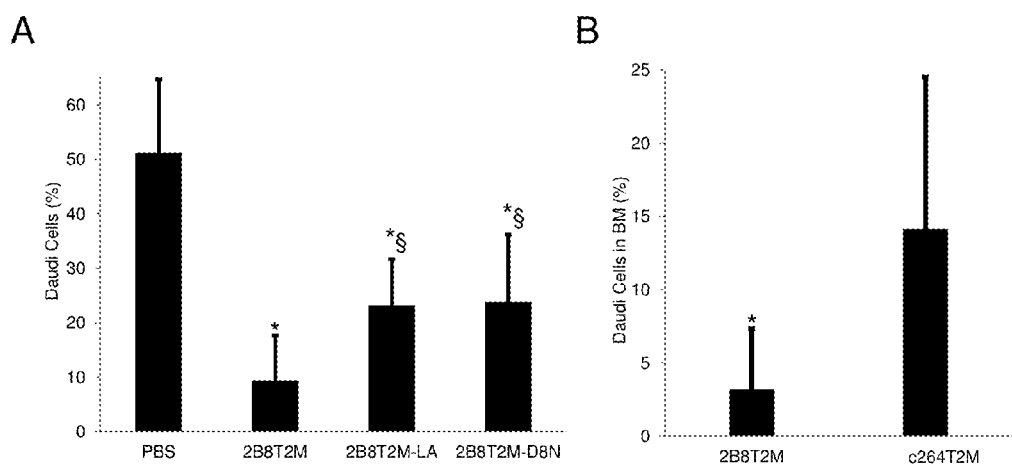
FIG. 16A-FIG. 16B show comparison of antitumor functions of different muteins of 2B8T2M.

Antitumor Activities of Various Domains of 2B8T2M Against Daudi B-Lymphoma in SCID Mice In order to dissect the functions of the different domains of 2B8T2M, the antitumor activities of 2B8T2M, Fc-mutant 2B8T2M-LA, and IL-15-mutant 2B8T2M-D8N were compared in the Daudi B-lymphoma/SCID mouse model. As shown in FIG. 16A, all test agents administered at 5 mg/kg significantly reduced Daudi tumor burden in bone marrow compared to PBS-treated group. Additionally, Fc-mutant 2B8T2M-LA and IL-15-mutant 2B8T2M-D8N were less effective at reducing Daudi-tumor burden in bone marrow than 2B8T2M (p<0.05). Furthermore, the c264T2M was used as a non-targeting control complex in a separate experiment and was found to be less effective at reducing Daudi cell percentages in the bone marrow than 2B8T2M (FIG. 16B). Taken together, these findings indicate that IL-15-mediated immune activation, Fc-domain activity, and 2B8-specific targeting of CD20 were all important contributors to the effective in vivo antitumor activity of 2B8T2M against Daudi B-lymphoma.

B-Cell Depletion by 2B8T2M in Cynomolgus Monkeys

Figure 17:
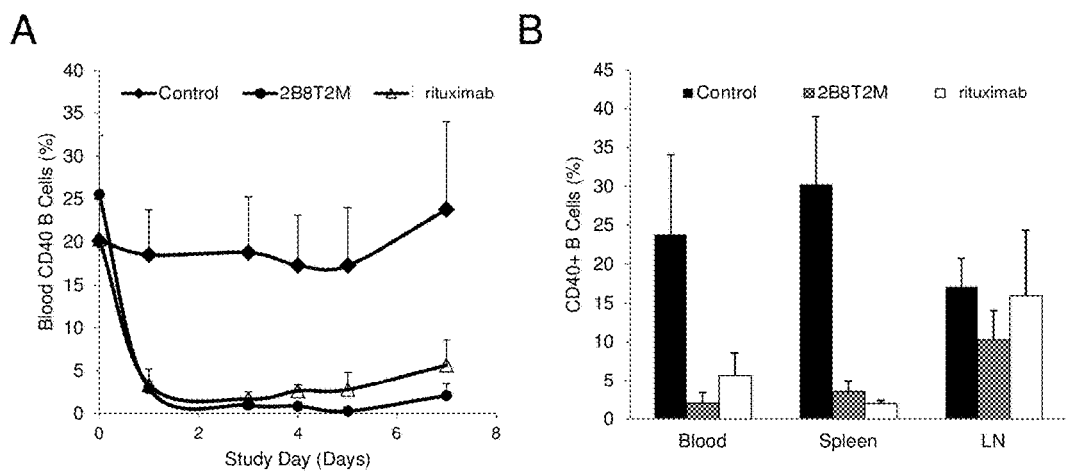
FIG. 17A-FIG. 17B show B cell-depletion by 2B8T2M in cynomolgus monkeys. The study consisted of 3 groups of cynomolgus monkeys with 4 male animals in each group. The animals were treated with i.v. 2B8T2M at 5 mg/kg, rituximab at 10 mg/kg, and PBS vehicle control. The same treatment was repeated after 3 days. Blood samples for B cell analysis (FIG. 17A) were obtained pre-treatment, 1 day (24 hours) post-first treatment, 3 days post-first treatment and pre-second treatment, 4 days (24 hours post-second treatment), 5 and 7 days post-first treatment. All cynomolgus monkeys were euthanized 7 days post-first treatment and the spleen and mesenteric lymph nodes (LN) cells were harvested for B cell analysis by flow cytometry (FIG. 17B).

Following the efficacy studies of 2B8T2M in the Daudi B-lymphoma/SCID mouse model, the ability of 2B8T2M to deplete B cells was further investigated in cynomolgus monkeys. Animals (n=4/group) were injected i.v. with 5 mg/kg 2B8T2M, 10 mg/kg rituximab, or PBS as vehicle control on days 0 and 3, followed by euthanization on day 7. The spleens and mesenteric lymph nodes were collected and assessed for levels of B cells and other lymphocyte subsets by flow cytometry. Changes in B cell percentages in peripheral blood were also determined using samples taken before dosing and on days 1 (24 hours post-first dosing), 3 (pre-second dosing), 4 (24 hours post-second dosing), 5 and 7. As shown in FIG. 17A-FIG. 17B, B cells in peripheral blood were effectively depleted in both 2B8T2M- and rituximab-treated groups one day after the first dose. Following the second dose, B-cell levels in peripheral blood of 2B8T2M-treated animals were further reduced compared to rituximab-treated animals, however this effect was not always statistically significant (p=0.004 on day 4, p=0.051 on day 5, and p=0.067 on day 7). Interestingly, percentage of B cells in lymph nodes of 2B8T2M-treated monkeys was significantly lower than the PBS-treated group. However, there was no significant difference between rituximab-treated group and PBS-treated group. Treatment with 2B8T2M resulted in a significant increase in the percentage of lymph node NK cells (2.4-fold vs. control) and a decrease in the percentage of blood CD8+ and CD4+ T cells (0.8- and 0.5-fold vs. control, respectively) and splenic CD4+ T cells (0.4-fold vs. control), presumably due to the immunostimulatory effects of the IL-15N72D domain on immune cell proliferation and trafficking. In contrast, rituximab treatment resulted in a 1.4 to 1.8-fold increase in splenic CD8+ and CD4+ T cell percentages (p<0.05), likely as a compensatory effect to the loss of B cells. No significant adverse effects were observed in either 2B8T2M or rituximab treatment groups.

Monoclonal antibodies (mAbs) recognizing specific antigens on tumor cells are currently used as cancer therapy. Rituximab, targeting the CD20 antigen expressed on >90% of non-Hodgkin's lymphoma (NHL), has been successfully used in patients for over a decade. The mechanisms of action of anti-CD20 mAbs have involved apoptosis induction, ADCC, CDC, and phagocytosis of target cells (14). The antitumor activity of mAbs is mainly through ADCC, which can be further improved with adjuvant therapy that enhances activation of effector cells. IL-15 is a potent stimulant and activator of CD8+ T and NK cells and is an emerging cancer immunotherapeutic agent that can be combined with mAbs to enhance NK cell-mediated ADCC (15). An IL-15 super-agonist, ALT-803, a complex of an IL-15N72D mutant and a dimeric IL-15RαSuFc fusion protein was created. ALT-803 exhibits superior activity in vitro and in vivo. The N72D mutation increases IL-15's biological activity ~5-fold, and the IL-15N72D:IL-15RαSuFc complex further enhances IL-15's activity ~25-fold, compared to native IL-15 in vivo (3,4). Also, ALT-803 has greater binding activity with the IL-2RβγC complex displayed on the surface of immune cells, a substantially longer serum half-life, and better biodistribution and retention in lymphoid tissues than native IL-15 (3,4,12). Exhibiting potent immunostimulatory and antitumor properties, ALT-803 is an effective agent against various tumors in animal models either as a single agent or in combination with other therapies (5,6). For example, ALT-803 stimulation significantly increased rituximab-mediated ADCC by human NK cells against B-cell lymphoma cell lines or primary follicular lymphoma cells in vitro. Moreover, in two different B-cell lymphoma mouse models, the addition of ALT-803 to anti-CD20 mAb therapy provided significantly reduced tumor cell burden and increased survival (7). As a result, ALT-803 is currently in multiple clinical trials against solid and hematological malignancies (relapse of hematologic malignancy after allogeneic stem cell transpinatation, refractory multiple myeloma, and indolent non-Hodgkin lymphoma; NCT01885897, NCT02099539, and NCT02384954, respectively). In the studies described herein, it was further demonstrated that ALT-803 can be modified as a versatile protein scaffold for the creation of novel multivalent antigen-specific immunotherapeutic complexes. A targeted immunotherapeutic referred to as 2B8T2M was constructed. This fusion protein consists of the recognition domain of rituximab and IL-15N72D:IL-15RαSuFc, and is able to mediate ADCC and CDC against B-lymphoma, while exhibiting pro-apoptotic activity and in vivo immune cell stimulation. Thus, the 2B8T2M complex as a single molecule retains the anti-CD20 properties of rituximab in addition to the immunostimulatory properties of ALT-803. When compared with rituximab, 2B8T2M demonstrates improved antitumor activity and results in prolonged survival of SCID mice bearing Daudi B-lymphoma. Furthermore, increased proportions of NK cells in 2B8T2M-treated mice suggest that NK cells play a pivotal role in the enhanced antitumor activity of 2B8T2M in vivo. To further assess whether NK cells are essential for 2B8T2M's antitumor activity, similar animal studies were conducted in SCID-beige mice, which are deficient in NK cells. Surprisingly, Daudi cells percentage was still significantly lower in bone marrow of 2B8T2M-treatred mice compared to vehicle control. This suggests that the in vivo antitumor activity of this fusion protein can be retained by its apoptotic effects and CDC in mouse with diminished NK cell activity. Macrophages and neutrophils are also known to exhibit ADCC function (13). It is possibile that macrophages and neutrophils can replace the ADCC function of NK cells for this fusion protein in the SCID-beige mice. Unlike the results from SCID mouse studies, there is no significant differnce in antitumor activity between 2B8T2M and rituximab in SCID-beige mice. Therefore, NK cells enhanced the 2B8T2M antitumor activity in vivo. It is conceivable that this is the result of the IL-15 component of 2B8T2M which expanded the NK cell popoulation and/or up-regulated the ADCC functions of NK cells.

Anti-CD20 mAbs have been effectively used in the treatment of NHL. Type I and II anti-CD20 antibodies are each capable of recruiting FcR-expressing cells to mediate ADCC and phagocytosis directed against CD20+ cells (16). Importantly, both type I and II antibodies have been approved for clinical use based on their activities against various CD20+ B-lymphomas or B-cell-mediated autoimmune diseases (17, 18). As shown in this study, 2B8T2M retains rituximab-like CDC against CD20+ target cells while exhibiting enhanced apoptotic activity. These findings indicate that 2B8T2M possesses the functional advantages of both type I and II anti-CD20 antibodies with the addition of strong enhancement of ADCC through IL-15-based immunostimulatory activity for potent NK cell effector responses. The pro-apoptotic activity of 2B8T2M is dependent on the CD20-binding domain but not on FcR-binding or IL-15 activity. Previous studies have shown that chemically cross-linked rituximab homodimers and recombinant tetravalent rituximab scFv-Ig fusions had superior apoptosis-inducing activity against B-lymphoma cells than monomeric rituximab (19,20). These results suggest that the enhanced pro-apoptotic activity of 2B8T2M compared to rituximab is also likely due to its multivalent-binding capability to CD20+ cells.

ALT-803 induces memory CD8+ T cells to proliferate, upregulate NKG2D, secrete IFN-γ and acquire the ability to kill malignant cells in the absence of antigenic stimulation (5,21). The results presented herein indicate that the CD20-specific complex, 2B8T2M, retains the unique capability of ALT-803. For instance, the adoptive transfer experiments showed that 2B8T2M promoted the expansion of memory CD8+ T cells and NK cells. Thus, anti-CD20 scFv domains of 2B8T2M did not alter the biological effects of the ALT-803 component on memory CD8+ T cells, although the scFv domains lowered the relative IL-15 activity approximately 60-fold compared to ALT-803. The decrease in IL-15 activity of 2B8T2M is likely due to the steric hindrance of the anti-CD20 single chain Ab affecting the binding-domain of IL-15N72D to IL-2RβγC since similar effects were seen with other IL-15 fusions (3,8). The lower IL-15 activity of these fusion molecules may enhance the clinical utility of this type of molecule in general. It has been shown that one of the determining factors of ADCC effectiveness of an antibody is concentration, which affects its bound density on the target cells (22). The lower IL-15 activity of these fusion molecules may potentially enable their administration at a higher dose level for effective ADCC without inducing unwanted immune-related systemic toxicities. The ADCC-dependent efficacy and well-tolerated safety profile of 2B8T2M both in murine and non-human primate models shown in this study demonstrate this point and support the clinical utility of these molecules.

In a comparative biodistribution study with native IL-15, ALT-803 was distributed to and retained better in lymphoid organs of mice (12). Similarly, 2B8T2M biodistribution data indicates uptake and retention in lymphoid tissues for at least 70 hours. In the CD40+ B-cell depletion study in non-human primates, it was found that lower dose levels of 2B8T2M were more efficacious than rituximab, particularly in the lymph nodes. 2B8T2M treatment also induced a significant increase in the percentage of lymph node NK cells compared to controls. It is conceivable that 2B8T2M was retained in the lymphoid tissues, potentially stimulating T and NK cells for a significant period of time through its IL-15 component, whereas rituximab lacked this activity. This stimulation of NK cells, likely due to the induction of perform and granzyme B (23), may have significantly enhanced the ADCC against B cells. Thus, these fusion molecules may be particularly effective against B-cell lymphoma.

ADCC of therapeutic antibodies have also been demonstrated to induce an adaptive immune response against a targeted antigen displayed on cancer cells via the "vaccinal effect" (14,24-26). This effect is Fc-dependent and provides a durable memory response for the host through tumor rejection following re-challenge (27). IL-15, a component of 2B8T2M, is a key cytokine for the development of effector and memory CD8+ T cells. Thus, it is conceivable that the IL-15 component of the 2B8T2M molecule can enable a stronger "vaccinal effect" than a therapeutic antibody alone against the targeted antigen by activating the immune responses of CD8+ T cells. Also, it should be noted that the ALT-803 scaffold enhanced the lymphoid tissue retention of the rituximab binding domains. Thus, the ALT-803 scaffold may represent a vehicle to deliver the fusion components to the lymph organs for immune system activation.

These studies show that a scaffold molecule based on IL-15N72D:IL-15RαSuFc could potentially be fused to multiple target-recognition domains derived from antibodies, adhesion molecules, or other receptors. With the appropriate target domain, the resulting complexes could promote conjugation of various immune effector cells and mediate destruction of target cells, including cancer cells or virally-infected cells displaying specific targets. The IL-15 domain of the complex could provide immunostimulatory activity to support effector cell proliferation and cytotoxicity. This single fusion protein approach would also eliminate the need for complicated treatment regimens employing combination immunotherapies. Therefore, the IL-15N72D:IL-15RαSuFc scaffold complex may offer a unique opportunity to utilize the promising potential of IL-15 as a targeted-immunotherapeutic drug against cancer and infectious diseases.

The following experimental procedures were utilized for this example.

Mice and Cell Lines

FOX Chase SCID (C.B-17/IcrHsd-Prkdc-scid), SCID-beige (C.B-17/IcrHsd-PrkdcscidLystbg-J) and C57BL/6NHsd mice (6-8 week old females, Harlan Laboratories) were housed in Altor BioScience's animal facilities. All animal studies were performed according to National Institutes of Health (NIH) animal care guidelines under Institutional Animal Care and Use Committee (IACUC)-approved protocols.

Human Daudi B-lymphoma cell line was purchased from American Type Culture Collection (ATCC) and routinely cultured in complete Roswell Park Memorial Institute (RPMI)-1640 medium at 37° C. with 5% $CO_2$. Prior to use in these studies, the Daudi cells were authenticated in 2014 and 2015 by confirming cell growth morphology (lymphoblast), growth characteristics, phenotype of uniform expression of human CD20 by flow cytometry, and functionally as anti-CD20 mAb opsonized targets for ADCC. IL-15-dependent 32β cells (3) were cultured in complete Iscove's Modified Dulbecco's Media (IMDM) supplemented with 1-2 ng/ml IL-15 (kindly provided by Dr. J. Yovandich, National Cancer Institute-Frederick, Md.).

Generation of Sc2B8 Fusion Constructs

To generate a soluble single-chain two-domain anti-CD20 mAb construct (sc2B8), the V-gene segments of 2B8 mAb light and heavy chains were cloned from the 2B8 hybridoma (ATCC). The VL gene segment was fused to the 5' end of the VH gene segment via a linker (Gly4Ser)3. The sc2B8 gene was fused to the 5' end of IL-15 mutein sequences including: (1) IL-15 superagonist (IL-15N72D), (2) IL-15 antagonist (IL-15D8N), as well as the 5' end of a fusion construct (IL-15RαSuFc) as previously described (3). To generate the FcR-binding-deficient mutein, the sc2B8 was fused to IL-15RαSuFc-LA of which the hIgG1 heavy chain amino acids 234 and 235 were mutated from leucine to alanine (10). A soluble single-chain three-domain T cell receptor (TCR), c264scTCR (chimeric human p53 (264-272) specific single-chain TCR), was also constructed as previously described (3,8). Similar to the sc2B8 fusions, the c264scTCR was fused to IL-15N72D or IL-15RαSuFc to make c264scTCR-IL-15N72D and c264scTCR-IL-15RαSuFc constructs. The resulting sc2B8-IL-15N72D:sc2B8-IL-15RαSuFc (2B8T2M), sc2B8-IL-15D8N:sc2B8-IL-15RαSuFc (2B8T2M-D8N), sc2B8-IL-15N72D:sc2B8-IL-15RαSuFc-LA (2B8T2M-LA), and c264scTCR-IL-15N72D:c264scTCR-IL-15RαSuFc (c264T2M) genes were expressed in pMSGV retroviral vector (28).

Fusion Protein Production and Purification

Expression vectors containing the various constructs were transfected into CHO cells from ATCC followed by selection in medium containing appropriate antibiotics. For production of the fusion proteins, the recombinant CHO cells were grown in serum free defined medium (SFM4CHO, Hyclone, Logan, Utah) at 37° C. When the viable cell density of the cultures reached a maximum, the incubation temperature was shifted down to 30° C. for 10-14 days for accumulation of the soluble complex. The fusion proteins were purified from the recombinant CHO cell culture supernatants by immunoaffinity Protein A chromatography. Prior to sample loading, the column was washed with 5 column volumes (CV) of 20 mM Tris-HCl, pH 8.0, sanitized with 5 CV of 0.1 N NaOH for 1 hour, and then equilibrated with 7 CV of 20 mM Tris-HCl, pH 8.0. The supernatant was loaded onto the column at 2 mL/min, and the column was then washed with 8 CV of 20 mM Tris-HCl, pH8.0, followed by 7 CV of washing buffer (0.1 M Na-citrate, pH 5.0) to remove non-specifically bound proteins. The protein was then eluted with 0.2 M Na-citrate, pH 4.0 and the pH of collected peak fractions was immediately neutralized by using 2 M Tris-HCl, pH 8.0. The preparation was concentrated and buffer exchanged into phosphate-buffered saline (PBS) by using an Amicon Ultra-15 centrifugal concentrator (30 kDa cutoff, Millipore, Billerica, Mass.). Aggregates within the purified fusion proteins were removed by size-exclusion chromatography. The purified fusion proteins were analyzed by reducing SDS polyacrylamide gel electrophoresis (SDS-PAGE) (12% Bis Tris gel) followed by SimplyBlue™ Safe Stain (Invitrogen). Homogeneity of 2B8T2M molecules was characterized by size-exclusion chromatography. The fusion proteins are stable at 4° C. for at least 12 months (data not shown).

Flow Cytometry Analysis

To verify the CD20-binding properties of 2B8T2M, peripheral blood mononuclear cells (PBMCs) were stained with FITC-labeled 2B8T2M or rituximab and the binding-specificity was demonstrated by blocking with unlabeled 2B8T2M or rituximab. To verify the Fc-receptor binding of 2B8T2M, a human histiocytic lymphoma U937 cell line (ATCC) was stained with FITC-labeled 2B8T2M, rituximab or 2B8T2M-LA. The stained PBMCs and U937 cells were analyzed on a FACSVerse using FACSuite software (BD Biosciences).

Cell Proliferation Assays

Proliferation of 32Dβ cells was measured as previously described (3,8). Briefly, 32D13 cells (1×10⁴ cells/well) were incubated with fusion proteins for 48 hours at 37° C. Cell proliferation reagent, WST-1 (Roche Applied Science), was added during the last 4 hours. Conversion of WST-1 to the colored formazan dye was determined through absorbance measurements at 450 nm. The EC50 was determined based on the dose-response curve using Prism4 software (GraphPad Software).

In Vitro Cytotoxicity Assays

CDC assay-Daudi cells were incubated in RPMI-10 in the presence of 2B8T2M, its muteins, or rituximab at 37° C. for 2 hours. Normal human serum (Innovative Research) was used for complement reactions. Viability of Daudi cells was determined by propidium iodide (Sigma) staining and analyzed on a BD FACSVerse.

ADCC Assay

Daudi cells were labeled with CellTrace Violet (Invitrogen) according to the manufacturer's instructions and served as target cells. Fresh human PBMCs or MACS purified NK cells were isolated from blood buffy coat (OneBlood) and used as effector cells. The effector cells were mixed with Daudi cells at the indicated Effector:Target ratios in the presence of 2B8T2M, its muteins, or rituximab. Following a 2-3 day incubation at 37° C. with 5% CO2, Daudi cell viability was assessed by propidium iodide (Sigma) staining and analyzed on a BD FACSVerse.

Apoptosis Assay

Daudi cells were incubated in RPMI-10 in the presence of 2B8T2M, its muteins, or rituximab at 37° C. for 3 days. On day 3, Daudi cells were stained with FITC-conjugated Annexin V (BioLegend) and percent apoptotic Daudi cells was analyzed on a BD FACSVerse.

Positron Emission Tomography (PET) Imaging and Tissue Biodistribution Studies

C57BL/6 mice were injected intravenously (i.v.) with 10-15 MBq of 64Cu-labeled 2B8T2M and 64Cu-NOTA-rituximab. Static PET scans were performed on anesthetized animals at various time points post-injection using an Inveon microPET/microCT rodent model scanner (Siemens). Data acquisition, image reconstruction, and region-of-interest analysis to calculate the percentage injected-dose per gram of tissue (% ID/g) for major organs were conducted as previously described (29,30). The radioactivity in each tissue was measured using a gamma-counter (Perkin Elmer) and presented as % ID/g.

Tumor Models

Following i.v. injection with 1×10⁷ Daudi cells/mouse, tumor-bearing FOX Chase SCID or SCID-beige mice were closely monitored for hind-leg paralysis, which served as the survival end-point. The percentage of Daudi cells in bone marrow was determined by flow cytometry (FACSVerse) using PE-conjugated anti-human HLA-DR antibody (BioLegend).

T Cell Labeling and Adoptive Transfer

CD3+ enriched cells (CD3 Enrichment Column, R&D Systems) from spleens and lymph nodes of donor C57BL/6NHsd mice were labeled with CellTrace Violet (Invitrogen) according to the manufacturer's instructions. On study day 0 (SD0), 1×10⁷ violet-labeled cells were adoptively transferred into syngeneic C57BL/6NHsd mice. On SD2, mice were treated i.v. with the test articles. On SD5, spleens were harvested and analyzed by flow cytometry for donor lymphocyte proliferation (violet-labeled) and lymphocytic subset composition.

Cynomolgus Monkeys Studies

Male cynomolgus monkeys (2.20-2.85 kg, 2-3 years) were provided by Yunnan Laboratory Primate, Inc. (Kunming, China). This study was conducted in accordance with a research proposal approved by the IACUC of Yunnan Laboratory Primate, Inc. On study days 0 and 3, 2B8T2M was administered i.v. at 5 mg/kg, rituximab at 10 mg/kg, and PBS served as treatment control. On day 7, the monkeys were euthanized and spleens and mesenteric lymph nodes were harvested and processed for immune cell analysis. Blood samples were taken at pre-dosing and on day 1 (24 hours post-dosing), 3 (pre-dose 2), 4 (24 hours post-dosing), 5, and 7.

Data Analysis

Survival data was analyzed using the Kaplan-Meier method. Comparisons of continuous variables were done using Student's t tests or ANOVA (two-tailed) (GraphPad Prism4). P values ≤0.05 were considered significant.

The following references were cited in this example.

REFERENCES

1. Fehniger, T. A., and Caligiuri, M. A. (2001) Interleukin 15: biology and relevance to human disease. Blood 97, 14-32
2. Waldmann, T. A. (2006) The biology of interleukin-2 and interleukin-15: implications for cancer therapy and vaccine design. Nat Rev Immunol 6, 595-601
3. Zhu, X., Marcus, W. D., Xu, W., Lee, H. I., Han, K., Egan, J. O., Yovandich, J. L., Rhode, P. R., and Wong, H. C. (2009) Novel human interleukin-15 agonists. J Immunol 183, 3598-3607
4. Han, K. P., Zhu, X., Liu, B., Jeng, E., Kong, L., Yovandich, J. L., Vyas, V. V., Marcus, W. D., Chavaillaz, P. A., Romero, C. A., Rhode, P. R., and Wong, H. C. (2011) IL-15:IL-15 receptor alpha superagonist complex: high-level co-expression in recombinant mammalian cells, purification and characterization. Cytokine 56, 804-810
5. Xu, W., Jones, M., Liu, B., Zhu, X., Johnson, C. B., Edwards, A. C., Kong, L., Jeng, E. K., Han, K., Marcus, W. D., Rubinstein, M. P., Rhode, P. R., and Wong, H. C. (2013) Efficacy and mechanism-of-action of a novel superagonist interleukin-15: interleukin-15 receptor alphaSu/Fc fusion complex in syngeneic murine models of multiple myeloma. Cancer Res 73, 3075-3086
6. Mathios, D., Park, C. K., Marcus, W. D., Alter, S., Rhode, P. R., Jeng, E. K., Wong, H. C., Pardoll, D. M., and Lim, M. (2016) Therapeutic administration of IL-15 superagonist complex ALT-803 leads to long-term survival and durable antitumor immune response in a murine glioblastoma model. Int J Cancer 138, 187-194
7. Rosario, M., Liu, B., Kong, L., Collins, L. I., Schneider, S. E., Chen, X., Han, K., Jeng, E. K., Rhode, P. R., Leong, J. W., Schappe, T., Jewell, B. A., Keppel, C. R., Shah, K., Hess, B., Romee, R., Piwnica-Worms, D. R., Cashen, A. F., Bartlett, N. L., Wong, H. C., and Fehniger, T. A. (2016) The IL-15-Based ALT-803 Complex Enhances FcgammaRIIIa-Triggered NK Cell Responses and In Vivo Clearance of B Cell Lymphomas. Clinical cancer research: an official journal of the American Association for Cancer Research 22, 596-608
8. Wong, R. L., Liu, B., Zhu, X., You, L., Kong, L., Han, K. P., Lee, H. I., Chavaillaz, P. A., Jin, M., Wang, Y., Rhode, P. R., and Wong, H. C. (2011) Interleukin-15:Interleukin-15 receptor alpha scaffold for creation of multivalent targeted immune molecules. Protein Eng Des Sel 24, 373-383
9. Nishida, M., Usuda, S., Okabe, M., Miyakoda, H., Komatsu, M., Hanaoka, H., Teshigawara, K., and Niwa, O. (2007) Characterization of novel murine anti-CD20 monoclonal antibodies and their comparison to 2B8 and c2B8 (rituximab). Int J Oncol 31, 29-40
10. Hessell, A. J., Hangartner, L., Hunter, M., Havenith, C. E., Beurskens, F. J., Bakker, J. M., Lanigan, C. M., Landucci, G., Forthal, D. N., Parren, P. W., Marx, P. A., and Burton, D. R. (2007) Fc receptor but not complement binding is important in antibody protection against HIV. Nature 449, 101-104
11. Beers, S. A., Chan, C. H., French, R. R., Cragg, M. S., and Glennie, M. J. (2010) CD20 as a target for therapeutic type I and II monoclonal antibodies. Semin Hematol 47, 107-114
12. Rhode, P. R., Egan, J. O., Xu, W., Hong, H., Webb, G. M., Chen, X., Liu, B., Zhu, X., Wen, J., You, L., Kong, L., Edwards, A. C., Han, K., Shi, S., Alter, S., Sacha, J. B., Jeng, E. K., Cai, W., and Wong, H. C. (2016) Comparison of the Superagonist Complex, ALT-803, to IL15 as Cancer Immunotherapeutics in Animal Models. Cancer immunology research 4, 49-60
13. Sips, M., Krykbaeva, M., Diefenbach, T. J., Ghebremichael, M., Bowman, B. A., Dugast, A. S., Boesch, A. W., Streeck, H., Kwon, D. S., Ackerman, M. E., Suscovich, T. J., Brouckaert, P., Schacker, T. W., and Alter, G. (2016) Fc receptor-mediated phagocytosis in tissues as a potent mechanism for preventive and therapeutic HIV vaccine strategies. Mucosal immunology
14. Abes, R., Gelize, E., Fridman, W. H., and Teillaud, J. L. (2010) Long-lasting antitumor protection by anti-CD20 antibody through cellular immune response. Blood 116, 926-934
15. Wang, W., Erbe, A. K., Hank, J. A., Morris, Z. S., and Sondel, P. M. (2015) NK Cell-Mediated Antibody-Dependent Cellular Cytotoxicity in Cancer Immunotherapy. Frontiers in immunology 6, 368
16. van Meerten, T., and Hagenbeek, A. (2010) CD20-targeted therapy: the next generation of antibodies. Semin Hematol 47, 199-210
17. Goede, V., Fischer, K., Busch, R., Engelke, A., Eichhorst, B., Wendtner, C. M., Chagorova, T., de la Sema, J., Dilhuydy, M. S., Illmer, T., Opat, S., Owen, C. J., Samoylova, O., Kreuzer, K. A., Stilgenbauer, S., Dohner, H., Langerak, A. W., Ritgen, M., Kneba, M., Asikanius, E., Humphrey, K., Wenger, M., and Hallek, M. (2014) Obinutuzumab plus chlorambucil in patients with CLL and coexisting conditions. The New England journal of medicine 370, 1101-1110
18. Hillmen, P., Robak, T., Janssens, A., Babu, K. G., Kloczko, J., Grosicki, S., Doubek, M., Panagiotidis, P., Kimby, E., Schuh, A., Pettitt, A. R., Boyd, T., Montillo, M., Gupta, I. V., Wright, O., Dixon, I., Carey, J. L., Chang, C. N., Lisby, S., McKeown, A., and Offner, F. (2015) Chlorambucil plus ofatumumab versus chlorambucil alone in previously untreated patients with chronic lymphocytic leukaemia (COMPLEMENT 1): a randomised, multicentre, open-label phase 3 trial. Lancet (London, England) 385, 1873-1883
19. Ghetie, M. A., Bright, H., and Vitetta, E. S. (2001) Homodimers but not monomers of Rituxan (chimeric anti-CD20) induce apoptosis in human B-lymphoma cells and synergize with a chemotherapeutic agent and an immunotoxin. Blood 97, 1392-1398
20. Li, B., Shi, S., Qian, W., Zhao, L., Zhang, D., Hou, S., Zheng, L., Dai, J., Zhao, J., Wang, H., and Guo, Y. (2008) Development of novel tetravalent anti-CD20 antibodies with potent antitumor activity. Cancer Res 68, 2400-2408
21. Wong, H. C., Jeng, E. K., and Rhode, P. R. (2013) The IL-15-based superagonist ALT-803 promotes the antigen-independent conversion of memory CD8 T cells into innate-like effector cells with antitumor activity. Oncoimmunology 2, e26442
22. Smalls-Mantey, A., Doria-Rose, N., Klein, R., Patamawenu, A., Migueles, S. A., Ko, S. Y., Hallahan, C. W., Wong, H., Liu, B., You, L., Scheid, J., Kappes, J. C., Ochsenbauer, C., Nabel, G. J., Mascola, J. R., and Connors, M. (2012) Antibody-dependent cellular cytotoxicity against primary HIV-infected CD4+ T cells is directly associated with the magnitude of surface IgG binding. *Journal of virology* 86, 8672-8680
23. Seay, K., Church, C., Zheng, J. H., Deneroff, K., Ochsenbauer, C., Kappes, J. C., Liu, B., Jeng, E. K., Wong, H. C., and Goldstein, H. (2015) In Vivo Activation of Human NK Cells by Treatment with an Interleukin-15 Superagonist Potently Inhibits Acute In Vivo HIV-1 Infection in Humanized Mice. *Journal of virology* 89, 6264-6274
24. Zhu, E. F., Gai, S. A., Opel, C. F., Kwan, B. H., Surana, R., Mihm, M. C., Kauke, M. J., Moynihan, K. D., Angelini, A., Williams, R. T., Stephan, M. T., Kim, J. S., Yaffe, M. B., Irvine, D. J., Weiner, L. M., Dranoff, G., and Wittrup, K. D. (2015) Synergistic innate and adaptive immune response to combination immunotherapy with anti-tumor antigen antibodies and extended serum half-life IL-2. *Cancer cell* 27, 489-501
25. Park, S., Jiang, Z., Mortenson, E. D., Deng, L., Radkevich-Brown, O., Yang, X., Sattar, H., Wang, Y., Brown, N. K., Greene, M., Liu, Y., Tang, J., Wang, S., and Fu, Y. X. (2010) The therapeutic effect of anti-HER2/neu antibody depends on both innate and adaptive immunity. *Cancer cell* 18, 160-170
26. Hilchey, S. P., Hyrien, O., Mosmann, T. R., Livingstone, A. M., Friedberg, J. W., Young, F., Fisher, R. I., Kelleher, R. J., Jr., Bankert, R. B., and Bernstein, S. H. (2009) Rituximab immunotherapy results in the induction of a lymphoma idiotype-specific T-cell response in patients with follicular lymphoma: support for a "vaccinal effect" of rituximab. *Blood* 113, 3809-3812
27. DiLillo, D. J., and Ravetch, J. V. (2015) Differential Fc-Receptor Engagement Drives an Anti-tumor Vaccinal Effect. *Cell* 161, 1035-1045
28. Hughes, M. S., Yu, Y. Y., Dudley, M. E., Zheng, Z., Robbins, P. F., Li, Y., Wunderlich, J., Hawley, R. G., Moayeri, M., Rosenberg, S. A., and Morgan, R. A. (2005) Transfer of a TCR gene derived from a patient with a marked antitumor response conveys highly active T-cell effector functions. *Human gene therapy* 16, 457-472
29. Shi, S., Orbay, H., Yang, Y., Graves, S. A., Nayak, T. R., Hong, H., Hernandez, R., Luo, H., Goel, S., Theuer, C. P., Nickles, R. J., and Cai, W. (2015) PET Imaging of Abdominal Aortic Aneurysm with 64Cu-Labeled Anti-CD105 Antibody Fab Fragment. *Journal of nuclear medicine: official publication, Society of Nuclear Medicine* 56, 927-932
30. Shi, S., Hong, H., Orbay, H., Graves, S. A., Yang, Y., Ohman, J. D., Liu, B., Nickles, R. J., Wong, H. C., and Cai, W. (2015) ImmunoPET of tissue factor expression in triple-negative breast cancer with a radiolabeled antibody Fab fragment. *European journal of nuclear medicine and molecular imaging* 42, 1295-1303

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated soluble fusion protein complex comprising at least two soluble fusion proteins, wherein
the first fusion protein comprises (a) a first binding domain covalently linked to (b) a interleukin-15 (IL-15) polypeptide domain; and the second fusion protein comprises (c) a second binding domain covalently linked to (d) a soluble IL-15 receptor alpha sushi-binding domain (IL-15RαSu) fused to an immunoglobulin Fc domain,
wherein the first binding domain comprises an anti-CD3 antibody and the second binding domain comprises a means for binding an antigen on a tumor cell, and
wherein the IL-15 domain of the first fusion protein binds to the soluble IL-15RαSu domain of the second fusion protein to form a soluble fusion protein complex, and wherein the first fusion protein comprises the amino acid sequence set forth in SEQ ID NO: 2.

2. The soluble fusion protein complex of claim 1, wherein the IL-15 polypeptide is an IL-15 variant comprising an N72D mutation (IL-15N72D).

3. The soluble fusion protein complex of claim 1, wherein the anti-CD3 antibody comprises an immunoglobulin light chain variable domain covalently linked to an immunoglobulin heavy chain variable domain by a polypeptide linker sequence.

4. The soluble fusion protein of claim 1, wherein the means for binding an antigen on a tumor cell binds an antigen on a tumor cell and comprises an anti-CD20 antibody.

5. The soluble fusion protein complex of claim 4, wherein the anti-CD20 antibody comprises an immunoglobulin light chain variable domain covalently linked to an immunoglobulin heavy chain variable domain by a polypeptide linker sequence.

6. The soluble fusion protein complex of claim 4, wherein the second fusion protein comprises the amino acid sequence set forth in SEQ ID NO: 4.

7. A soluble fusion protein complex comprising a first soluble fusion protein complex of claim 1 covalently linked to a second soluble fusion protein complex of claim 1.

8. The soluble fusion protein complex of claim 7, wherein the first soluble fusion protein complex is covalently linked to the second soluble fusion protein complex by a disulfide bond linking the Fc domain of the first soluble fusion protein complex to the Fc domain of the second soluble fusion protein complex.

9. A nucleic acid sequence encoding the first fusion protein of claim 1, wherein said nucleic acid sequence comprises the sequence set forth in SEQ ID NO: 1.

10. The nucleic acid sequence of claim 9, wherein the nucleic acid sequence further comprises a promoter, translation initiation signal, and leader sequence operably linked to the sequence encoding the fusion protein.

11. The soluble fusion protein complex of claim 1, wherein a nucleic acid sequence encoding the second fusion protein comprises the sequence set forth in SEQ ID NO: 3.

12. The soluble fusion protein complex claim 11, wherein the nucleic acid sequence further comprises a promoter, translation initiation signal, and leader sequence operably linked to the sequence encoding the fusion protein.

13. The soluble fusion protein complex of claim 1, wherein the antigen-specific binding domain recognizes disease antigens.

14. The soluble fusion protein complex of claim 13, wherein the disease antigens are associated with neoplasia, infectious disease or autoimmune disease.

15. The soluble fusion protein complex of claim 1, wherein the second binding domain comprises a tumor cell antigen-specific binding domain.

* * * * *

SEQUENCE LISTING

<160> NUMBER OF SEQ ID NOS: 6

<210> SEQ ID NO 1
<211> LENGTH: 1140
<212> TYPE: DNA
<213> ORGANISM: Artificial Sequence
<220> FEATURE:
<223> OTHER INFORMATION: Synthetic polynucleotide

<400> SEQUENCE: 1

```
atggagacag acacactcct gttatgggta ctgctgctct gggttccagg ttccaccggt      60
caaattgttc tcacccagtc tccagcaatc atgtctgcat ctccagggga gaaggtcacc     120
atgacctgca gtgccagctc aagtgtaagt tacatgaact ggtaccagca gaagtcaggc     180
acctccccca aaagatggat ttatgacaca tccaaactgg cttctggagt ccctgctcac     240 ttcagggca gtgggtctgg gacctcttac tctctcacaa tcagcggcat ggaggctgaa      300
gatgctgcca cttattactg ccagcagtgg agtagtaacc cattcacgtt cggctcgggg     360
acaaagttgg aaataaaccg gactagtgga ggtggcggat caggaggcgg aggttctggc     420
ggaggtggga gtctcgagca ggtccagctg cagcagtctg ggctgaact ggcaagacct      480
```

```
ggggcctcag tgaagatgtc ctgcaaggct tctggctaca cctttactag gtacacgatg      540
cactgggtaa acagaggcc tggacagggt ctggaatgga ttggatacat taatcctagc      600
cgtggttata ctaattacaa tcagaagttc aaggacaagg ccacattgac tacagacaaa      660
tcctccagca cagcctacat gcaactgagc agcctgacat ctgaggactc tgcagtctat      720
tactgtgcaa gatattatga tgatcattac tgccttgact actggggcca aggcaccact      780
ctcacagtct cctcaaactg ggttaacgta ataagtgatt tgaaaaaaat tgaagatctt      840
attcaatcta tgcatattga tgctacttta tatacggaaa gtgatgttca ccccagttgc      900
aaagtaacag caatgaagtg ctttctcttg gagttacaag ttatttcact tgagtccgga      960
gatgcaagta ttcatgatac agtagaaaat ctgatcatcc tagcaaacga cagtttgtct     1020
tctaatggga atgtaacaga atctggatgc aaagaatgtg aggaactgga ggaaaaaaat     1080
attaaagaat ttttgcagag ttttgtacat attgtccaaa tgttcatcaa cacttcttaa     1140
```

<210> SEQ ID NO 2
<211> LENGTH: 379
<212> TYPE: PRT
<213> ORGANISM: Artificial Sequence
<220> FEATURE:
<223> OTHER INFORMATION: Synthetic polypeptide

<400> SEQUENCE: 2

```
Met Glu Thr Asp Thr Leu Leu Leu Trp Val Leu Leu Leu Trp Val Pro
1               5                   10                  15

Gly Ser Thr Gly Gln Ile Val Leu Thr Gln Ser Pro Ala Ile Met Ser
            20                  25                  30

Ala Ser Pro Gly Glu Lys Val Thr Met Thr Cys Ser Ala Ser Ser Ser
        35                  40                  45

Val Ser Tyr Met Asn Trp Tyr Gln Gln Lys Ser Gly Thr Ser Pro Lys
    50                  55                  60

Arg Trp Ile Tyr Asp Thr Ser Lys Leu Ala Ser Gly Val Pro Ala His
65                  70                  75                  80

Phe Arg Gly Ser Gly Ser Gly Thr Ser Tyr Ser Leu Thr Ile Ser Gly
                85                  90                  95

Met Glu Ala Glu Asp Ala Ala Thr Tyr Tyr Cys Gln Gln Trp Ser Ser
            100                 105                 110

Asn Pro Phe Thr Phe Gly Ser Gly Thr Lys Leu Glu Ile Asn Arg Thr
        115                 120                 125

Ser Gly Gly Gly Gly Ser Gly Gly Gly Ser Gly Gly Gly Gly Ser
    130                 135                 140

Leu Glu Gln Val Gln Leu Gln Gln Ser Gly Ala Glu Leu Ala Arg Pro
145                 150                 155                 160

Gly Ala Ser Val Lys Met Ser Cys Lys Ala Ser Gly Tyr Thr Phe Thr
                165                 170                 175

Arg Tyr Thr Met His Trp Val Lys Gln Arg Pro Gly Gln Gly Leu Glu
            180                 185                 190

Trp Ile Gly Tyr Ile Asn Pro Ser Arg Gly Tyr Thr Asn Tyr Asn Gln
        195                 200                 205

Lys Phe Lys Asp Lys Ala Thr Leu Thr Thr Asp Lys Ser Ser Ser Thr
    210                 215                 220

Ala Tyr Met Gln Leu Ser Ser Leu Thr Ser Glu Asp Ser Ala Val Tyr
225                 230                 235                 240

Tyr Cys Ala Arg Tyr Tyr Asp Asp His Tyr Cys Leu Asp Tyr Trp Gly
                245                 250                 255
```

```
Gln Gly Thr Thr Leu Thr Val Ser Ser Asn Trp Val Asn Val Ile Ser
            260                 265                 270

Asp Leu Lys Lys Ile Glu Asp Leu Ile Gln Ser Met His Ile Asp Ala
        275                 280                 285

Thr Leu Tyr Thr Glu Ser Asp Val His Pro Ser Cys Lys Val Thr Ala
        290                 295                 300

Met Lys Cys Phe Leu Leu Glu Leu Gln Val Ile Ser Leu Glu Ser Gly
305                 310                 315                 320

Asp Ala Ser Ile His Asp Thr Val Glu Asn Leu Ile Ile Leu Ala Asn
                325                 330                 335

Asp Ser Leu Ser Ser Asn Gly Asn Val Thr Glu Ser Gly Cys Lys Glu
                340                 345                 350

Cys Glu Glu Leu Glu Glu Lys Asn Ile Lys Glu Phe Leu Gln Ser Phe
            355                 360                 365

Val His Ile Val Gln Met Phe Ile Asn Thr Ser
            370                 375

<210> SEQ ID NO 3
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 3
atggattttc aggtgcagat tatcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagttaca tccactggtt ccagcagaag     180
ccaggatcct cccccaaacc ctggatttat gccacatcca acctggcttc tggagtccct     240
gttcgcttca gtggcagtgg gtctgggact tcttactctc tcacaatcag cagagtggag     300
gctgaagatg ctgccactta ttactgccag cagtggacta gtaacccacc cacgttcgga     360 gggggggacca agctggaaat caaaagtgga ggtggcggat ccggaggtgg aggttctggt     420
ggaggtggga gtcaggtaca actgcagcag cctggggctg agctggtgaa gcctggggcc     480
tcagtgaaga tgtcctgcaa ggcttctggc tacacattta ccagttacaa tatgcactgg     540
gtaaaacaga cacctggtcg gggcctggaa tggattggag ctatttatcc cggaaatggt     600
gatacttcct acaatcagaa gttcaaaggc aaggccacat tgactgcaga caaatcctcc     660
agcacagcct acatgcagct cagcagcctg acatctgagg actctgcggt ctattactgt     720
gcaagatcga cttactacgg cggtgactgg tacttcratg tctggggcgc agggaccacg     780
gtcacmgtct ctgcaatcac gtgccctccc cccatgtccg tggaacacgc agacatctgg     840
gtcaagagct acagcttgta ctccagggag cggtacattt gtaactctgg tttcaagcgt     900
aaagccggca cgtccagcct gacggagtgc gtgttgaaca aggccacgaa tgtcgcccac     960
tggacaaccc ccagtctcaa atgcattaga gagccgaaat cttgtgacaa aactcacaca    1020
tgcccaccgt gcccagcacc tgaactcctg gggggaccgt cagtcttcct cttccccccca    1080 aaacccaagg acaccctcat gatctcccgg acccctgagg tcacatgcgt ggtggtggac    1140
gtgagccacg aagaccctga ggtcaagttc aactggtacg tggacggcgt ggaggtgcat    1200
aatgccaaga caaagccgcg ggaggagcag tacaacagca cgtaccgtgt ggtcagcgtc    1260
ctcaccgtcc tgcaccagga ctggctgaat ggcaaggagt acaagtgcaa ggtctccaac    1320
```

-continued

```
aaagccctcc cagcccccat cgagaaaacc atctccaaag ccaagggca gccccgagaa    1380 ccacaggtgt acaccctgcc cccatcccgg gatgagctga ccaagaacca ggtcagcctg    1440
acctgcctgg tcaaaggctt ctatcccagc gacatcgccg tggagtggga gagcaatggg    1500
cagccggaga caactacaa gaccacgcct cccgtgctgg actccgacgg ctccttcttc    1560
ctctacagca agctcaccgt ggacaagagc aggtggcagc aggggaacgt cttctcatgc    1620
tccgtgatgc atgaggctct gcacaaccac tacacgcaga agagcctctc cctgtctcct    1680
ggtaaataa                                                          1689

<210> SEQ ID NO 4
<211> LENGTH: 540
<212> TYPE: PRT
<213> ORGANISM: Artificial Sequence
<220> FEATURE:
<223> OTHER INFORMATION: Synthetic polypeptide

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Lys Pro Gly Ala Ser Val Lys Met Ser Cys
    130                 135                 140

Lys Ala Ser Gly Tyr Thr Phe Thr Ser Tyr Asn Met His Trp Val Lys
145                 150                 155                 160

Gln Thr Pro Gly Arg Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Ser Thr Tyr Tyr
    210                 215                 220

Gly Gly Asp Trp Tyr Phe Asn Val Trp Gly Ala Gly Thr Thr Val Thr
225                 230                 235                 240

Val Ser Ala Ile Thr Cys Pro Pro Met Ser Val Glu His Ala Asp
                245                 250                 255

Ile Trp Val Lys Ser Tyr Ser Leu Tyr Ser Arg Glu Arg Tyr Ile Cys
            260                 265                 270

Asn Ser Gly Phe Lys Arg Lys Ala Gly Thr Ser Ser Leu Thr Glu Cys
        275                 280                 285

Val Leu Asn Lys Ala Thr Asn Val Ala His Trp Thr Thr Pro Ser Leu
```

```
            290                 295                 300
Lys Cys Ile Arg Glu Pro Lys Ser Cys Asp Lys Thr His Thr Cys Pro
305                 310                 315                 320

Pro Cys Pro Ala Pro Glu Leu Leu Gly Gly Pro Ser Val Phe Leu Phe
                325                 330                 335

Pro Pro Lys Pro Lys Asp Thr Leu Met Ile Ser Arg Thr Pro Glu Val
                340                 345                 350

Thr Cys Val Val Val Asp Val Ser His Glu Asp Pro Glu Val Lys Phe
                355                 360                 365

Asn Trp Tyr Val Asp Gly Val Glu Val His Asn Ala Lys Thr Lys Pro
                370                 375                 380

Arg Glu Glu Gln Tyr Asn Ser Thr Tyr Arg Val Val Ser Val Leu Thr
385                 390                 395                 400

Val Leu His Gln Asp Trp Leu Asn Gly Lys Glu Tyr Lys Cys Lys Val
                405                 410                 415

Ser Asn Lys Ala Leu Pro Ala Pro Ile Glu Lys Thr Ile Ser Lys Ala
                420                 425                 430

Lys Gly Gln Pro Arg Glu Pro Gln Val Tyr Thr Leu Pro Pro Ser Arg
                435                 440                 445

Asp Glu Leu Thr Lys Asn Gln Val Ser Leu Thr Cys Leu Val Lys Gly
                450                 455                 460

Phe Tyr Pro Ser Asp Ile Ala Val Glu Trp Glu Ser Asn Gly Gln Pro
465                 470                 475                 480

Glu Asn Asn Tyr Lys Thr Thr Pro Pro Val Leu Asp Ser Asp Gly Ser
                485                 490                 495

Phe Phe Leu Tyr Ser Lys Leu Thr Val Asp Lys Ser Arg Trp Gln Gln
                500                 505                 510

Gly Asn Val Phe Ser Cys Ser Val Met His Glu Ala Leu His Asn His
                515                 520                 525

Tyr Thr Gln Lys Ser Leu Ser Leu Ser Pro Gly Lys
                530                 535                 540

<210> SEQ ID NO 5
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 5

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
                20                  25                  30

Glu Asp Leu Ile Gln Ser Met His Ile Asp Ala Thr Leu Tyr Thr Glu
                35                  40                  45

Ser Asp Val His Pro Ser Cys Lys Val Thr Ala Met Lys Cys Phe Leu
                50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asp Ser Leu Ser Ser
                85                  90                  95

Asn Gly Asn Val Thr Glu Ser Gly Cys Lys Glu Cys Glu Glu Leu Glu
                100                 105                 110

Glu Lys Asn Ile Lys Glu Phe Leu Gln Ser Phe Val His Ile Val Gln
```

```
                115            120            125
Met Phe Ile Asn Thr Ser
        130

<210> SEQ ID NO 6
<211> LENGTH: 316
<212> TYPE: PRT
<213> ORGANISM: Artificial Sequence
<220> FEATURE:
<223> OTHER INFORMATION: Synthetic polypeptide

<400> SEQUENCE: 6

Met Asp Arg Leu Thr Ser Ser Phe Leu Leu Leu Ile Val Pro Ala Tyr
1               5                   10                  15

Val Leu Ser Ile Thr Cys Pro Pro Met Ser Val Glu His Ala Asp
            20                  25                  30

Ile Trp Val Lys Ser Tyr Ser Leu Tyr Ser Arg Glu Arg Tyr Ile Cys
                35                  40                  45

Asn Ser Gly Phe Lys Arg Lys Ala Gly Thr Ser Ser Leu Thr Glu Cys
        50                  55                  60

Val Leu Asn Lys Ala Thr Asn Val Ala His Trp Thr Thr Pro Ser Leu
65                  70                  75                  80

Lys Cys Ile Arg Glu Pro Lys Ser Cys Asp Lys Thr His Thr Cys Pro
                85                  90                  95

Pro Cys Pro Ala Pro Glu Leu Leu Gly Gly Pro Ser Val Phe Leu Phe
            100                 105                 110

Pro Pro Lys Pro Lys Asp Thr Leu Met Ile Ser Arg Thr Pro Glu Val
                115                 120                 125

Thr Cys Val Val Val Asp Val Ser His Glu Asp Pro Glu Val Lys Phe
        130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
    210                 215                 220

Asp Glu Leu Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Lys Leu Thr Val Asp Lys Ser Arg Trp Gln Gln
        275                 280                 285

Gly Asn Val Phe Ser Cys Ser Val Met His Glu Ala Leu His Asn His
    290                 295                 300

Tyr Thr Gln Lys Ser Leu Ser Leu Ser Pro Gly Lys
305                 310                 315
```